(12) United States Patent
Cho et al.

(10) Patent No.: US 11,866,460 B2
(45) Date of Patent: *Jan. 9, 2024

(54) BROAD-SPECTRUM ANTI-INFECTIVE PEPTIDES

(71) Applicant: NANYANG TECHNOLOGICAL UNIVERSITY, Singapore (SG)

(72) Inventors: Nam-Joon Cho, Singapore (SG); Joshua Alexander Jackman, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/348,593

(22) Filed: Jun. 15, 2021

(65) Prior Publication Data

US 2022/0402972 A1    Dec. 22, 2022

Related U.S. Application Data

(63) Continuation of application No. 17/081,166, filed on Oct. 27, 2020, now abandoned, which is a continuation of application No. 16/421,119, filed on May 23, 2019, now abandoned, which is a continuation of application No. 15/738,730, filed as application No. PCT/SG2016/050291 on Jun. 24, 2016, now Pat. No. 10,351,604.

(60) Provisional application No. 62/184,354, filed on Jun. 25, 2015.

(51) Int. Cl.
| | | |
|---|---|---|
| C07K 14/00 | (2006.01) | |
| C07K 14/18 | (2006.01) | |
| A61K 47/60 | (2017.01) | |
| A61P 31/12 | (2006.01) | |
| C07K 14/005 | (2006.01) | |
| A61P 31/20 | (2006.01) | |
| A61P 31/14 | (2006.01) | |
| A61P 31/18 | (2006.01) | |
| A61P 31/04 | (2006.01) | |
| A61P 31/16 | (2006.01) | |
| A01N 25/04 | (2006.01) | |
| A01N 47/44 | (2006.01) | |
| A61K 9/00 | (2006.01) | |
| A61K 9/06 | (2006.01) | |
| A61K 9/08 | (2006.01) | |
| C07K 7/08 | (2006.01) | |
| A61K 38/00 | (2006.01) | |

(52) U.S. Cl.
CPC ............ C07K 14/001 (2013.01); A01N 25/04 (2013.01); A01N 47/44 (2013.01); A61K 9/0014 (2013.01); A61K 9/0019 (2013.01); A61K 9/06 (2013.01); A61K 9/08 (2013.01); A61K 47/60 (2017.08); A61P 31/04 (2018.01); A61P 31/12 (2018.01); A61P 31/14 (2018.01); A61P 31/16 (2018.01); A61P 31/18 (2018.01); A61P 31/20 (2018.01); C07K 7/08 (2013.01); C07K 14/005 (2013.01); C07K 14/1833 (2013.01); A61K 38/00 (2013.01); Y02A 50/30 (2018.01)

(58) Field of Classification Search
CPC ............... C07K 14/001; C07K 14/005; C07K 14/1833; A61K 47/60; A61P 31/12
See application file for complete search history.

(56) References Cited

U.S. PATENT DOCUMENTS

| | | |
|---|---|---|
| 7,326,536 B2 | 2/2008 | Glenn et al. |
| 8,093,353 B2 | 1/2012 | Glenn et al. |
| 8,663,648 B2 | 3/2014 | Glenn et al. |
| 8,728,793 B2 | 3/2014 | Glenn et al. |
| 8,815,522 B2 | 8/2014 | Sasisekharan et al. |
| 10,351,604 B2 | 7/2019 | Cho et al. |
| 2004/0265792 A1 | 12/2004 | Glenn et al. |
| 2007/0073039 A1 | 3/2007 | Chisari et al. |
| 2008/0125367 A1* | 5/2008 | Glenn ............... C07K 14/005 514/1.2 |
| 2009/0105151 A1* | 4/2009 | Glenn .................. A01N 37/46 435/238 |
| 2010/0093086 A1 | 4/2010 | Lin et al. |
| 2013/0337001 A1 | 12/2013 | Filatov et al. |

FOREIGN PATENT DOCUMENTS

| | | |
|---|---|---|
| WO | WO 2002/089731 A2 | 11/2002 |
| WO | WO 2008/133759 A2 | 11/2008 |
| WO | WO 2009/014615 A2 | 1/2009 |

OTHER PUBLICATIONS

Blazquez et al., 2014, Stress responses in flavivirus-infected cells: activation of unfolded protein response and autophagy, Frontiers in Microbiology, 5: 266 (7 pages).*
Aubry et al., "Inactivation of Zika virus in plasma with amotosalen and ultraviolet A illumination," *Transfusion* 56(1):33-40 (2016).
Banerjee et al., "Poly(ethylene glycol)-Prodrug Conjugates: Concept, Design, and Applications" Journal of Drug Delivery, 2012: 1-17 (2012).
Betts and Russell, "Amino acid properties and consequences of substitutions," *Bioinformatics for Geneticists*, 289-316 (2003).

(Continued)

*Primary Examiner* — Amber D Steele
(74) *Attorney, Agent, or Firm* — SEED INTELLECTUAL PROPERTY LAW GROUP LLP

(57) ABSTRACT

Provided herein are anti-infective peptides and uses thereof. Such anti-infective peptides are useful against bacteria and viruses. Also provided herein are compositions comprising said anti-infective peptides.

19 Claims, 5 Drawing Sheets

Figure 1A:
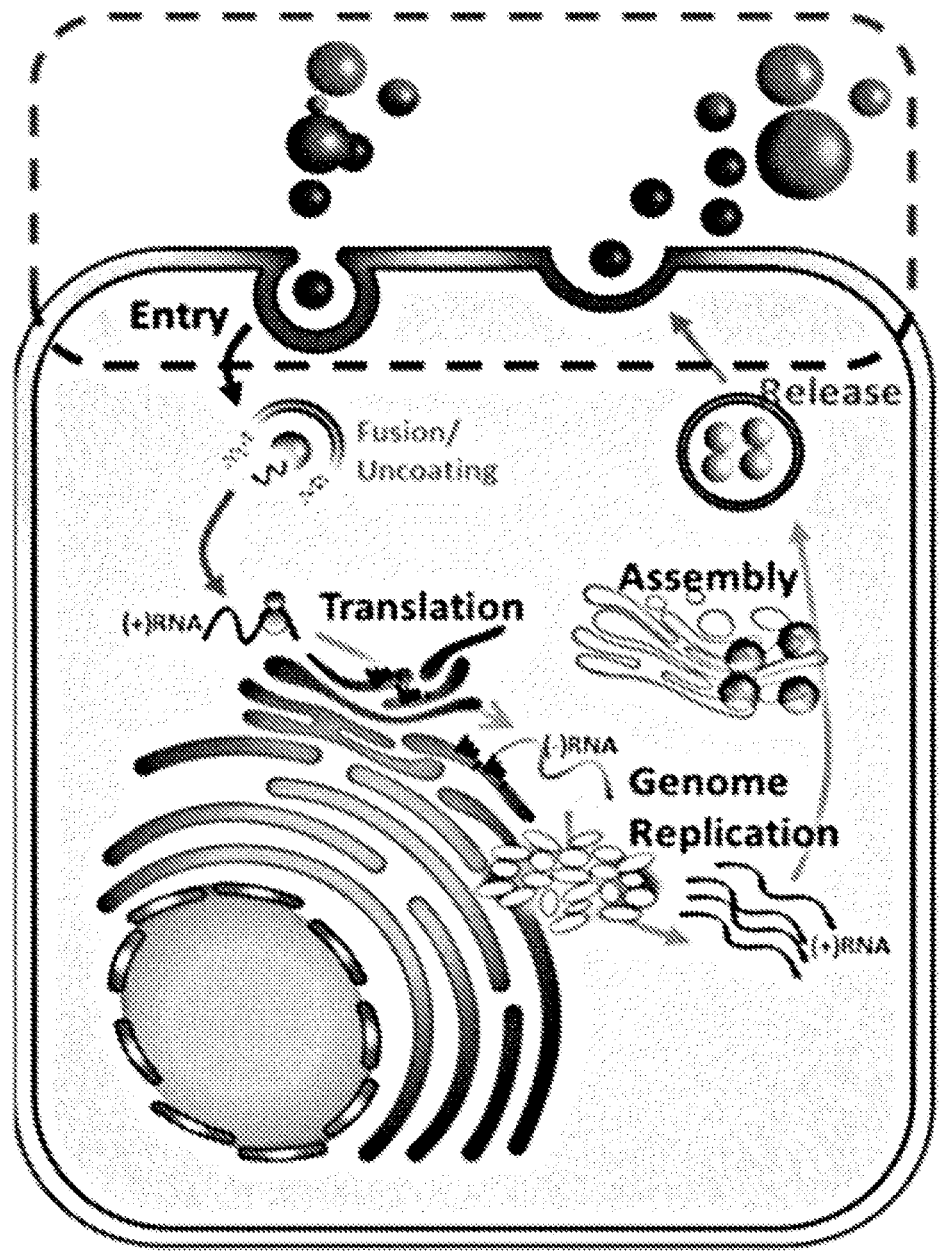

Specification includes a Sequence Listing.

(56) References Cited

OTHER PUBLICATIONS

Bird et al., "Hydrocarbon double-stapling remedies the proteolytic instability of a lengthy peptide therapeutic," *Proc. Natl. Acad. Sci. U.S.A.* 107(32):14093-14098 (2010).
Bobardt et al., "Hepatitis C virus NS5A anchor peptide disrupts human immunodeficiency virus," *Proc. Natl. Acad. Sci. U.S.A.* 105(14):5525-5530 (2008).
Brown et al, "Cationic host defense (antimicrobial) peptides," *Curr. Opin. Immunol.* 18(1):24-30 (2006).
Cao-Lormeau et al., "Guillain-Barré Syndrome outbreak caused by Zika virus infection in French Polynesia," *Lancet* 387(10027):1531-1539 (2016).
Chaldi et al., "A new functional membrane protein microarray based on tethered phospholipid bilayers," *Analyst.* 143(9):2165-2173 (2018).
Chan et al., "Zika fever and congenital Zika syndrome: An unexpected emerging arboviral disease," *J. Infect.* 72(5):507-524 (2016).
Cheng et al., "A virocidal amphipathic α-helical peptide that inhibits hepatitis C virus infection in vitro," *Proc. Natl. Acad. Sci. U.S.A.* 105:3088-3093 (2008).
Cho et al., "Alpha-helical peptide-induced vesicle rupture revealing new insight into the vesicle fusion process as monitored in situ by quartz crystal microbalance-dissipation and reflectometry," *Anal. Chem.* 81(12):4752-4761 (2009).
Cho et al., "Binding Dynamics of Hepatitis C Virus' NS5A Amphipathic Peptide to Cell and Model Membranes," *J. Virol.* 81(12):6682-6689 (2007).
Cho et al., "Employing an amphipathic viral peptide to create a lipid bilayer on Au and $TiO_2$," *J. Am. Chem. Soc.* 129(33):10050-10051 (2007).
Cho et al., "Mechanism of an Amphipathic α-Helical Peptide's Antiviral Activity Involves Size-Dependent Virus Particle Lysis," *ACS Chem. Biol.* 4(12):1061-1067 (2009).
Dai et al., "Structures of the Zika Virus Envelope Protein and Its Complex with a Flavivirus Broadly Protective Antibody," *Cell Host Microbe* 19:696-704 (2016).
De Witte et al., "HSV Neutralization by the Microbicidal Candidate CSA," *PloS One* 6(5):e18917 (2011).
Denton et al., "One Percent Tenofovir Applied Topically to Humanized BLT Mice and Used According to the CAPRISA 004 Experimental Design Demonstrates Partial Protection from Vaginal HIV Infection, Validating the BLT Model for Evaluation of New Microbicide Candidates," *J. Virol.* 85(15):7582-7593 (2011).
Dick et al., "Zika virus. I. Isolations and serological specificity," *Trans. R. Soc. Trop. Med. Hyg.* 46(5):509-520 (1952).
Duffy et al, "Zika Virus Outbreak on Yap Island, Federated States of Micronesia," *N. Engl. J. Med.* 360:2536-2543 (2009).
Elazar et al., "Amphipathic Helix-Dependent Localization of NS5A Mediates Hepatitis C Virus RNA Replication," *J. Virol.* 77(10):6055-6061 (2003).
European Patent Office Extended European Search Report for Application No. 16814828.6, dated Dec. 21, 2018 (13 pages).
Faye et al., "Molecular Evolution of Zika Virus during Its Emergence in the 20th Century," *PLoS Negl. Trop. Dis.* 8(1):e2636 (2014).
Ferhan et al., "Integration of Quartz Crystal Microbalance-Dissipation and Reflection-Mode Localized Surface Plasmon Resonance Sensors for Biomacromolecular Interaction Analysis," *Anal. Chem.* 88(24):12524-12531 (2016) (Epub Dec. 8, 2016).
Ferhan et al., "Nanoplasmonic Sensing Architectures for Decoding Membrane Curvature-Dependent Biomacromolecular Interactions," *Anal. Chem.* 90(12):7458-7466 (2018).
Fernández-Romero et al., "Preclinical assessments of vaginal microbicide candidate safety and efficacy," *Adv. Drug Deliv. Rev.* 92:27-39 (2015).
Fox et al., "Antimicrobial peptides stage a comeback," *Nat. Biotechnol.* 31:379-382 (2013).
Genbank Accession No. DQ380208.1, "Rift Valley fever virus strain MP-12 segment M, complete sequence." URL: https://www.ncbi.nlm.nih.gov/nuccore/DQ380208 (2007).

Ghosh & Haldar, "Membrane-Active Small Molecules: Designs Inspired by Antimicrobial Peptides," *ChemMedChem* 10(10):1606-1624 (2015).
Giangaspero et al., "Amphipathic α helical antimicrobial peptides: A systemic study of the effects of structural and physical properties on biological," *Eur. J. Biochem.* 268(21):5589-5600 (2001).
Gulland, "Zika virus is a global public health emergency, declares WHO," *BMJ* 352:i657 (2016).
Hancock et al., "Antimicrobial and host-defense peptides as new anti-infective therapeutic strategies," *Nat. Biotechnol.* 24(12):1551-1557 (2006).
Hancock et al., "Peptide antibiotics," *Antimicrob. Agents Chemother.* 43(6):1317-1323 (1999).
Hancock, "Cationic peptides: effectors in innate immunity and novel antimicrobials," *Lancet Infect. Dis.* 1(3):156-164 (2001).
Hanson et al., "Cholesterol-Enriched Domain Formation Induced by Viral-Encoded, Membrane-Active Amphipathic Peptide," *Biophys. J.* 110(1):176-187 (2016).
Hopp et al., "A short polypeptide marker sequence useful for recombinant protein identification and purification," *Bio/Technology*, 6:1204-1210 (1988).
Huang et al., "Molecular mechanism of Peptide-induced pores in membranes," *Phys. Rev. Lett.* 92(19):198304 (2004).
Huang, "Molecular mechanism of antimicrobial peptides: the origin of cooperativity," *Biochim. Biophys. Acta* 1758(9):1292-1302 (2006).
Jackman et al., "Correlation between Membrane Partitioning and Functional Activity in a Single Lipid Vesicle Assay Establishes Design Guidelines for Antiviral Peptides" *Small* 11(20):2372-2379 (2015).
Jackman et al., "Deciphering How Pore Formation Causes Strain-Induced Membrane Lysis of Lipid Vesicles," *J. Am. Chem. Soc.* 138(4):1406-1413 (2016).
Jackman et al., "Materials Nanoarchitectonics for Mechanical Tools in Chemical and Biological Sensing," *Chem. Asian J.* 13(22):3366-3377 (2018).
Jackman et al., "Model Membrane Platforms for Biomedicine: Case Study on Antiviral Drug Development," *Biointerphases* 7(18):1-20 (2012).
Jackman et al., "Nanomedicine for Infectious Disease Applications: Innovation towards Broad-Spectrum Treatment of Viral Infections," *Small* 12(9):1133-1139 (2016).
Jackman et al., "Nanoplasmonic sensors for biointerfacial science," *Chem. Soc. Rev.* 46(12):3615-3660 (2017).
Jackman et al., "Rupture of Lipid Vesicles by a Broad-Spectrum Antiviral Peptide: Influence of Vesicle Size," *J. Phys. Chem.* 117(50):16117-16128 (2013).
Jackman et al., "Targeting the Achilles Heel of Mosquito-Borne Viruses for Antiviral Therapy," *ACS Infect. Dis.* 5(1):4-8 (2019) (Epub Nov. 2, 2018).
Jackman et al., "Targeting the Achilles Heel of Zika Virus and Other Emerging Viral Pathogens," *Adv. Therap.* 1:1800045 (2018).
Jackman et al., "Therapeutic Treatment of Zika Virus Infection Using a Brain-Penetrating Antiviral Peptide," *Nat. Mater.* 17(11):971-977 (2018); Supplementary Information (3 pages).
Kern et al., "In vitro activity and mechanism of action of methylenecyclopropane analogs of nucleosides against herpesvirus replication," *Antimicrob. Agents Chemother.* 49(3):1039-1045 (2005).
Kim et al., "Correlating single-molecule and ensemble-average measurements of peptide adsorption onto different inorganic materials," *Phys. Chem. Chem. Phys.* 18(21):14454-14459 (2016).
Kim et al., "Quantitative Evaluation of Viral Protein Binding to Phosphoinositide Receptors and Pharmacological Inhibition," *Anal. Chem.* 89(18):9742-9750 (2017).
Kostyuchenko et al., "Structure of the thermally stable Zika virus," *Nature* 533:425-428 (2016).
Krauson et al., "Conformational Fine-Tuning of Pore-Forming Peptide Potency and Selectivity," *J. Am. Chem. Soc.* 137(51):16144-16152 (2015).
Lalezari et al., "Enfuvirtide, an HIV-1 fusion inhibitor, for drug-resistant HIV infection in North and South America," *N. Eng. J. Med.* 348:2175-2185 (2003).

(56) References Cited

OTHER PUBLICATIONS

Lin et al., "HCV Peptide (C5A), an Amphipathic α-Helical Peptide of Hepatitis Virus C, Is an Activator of N-Formyl Peptide Receptor in Human Phagocytes," *J. Immunol.* 186(4):2087-2094 (2011).
Lindenbach et al., "Flaviviridae: The Viruses and Their Replication," *Fields Virology, 5th Edition*, 1101-1152 (2007).
Lucey and Gostin, "The Emerging Zika Pandemic: Enhancing Preparedness," *JAMA* 315(9):865-866 (2016).
Malone et al., "Zika Virus: Medical Countermeasure Development Challenges," *PLoS Neg.l Trop. Dis.* 10(3):e0004530 (2016).
Maskiewicz et al., "Sublimable C5A delivery provides sustained and prolonged anti-HIV microbicidal activities," *Antimicrob. Agents Chemother.* 56(6):3336-3343 (2012).
Melo et al., "Antimicrobial peptides: linking partition, activity and high membrane-bound concentrations," *Nat. Rev. Microbiol.* 7:245-250 (2009).
Melo et al., "The Mechanism of Action of Antimicrobial Peptides: Lipid Vesicles vs. Bacteria," *Front. Immunol.* 3:236 (2012).
Mlakar et al., "Zika Virus Associated with Microcephaly," *N. Engl. J. Med.* 374:951-958 (2016).
Mukhopadhyay et al., "A structural perspective of the flavivirus life cycle," *Nat. Rev. Microbiol.* 3(1):13-22 (2005).
Musso et al., "Potential sexual transmission of Zika virus," *Emerg. Infect. Dis.* 21(2):359-361 (2015).
Nasir et al., "Detection of Amphipathic Viral Peptide on Screen-Printed Electrodes by Liposome Rupture Impact Voltammetry," *Anal. Chem.* 89(21):11753-11757 (2017).
Nischan et al., "Site-specific PEGylation of proteins: Recent developments," Journal of Organic Chemistry, 79(22):10727-10733 (2014).
Oren et al., "Selective lysis of bacteria but not mammalian cells by diastereomers of melittin: structure-function study," *Biochemistry* 36(7):1826-1835 (1997).
Oshima et al. "cDNA clones of Japanese hepatitis C virus genomes derived from a single patient show sequence heterogeneity." *J Gen Virol.* ( Pt 11):2805-9 (1991).
Papo et al., "Can we predict biological activity of antimicrobial peptides from their interactions with model phospholipid membranes? ," *Peptides* 24(11):1693-1703 (2003).
Papo et al., "The Consequence of Sequence Alteration of an Amphipathic α-Helical Antimicrobial Peptide and Its Diastereomers," *J. Biol. Chem.* 277(37):33913-33921 (2002).
Patent Cooperation Treaty Written Opinion of the International Searching Authority for International Application No. PCT/SG2016/050291, dated Aug. 8, 2016 (6 pages).
Rabkin et al., "The ProteOn™ HTG Sensor Chip: Novel Surface for Stable Capture of Histidine-Tagged Proteins for Protein-Protein Interaction Analysis," Bio-Rad Laboratories, Inc., Bulletin 6132 (2012), 8 pages.
Rathinakumar et al., "Biomolecular Engineering by Combinatorial Design and High-Throughput Screening: Small, Soluble Peptides that Permeabilize Membranes," *J. Am. Chem. Soc.* 130:9849-9858 (2008).
Rathinakumar et al., "Broad-spectrum antimicrobial peptides by rational combinatorial design and high-throughput screening: the importance of interfacial activity," *J. Am. Chem. Soc.* 131(22):7609-7617 (2009).
Roberts et al., "Chemistry for peptide and protein PEGylation," *Adv. Drug Deliv. Rev.* 64:116-127 (2012).
Sirohi et al., "The 3.8 Å resolution cryo-EM structure of Zika virus," *Science* 352:467-470 (2016).
St. Vincent et al., "Rigid amphipathic fusion inhibitors, small molecule antiviral compounds against enveloped viruses," *Proc. Natl. Acad. Sci. U.S.A.* 107(40):17339-17344 (2010).
Sun et al., "Enantiomeric Effect of d-Amino Acid Substitution on the Mechanism of Action of α-Helical Membrane-Active Peptides," *Int. J. Mol. Sci.* 19(1):pii: E67 (2017).
Tabaei et al., "Single vesicle analysis reveals nanoscale membrane curvature selective pore formation in lipid membranes by an antiviral α-helical peptide," *Nano Lett.* 12:5719-5725 (2012).
Takamizawa et al., "Structure and organization of the hepatitis C virus genome isolated from human carriers," *J Virol.* 65(3):1105-13 (1991).
Teixeira et al., "Role of lipids in the interaction of antimicrobial peptides with membranes," *Prog. Lipid Res.* 51(2):149-177 (2012).
Veazey et al., "C5A Protects Macaques from Vaginal Simian-Human Immunodeficiency Virus Challenge," *Antimicrob. Agents Chemother.* 60(1):693-698 (2016).
Vigant et al., "Broad-spectrum antivirals against viral fusion," *Nat. Rev. Microbiol.* 13(7):426-437 (2015).
Wang et al., "Flavivirus Entry Inhibitors," *ACS Infect. Dis.* 1(9):428-434 (2015).
Ward et al., "Peptide lipidation stabilizes structure to enhance biological function," *Mol. Metab.* 2(4):468-479 (2013).
Warfield et al., "Inhibition of endoplasmic reticulum glucosidases is required for in vitro and in vivo dengue antiviral activity by the iminosugar uv-4," *Antiviral Res.* 129:93-98 (2016).
Wimley et al., "Antimicrobial peptides: successes, challenges and unanswered questions," *J. Membr. Biol.* 239(1-2):27-34 (2011).
Wiradharma et al., "Branched and 4-arm starlike a-helical peptide structures with enhanced antimicrobial potency and selectivity," *Small* 8(3):362-366 (2012).
Wolf et al., "A broad-spectrum antiviral targeting entry of enveloped viruses," *Proc. Natl. Acad. Sci. U.S.A.* 107(7):3157-3162 (2010).
Yan et al., "A new natural α-helical peptide from the venom of the scorpion Heterometrus petersii kills HCV," *Peptides* 32(1):11-19 (2011) (Epub Oct. 13, 2010).
Zan et al., "AH Peptide-mediated formation of charged planar lipid bilayers," *J. Phys. Chem. B.* 118(13):3616-3621 (2014).
Zhang and Bulaj, "Converting peptides into drug leads by lipidation," *Curr. Med. Chem.* 19(11):1602-1618 (2012).

\* cited by examiner

```
                         SEQUENCE LISTING

<160> NUMBER OF SEQ ID NOS: 40

<210> SEQ ID NO 1
<211> LENGTH: 16
<212> TYPE: PRT
<213> ORGANISM: Artificial Sequence
<220> FEATURE:
<223> OTHER INFORMATION: Anti-infective peptides - TSG001

<400> SEQUENCE: 1

Ser Gly Ser Trp Leu Arg Asp Val Trp Thr Trp Leu Gln Ser Lys Leu
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Anti-infective peptides - TSG002

<400> SEQUENCE: 2

Gly Ser Ser Trp Leu Arg Asp Val Trp Thr Trp Leu Gln Ser Lys Leu
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Anti-infective peptides - TSG003

<400> SEQUENCE: 3

Gly Ser Ser Trp Leu Arg Asp Val Trp Thr Trp Leu Gln Ser Ala Leu
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Anti-infective peptides - TSG004

<400> SEQUENCE: 4

Gly Ser Ser Trp Leu Arg Asp Val Trp Thr Lys Leu Gln Ser Trp Leu
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Anti-infective peptides - TSG005

<400> SEQUENCE: 5

Gly Ser Ser Trp Leu Arg Asp Ile Trp Thr Lys Leu Gln Ser Trp Leu
1               5                   10                  15

<210> SEQ ID NO 6
<211> LENGTH: 16
<212> TYPE: PRT
<213> ORGANISM: Artificial Sequence
<220> FEATURE:
```

-continued

<223> OTHER INFORMATION: Anti-infective peptides - TSG006

<400> SEQUENCE: 6

Gly Ser Ser Trp Leu Arg Asp Ile Trp Thr Ala Leu Gln Ser Trp Leu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Anti-infective peptide - TSG007

<400> SEQUENCE: 7

Gly Ser Ser Trp Leu Arg Asp Ile Leu Thr Ala Leu Gln Ser Leu Leu
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Anti-infective peptide - TSG008

<400> SEQUENCE: 8

Ala Gly Ser Trp Leu Arg Asp Ile Trp Thr Trp Leu Gln Ser Ala Leu
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Anti-infective peptide - TSG009

<400> SEQUENCE: 9

Ala Gly Ser Trp Leu Arg Asp Ile Leu Thr Leu Leu Gln Ser Ala Leu
1               5                   10                  15

<210> SEQ ID NO 10
<211> LENGTH: 27
<212> TYPE: PRT
<213> ORGANISM: Artificial Sequence
<220> FEATURE:
<223> OTHER INFORMATION: AH peptide

<400> SEQUENCE: 10

Ser Gly Ser Trp Leu Arg Asp Val Trp Asp Trp Ile Cys Thr Val Leu
1               5                   10                  15
Thr Asp Phe Lys Thr Trp Leu Gln Ser Lys Leu
            20                  25

<210> SEQ ID NO 11
<211> LENGTH: 18
<212> TYPE: PRT
<213> ORGANISM: Artificial Sequence
<220> FEATURE:
<223> OTHER INFORMATION: C5A peptide

<400> SEQUENCE: 11

Ser Trp Leu Arg Asp Ile Trp Asp Trp Ile Cys Glu Val Leu Ser Asp
1               5                   10                  15
Phe Lys

<210> SEQ ID NO 12

```
-continued

<211> LENGTH: 16
<212> TYPE: PRT
<213> ORGANISM: Artificial Sequence
<220> FEATURE:
<223> OTHER INFORMATION: Anti-infective peptides consensus sequence
<220> FEATURE:
<221> NAME/KEY: misc_feature
<222> LOCATION: (1)..(2)
<223> OTHER INFORMATION: Xaa = Ser, Gly or Ala
<220> FEATURE:
<221> NAME/KEY: misc_feature
<222> LOCATION: (1)..(2)
<223> OTHER INFORMATION: Xaa = Ser or Gly
<220> FEATURE:
<221> NAME/KEY: misc_feature
<222> LOCATION: (8)..(8)
<223> OTHER INFORMATION: Xaa = Val or Ile
<220> FEATURE:
<221> NAME/KEY: misc_feature
<222> LOCATION: (9)..(9)
<223> OTHER INFORMATION: Xaa = Trp or Leu
<220> FEATURE:
<221> NAME/KEY: misc_feature
<222> LOCATION: (11)..(11)
<223> OTHER INFORMATION: Xaa = Trp, Lys, Ala or Leu
<220> FEATURE:
<221> NAME/KEY: misc_feature
<222> LOCATION: (15)..(15)
<223> OTHER INFORMATION: Xaa = Trp, Lys, Leu or Ala

<400> SEQUENCE: 12

Xaa Xaa Ser Trp Leu Arg Asp Xaa Xaa Thr Xaa Leu Gln Ser Xaa Leu
 1               5                  10                  15

<210> SEQ ID NO 13
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ser or Gly
<220> FEATURE:
<221> NAME/KEY: misc_feature
<222> LOCATION: (8)..(8)
<223> OTHER INFORMATION: Xaa = Val
<220> FEATURE:
<221> NAME/KEY: misc_feature
<222> LOCATION: (9)..(9)
<223> OTHER INFORMATION: Xaa = Trp
<220> FEATURE:
<221> NAME/KEY: misc_feature
<222> LOCATION: (11)..(11)
<223> OTHER INFORMATION: Xaa = Trp or Lys
<220> FEATURE:
<221> NAME/KEY: misc_feature
<222> LOCATION: (15)..(15)
<223> OTHER INFORMATION: Xaa = Trp, Lys or Ala

<400> SEQUENCE: 13

Xaa Xaa Ser Trp Leu Arg Asp Xaa Xaa Thr Xaa Leu Gln Ser Xaa Leu
 1               5                  10                  15

<210> SEQ ID NO 14
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ser or Gly
```

```
<220> FEATURE:
<221> NAME/KEY: misc_feature
<222> LOCATION: (8)..(8)
<223> OTHER INFORMATION: Xaa = Val
<220> FEATURE:
<221> NAME/KEY: misc_feature
<222> LOCATION: (9)..(9)
<223> OTHER INFORMATION: Xaa = Trp
<220> FEATURE:
<221> NAME/KEY: misc_feature
<222> LOCATION: (11)..(11)
<223> OTHER INFORMATION: Xaa = Trp
<220> FEATURE:
<221> NAME/KEY: misc_feature
<222> LOCATION: (15)..(15)
<223> OTHER INFORMATION: Xaa = Lys or Ala

<400> SEQUENCE: 14

Xaa Xaa Ser Trp Leu Arg Asp Xaa Xaa Thr Xaa Leu Gln Ser Xaa Leu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ser or Gly
<220> FEATURE:
<221> NAME/KEY: misc_feature
<222> LOCATION: (8)..(8)
<223> OTHER INFORMATION: Xaa = Val or Ile
<220> FEATURE:
<221> NAME/KEY: misc_feature
<222> LOCATION: (9)..(9)
<223> OTHER INFORMATION: Xaa = Trp
<220> FEATURE:
<221> NAME/KEY: misc_feature
<222> LOCATION: (11)..(11)
<223> OTHER INFORMATION: Xaa = Trp or Ala
<220> FEATURE:
<221> NAME/KEY: misc_feature
<222> LOCATION: (15)..(15)
<223> OTHER INFORMATION: Xaa = Trp or Lys

<400> SEQUENCE: 15

Xaa Xaa Ser Trp Leu Arg Asp Xaa Xaa Thr Xaa Leu Gln Ser Xaa Leu
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ser or Gly
<220> FEATURE:
<221> NAME/KEY: misc_feature
<222> LOCATION: (8)..(8)
<223> OTHER INFORMATION: Xaa = Val or Ile
<220> FEATURE:
<221> NAME/KEY: misc_feature
<222> LOCATION: (9)..(9)
<223> OTHER INFORMATION: Xaa = Trp
<220> FEATURE:
<221> NAME/KEY: misc_feature
<222> LOCATION: (11)..(11)
<223> OTHER INFORMATION: Xaa = Trp, Lys or Ala
<220> FEATURE:
```

```
<221> NAME/KEY: misc_feature
<222> LOCATION: (15)..(15)
<223> OTHER INFORMATION: Xaa = Trp, Lys or Ala

<400> SEQUENCE: 16

Xaa Xaa Ser Trp Leu Arg Asp Xaa Xaa Thr Xaa Leu Gln Ser Xaa Leu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ser or Gly
<220> FEATURE:
<221> NAME/KEY: misc_feature
<222> LOCATION: (8)..(8)
<223> OTHER INFORMATION: Xaa = Val or Ile
<220> FEATURE:
<221> NAME/KEY: misc_feature
<222> LOCATION: (9)..(9)
<223> OTHER INFORMATION: Xaa = Trp
<220> FEATURE:
<221> NAME/KEY: misc_feature
<222> LOCATION: (11)..(11)
<223> OTHER INFORMATION: Xaa = Trp or Ala
<220> FEATURE:
<221> NAME/KEY: misc_feature
<222> LOCATION: (15)..(15)
<223> OTHER INFORMATION: Xaa = Trp, Lys or Ala

<400> SEQUENCE: 17

Xaa Xaa Ser Trp Leu Arg Asp Xaa Xaa Thr Xaa Leu Gln Ser Xaa Leu
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Gly, Pro or Ala
<220> FEATURE:
<221> NAME/KEY: misc_feature
<222> LOCATION: (8)..(8)
<223> OTHER INFORMATION: Xaa = Val, Ile, Leu or Met
<220> FEATURE:
<221> NAME/KEY: misc_feature
<222> LOCATION: (9)..(9)
<223> OTHER INFORMATION: Xaa = Trp, Phe, Tyr or His
<220> FEATURE:
<221> NAME/KEY: misc_feature
<222> LOCATION: (11)..(11)
<223> OTHER INFORMATION: Xaa = Ala, Ser, Gly or Thr
<220> FEATURE:
<221> NAME/KEY: misc_feature
<222> LOCATION: (15)..(15)
<223> OTHER INFORMATION: Xaa = Trp, Tyr or Phe

<400> SEQUENCE: 18

Xaa Xaa Ser Trp Leu Arg Asp Xaa Xaa Thr Xaa Leu Gln Ser Xaa Leu
1               5                   10                  15

<210> SEQ ID NO 19
<211> LENGTH: 16
<212> TYPE: PRT
```

```
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ser or Gly
<220> FEATURE:
<221> NAME/KEY: misc_feature
<222> LOCATION: (8)..(8)
<223> OTHER INFORMATION: Xaa = Val or Ile
<220> FEATURE:
<221> NAME/KEY: misc_feature
<222> LOCATION: (9)..(9)
<223> OTHER INFORMATION: Xaa = Trp
<220> FEATURE:
<221> NAME/KEY: misc_feature
<222> LOCATION: (11)..(11)
<223> OTHER INFORMATION: Xaa = Trp, Lys or Ala
<220> FEATURE:
<221> NAME/KEY: misc_feature
<222> LOCATION: (15)..(15)
<223> OTHER INFORMATION: Xaa = Trp or Lys

<400> SEQUENCE: 19

Xaa Xaa Ser Trp Leu Arg Asp Xaa Xaa Thr Xaa Leu Gln Ser Xaa Leu
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: C-teminal of C5A peptide

<400> SEQUENCE: 20

Thr Trp Leu Gln Ser Lys Leu
1               5

<210> SEQ ID NO 21
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa is small amino acid
<220> FEATURE:
<221> NAME/KEY: misc_feature
<222> LOCATION: (8)..(8)
<223> OTHER INFORMATION: Xaa is hydrophobic amino acid with an
      aliphatic side chain
<220> FEATURE:
<221> NAME/KEY: misc_feature
<222> LOCATION: (9)..(9)
<223> OTHER INFORMATION: Xaa is hydrophobic amino acid
<220> FEATURE:
<221> NAME/KEY: misc_feature
<222> LOCATION: (11)..(11)
<223> OTHER INFORMATION: Xaa is hydrophilic amino acid or polar amino
      acid
<220> FEATURE:
<221> NAME/KEY: misc_feature
<222> LOCATION: (15)..(15)
<223> OTHER INFORMATION: Xaa is hydrophilic amino acid or polar amino
      acid

<400> SEQUENCE: 21

Xaa Xaa Ser Trp Leu Arg Asp Xaa Xaa Thr Xaa Leu Gln Ser Xaa Leu
1               5                   10                  15
```

-continued

```
<210> SEQ ID NO 22
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa is small amino acid
<220> FEATURE:
<221> NAME/KEY: misc_feature
<222> LOCATION: (8)..(8)
<223> OTHER INFORMATION: Xaa is hydrophobic amino acid with an
      aliphatic side chain
<220> FEATURE:
<221> NAME/KEY: misc_feature
<222> LOCATION: (9)..(9)
<223> OTHER INFORMATION: Xaa is hydrophobic amino acid
<220> FEATURE:
<221> NAME/KEY: misc_feature
<222> LOCATION: (11)..(11)
<223> OTHER INFORMATION: Xaa is hydrophilic amino acid
<220> FEATURE:
<221> NAME/KEY: misc_feature
<222> LOCATION: (15)..(15)
<223> OTHER INFORMATION: Xaa is hydrophilic amino acid

<400> SEQUENCE: 22

Xaa Xaa Ser Trp Leu Arg Asp Xaa Xaa Thr Xaa Leu Gln Ser Xaa Leu
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa is small amino acid
<220> FEATURE:
<221> NAME/KEY: misc_feature
<222> LOCATION: (8)..(8)
<223> OTHER INFORMATION: Xaa is hydrophobic amino acid with an
      aliphatic side chain
<220> FEATURE:
<221> NAME/KEY: misc_feature
<222> LOCATION: (9)..(9)
<223> OTHER INFORMATION: Xaa is hydrophobic amino acid
<220> FEATURE:
<221> NAME/KEY: misc_feature
<222> LOCATION: (11)..(11)
<223> OTHER INFORMATION: Xaa is polar amino acid
<220> FEATURE:
<221> NAME/KEY: misc_feature
<222> LOCATION: (15)..(15)
<223> OTHER INFORMATION: Xaa is polar amino acid

<400> SEQUENCE: 23

Xaa Xaa Ser Trp Leu Arg Asp Xaa Xaa Thr Xaa Leu Gln Ser Xaa Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa is small amino acid
<220> FEATURE:
```

```
<221> NAME/KEY: misc_feature
<222> LOCATION: (8)..(8)
<223> OTHER INFORMATION: Xaa is hydrophobic amino acid with an
      aliphatic side chain
<220> FEATURE:
<221> NAME/KEY: misc_feature
<222> LOCATION: (9)..(9)
<223> OTHER INFORMATION: Xaa is hydrophobic amino acid
<220> FEATURE:
<221> NAME/KEY: misc_feature
<222> LOCATION: (11)..(11)
<223> OTHER INFORMATION: Xaa is hydrophilic amino acid
<220> FEATURE:
<221> NAME/KEY: misc_feature
<222> LOCATION: (15)..(15)
<223> OTHER INFORMATION: Xaa is polar amino acid

<400> SEQUENCE: 24

Xaa Xaa Ser Trp Leu Arg Asp Xaa Xaa Thr Xaa Leu Gln Ser Xaa Leu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa is small amino acid
<220> FEATURE:
<221> NAME/KEY: misc_feature
<222> LOCATION: (8)..(8)
<223> OTHER INFORMATION: Xaa is hydrophobic amino acid with an
      aliphatic side chain
<220> FEATURE:
<221> NAME/KEY: misc_feature
<222> LOCATION: (9)..(9)
<223> OTHER INFORMATION: Xaa is hydrophobic amino acid
<220> FEATURE:
<221> NAME/KEY: misc_feature
<222> LOCATION: (11)..(11)
<223> OTHER INFORMATION: Xaa is polar amino acid
<220> FEATURE:
<221> NAME/KEY: misc_feature
<222> LOCATION: (15)..(15)
<223> OTHER INFORMATION: Xaa is hydrophilic amino acid

<400> SEQUENCE: 25

Xaa Xaa Ser Trp Leu Arg Asp Xaa Xaa Thr Xaa Leu Gln Ser Xaa Leu
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa is conservative amino acid substitution
      for serine, glycine or alanine
<220> FEATURE:
<221> NAME/KEY: misc_feature
<222> LOCATION: (8)..(8)
<223> OTHER INFORMATION: Xaa is conservative amino acid substitution
      for valine or isoleucine
<220> FEATURE:
<221> NAME/KEY: misc_feature
<222> LOCATION: (9)..(9)
<223> OTHER INFORMATION: Xaa is conservative amino acid substitution
      for tryptophan or leucine
<220> FEATURE:
```

```
<221> NAME/KEY: misc_feature
<222> LOCATION: (11)..(11)
<223> OTHER INFORMATION: Xaa is conservative amino acid substitution
      for tryptophan, lysine, alanine or leucine
<220> FEATURE:
<221> NAME/KEY: misc_feature
<222> LOCATION: (15)..(15)
<223> OTHER INFORMATION: Xaa is conservative amino acid substitution
      for tryptophan, lysine, alanine or leucine

<400> SEQUENCE: 26

Xaa Xaa Ser Trp Leu Arg Asp Xaa Xaa Thr Xaa Leu Gln Ser Xaa Leu
1               5                  10                  15

<210> SEQ ID NO 27
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ala, Cys, Gly, Pro, Ser or Thr
<220> FEATURE:
<221> NAME/KEY: misc_feature
<222> LOCATION: (8)..(8)
<223> OTHER INFORMATION: Xaa = Ala, Ile, Leu, Pro or Val
<220> FEATURE:
<221> NAME/KEY: misc_feature
<222> LOCATION: (9)..(9)
<223> OTHER INFORMATION: Xaa = Trp, Phe, Tyr, His, Ala, Ile, Leu, Pro
      or Val
<220> FEATURE:
<221> NAME/KEY: misc_feature
<222> LOCATION: (11)..(11)
<223> OTHER INFORMATION: Xaa = Trp, Phe, Tyr or His
<220> FEATURE:
<221> NAME/KEY: misc_feature
<222> LOCATION: (15)..(15)
<223> OTHER INFORMATION: Xaa = Trp, Phe, Tyr or His

<400> SEQUENCE: 27

Xaa Xaa Ser Trp Leu Arg Asp Xaa Xaa Thr Xaa Leu Gln Ser Xaa Leu
1               5                  10                  15

<210> SEQ ID NO 28
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ala, Cys, Gly, Pro, Ser or Thr
<220> FEATURE:
<221> NAME/KEY: misc_feature
<222> LOCATION: (8)..(8)
<223> OTHER INFORMATION: Xaa = Ala, Ile, Leu, Pro or Val
<220> FEATURE:
<221> NAME/KEY: misc_feature
<222> LOCATION: (9)..(9)
<223> OTHER INFORMATION: Xaa = Trp, Phe, Tyr, His, Ala, Ile, Leu, Pro
      or Val
<220> FEATURE:
<221> NAME/KEY: misc_feature
<222> LOCATION: (11)..(11)
<223> OTHER INFORMATION: Xaa = Trp, Phe, Tyr or His
<220> FEATURE:
<221> NAME/KEY: misc_feature
<222> LOCATION: (15)..(15)
<223> OTHER INFORMATION: Xaa = Lys, Tyr, Arg, His, Asn, Gln, Ser or Thr

<400> SEQUENCE: 28
```

```
Xaa Xaa Ser Trp Leu Arg Asp Xaa Xaa Thr Xaa Leu Gln Ser Xaa Leu
1               5                   10                  15
```

<210> SEQ ID NO 29
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ala, Cys, Gly, Pro, Ser or Thr
<220> FEATURE:
<221> NAME/KEY: misc_feature
<222> LOCATION: (8)..(8)
<223> OTHER INFORMATION: Xaa = Ala, Ile, Leu, Pro or Val
<220> FEATURE:
<221> NAME/KEY: misc_feature
<222> LOCATION: (9)..(9)
<223> OTHER INFORMATION: Xaa = Trp, Phe, Tyr, His, Ala, Ile, Leu, Pro
      or Val
<220> FEATURE:
<221> NAME/KEY: misc_feature
<222> LOCATION: (11)..(11)
<223> OTHER INFORMATION: Xaa = Trp, Phe, Tyr or His
<220> FEATURE:
<221> NAME/KEY: misc_feature
<222> LOCATION: (15)..(15)
<223> OTHER INFORMATION: Xaa = Ala, Cys, Gly, Pro, Ser, Ile, Leu, Val
      or Thr

<400> SEQUENCE: 29

```
Xaa Xaa Ser Trp Leu Arg Asp Xaa Xaa Thr Xaa Leu Gln Ser Xaa Leu
1               5                   10                  15
```

<210> SEQ ID NO 30
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ala, Cys, Gly, Pro, Ser or Thr
<220> FEATURE:
<221> NAME/KEY: misc_feature
<222> LOCATION: (8)..(8)
<223> OTHER INFORMATION: Xaa = Ala, Ile, Leu, Pro or Val
<220> FEATURE:
<221> NAME/KEY: misc_feature
<222> LOCATION: (9)..(9)
<223> OTHER INFORMATION: Xaa = Trp, Phe, Tyr, His, Ala, Ile, Leu, Pro
      or Val
<220> FEATURE:
<221> NAME/KEY: misc_feature
<222> LOCATION: (11)..(11)
<223> OTHER INFORMATION: Xaa = Lys, Tyr, Arg, His, Asn, Gln, Ser or Thr
<220> FEATURE:
<221> NAME/KEY: misc_feature
<222> LOCATION: (15)..(15)
<223> OTHER INFORMATION: Xaa = Trp, Phe, Tyr or His

<400> SEQUENCE: 30

```
Xaa Xaa Ser Trp Leu Arg Asp Xaa Xaa Thr Xaa Leu Gln Ser Xaa Leu
1               5                   10                  15
```

<210> SEQ ID NO 31
<211> LENGTH: 16
<212> TYPE: PRT
<213> ORGANISM: Artificial Sequence
<220> FEATURE:

```
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ala, Cys, Gly, Pro, Ser or Thr
<220> FEATURE:
<221> NAME/KEY: misc_feature
<222> LOCATION: (8)..(8)
<223> OTHER INFORMATION: Xaa = Ala, Ile, Leu, Pro or Val
<220> FEATURE:
<221> NAME/KEY: misc_feature
<222> LOCATION: (9)..(9)
<223> OTHER INFORMATION: Xaa = Trp, Phe, Tyr, His, Ala, Ile, Leu, Pro
      or Val
<220> FEATURE:
<221> NAME/KEY: misc_feature
<222> LOCATION: (11)..(11)
<223> OTHER INFORMATION: Xaa = Lys, Tyr, Arg, His, Asn, Gln, Ser or Thr
<220> FEATURE:
<221> NAME/KEY: misc_feature
<222> LOCATION: (15)..(15)
<223> OTHER INFORMATION: Xaa = Lys, Tyr, Arg, His, Asn, Gln, Ser or Thr

<400> SEQUENCE: 31

Xaa Xaa Ser Trp Leu Arg Asp Xaa Xaa Thr Xaa Leu Gln Ser Xaa Leu
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ala, Cys, Gly, Pro, Ser or Thr
<220> FEATURE:
<221> NAME/KEY: misc_feature
<222> LOCATION: (8)..(8)
<223> OTHER INFORMATION: Xaa = Ala, Ile, Leu, Pro or Val
<220> FEATURE:
<221> NAME/KEY: misc_feature
<222> LOCATION: (9)..(9)
<223> OTHER INFORMATION: Xaa = Trp, Phe, Tyr, His, Ala, Ile, Leu, Pro
      or Val
<220> FEATURE:
<221> NAME/KEY: misc_feature
<222> LOCATION: (11)..(11)
<223> OTHER INFORMATION: Xaa = Lys, Tyr, Arg, His, Asn, Gln, Ser or Thr
<220> FEATURE:
<221> NAME/KEY: misc_feature
<222> LOCATION: (15)..(15)
<223> OTHER INFORMATION: Xaa = Ala, Cys, Gly, Pro, Ser, Ile, Leu, Val
      or Thr

<400> SEQUENCE: 32

Xaa Xaa Ser Trp Leu Arg Asp Xaa Xaa Thr Xaa Leu Gln Ser Xaa Leu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ala, Cys, Gly, Pro, Ser or Thr
<220> FEATURE:
<221> NAME/KEY: misc_feature
<222> LOCATION: (8)..(8)
<223> OTHER INFORMATION: Xaa = Ala, Ile, Leu, Pro or Val
<220> FEATURE:
```

```
<221> NAME/KEY: misc_feature
<222> LOCATION: (9)..(9)
<223> OTHER INFORMATION: Xaa = Trp, Phe, Tyr, His, Ala, Ile, Leu, Pro
      or Val
<220> FEATURE:
<221> NAME/KEY: misc_feature
<222> LOCATION: (11)..(11)
<223> OTHER INFORMATION: Xaa = Ala, Cys, Gly, Pro, Ser, Ile, Leu, Val
      or Thr
<220> FEATURE:
<221> NAME/KEY: misc_feature
<222> LOCATION: (15)..(15)
<223> OTHER INFORMATION: Xaa = Trp, Phe, Tyr or His

<400> SEQUENCE: 33

Xaa Xaa Ser Trp Leu Arg Asp Xaa Xaa Thr Xaa Leu Gln Ser Xaa Leu
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ala, Cys, Gly, Pro, Ser or Thr
<220> FEATURE:
<221> NAME/KEY: misc_feature
<222> LOCATION: (8)..(8)
<223> OTHER INFORMATION: Xaa = Ala, Ile, Leu, Pro or Val
<220> FEATURE:
<221> NAME/KEY: misc_feature
<222> LOCATION: (9)..(9)
<223> OTHER INFORMATION: Xaa = Trp, Phe, Tyr, His, Ala, Ile, Leu, Pro
      or Val
<220> FEATURE:
<221> NAME/KEY: misc_feature
<222> LOCATION: (11)..(11)
<223> OTHER INFORMATION: Xaa = Ala, Cys, Gly, Pro, Ser, Ile, Leu, Val
      or Thr
<220> FEATURE:
<221> NAME/KEY: misc_feature
<222> LOCATION: (15)..(15)
<223> OTHER INFORMATION: Xaa = Lys, Tyr, Trp, Arg, His, Asn, Gln, Ser
      or Thr

<400> SEQUENCE: 34

Xaa Xaa Ser Trp Leu Arg Asp Xaa Xaa Thr Xaa Leu Gln Ser Xaa Leu
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Ala, Cys, Gly, Pro, Ser or Thr
<220> FEATURE:
<221> NAME/KEY: misc_feature
<222> LOCATION: (8)..(8)
<223> OTHER INFORMATION: Xaa = Ala, Ile, Leu, Pro or Val
<220> FEATURE:
<221> NAME/KEY: misc_feature
<222> LOCATION: (9)..(9)
<223> OTHER INFORMATION: Xaa = Trp, Phe, Tyr, His, Ala, Ile, Leu, Pro
      or Val
<220> FEATURE:
<221> NAME/KEY: misc_feature
<222> LOCATION: (11)..(11)
<223> OTHER INFORMATION: Xaa = Ala, Cys, Gly, Pro, Ser, Ile, Leu, Val
```

```
      or Thr
<220> FEATURE:
<221> NAME/KEY: misc_feature
<222> LOCATION: (15)..(15)
<223> OTHER INFORMATION: Xaa = Ala, Cys, Gly, Pro, Ser, Ile, Leu, Val
      or Thr

<400> SEQUENCE: 35

Xaa Xaa Ser Trp Leu Arg Asp Xaa Xaa Thr Xaa Leu Gln Ser Xaa Leu
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Gly, Pro or Ala
<220> FEATURE:
<221> NAME/KEY: misc_feature
<222> LOCATION: (8)..(8)
<223> OTHER INFORMATION: Xaa = Val, Ile, Leu or Met
<220> FEATURE:
<221> NAME/KEY: misc_feature
<222> LOCATION: (9)..(9)
<223> OTHER INFORMATION: Xaa = Trp, Phe, Tyr or His
<220> FEATURE:
<221> NAME/KEY: misc_feature
<222> LOCATION: (11)..(11)
<223> OTHER INFORMATION: Xaa = Trp, Tyr or Phe
<220> FEATURE:
<221> NAME/KEY: misc_feature
<222> LOCATION: (15)..(15)
<223> OTHER INFORMATION: Xaa = Lys, Arg, Gln, Glu or Asn

<400> SEQUENCE: 36

Xaa Xaa Ser Trp Leu Arg Asp Xaa Xaa Thr Xaa Leu Gln Ser Xaa Leu
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(1)
<223> OTHER INFORMATION: Xaa = Ser, Thr, Ala or Gln
<220> FEATURE:
<221> NAME/KEY: misc_feature
<222> LOCATION: (2)..(2)
<223> OTHER INFORMATION: Xaa = Gly, Pro or Ala
<220> FEATURE:
<221> NAME/KEY: misc_feature
<222> LOCATION: (8)..(8)
<223> OTHER INFORMATION: Xaa = Val, Ile, Leu or Met
<220> FEATURE:
<221> NAME/KEY: misc_feature
<222> LOCATION: (9)..(9)
<223> OTHER INFORMATION: Xaa = Trp, Phe, Tyr or His
<220> FEATURE:
<221> NAME/KEY: misc_feature
<222> LOCATION: (11)..(11)
<223> OTHER INFORMATION: Xaa = Trp, Tyr or Phe
<220> FEATURE:
<221> NAME/KEY: misc_feature
<222> LOCATION: (15)..(15)
<223> OTHER INFORMATION: Xaa = Lys, Arg, Gln, Glu or Asn

<400> SEQUENCE: 37
```

```
Xaa Xaa Ser Trp Leu Arg Asp Xaa Xaa Thr Xaa Leu Gln Ser Xaa Leu
1               5                   10                  15
```

```
<210> SEQ ID NO 38
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(2)
<223> OTHER INFORMATION: Xaa = Gly, Pro or Ala
<220> FEATURE:
<221> NAME/KEY: misc_feature
<222> LOCATION: (8)..(8)
<223> OTHER INFORMATION: Xaa = Val, Ile, Leu or Met
<220> FEATURE:
<221> NAME/KEY: misc_feature
<222> LOCATION: (9)..(9)
<223> OTHER INFORMATION: Xaa = Trp, Phe, Tyr or His
<220> FEATURE:
<221> NAME/KEY: misc_feature
<222> LOCATION: (11)..(11)
<223> OTHER INFORMATION: Xaa = Lys, Arg, Gln, Glu or Asn
<220> FEATURE:
<221> NAME/KEY: misc_feature
<222> LOCATION: (15)..(15)
<223> OTHER INFORMATION: Xaa = Trp, Tyr or Phe

<400> SEQUENCE: 38

Xaa Xaa Ser Trp Leu Arg Asp Xaa Xaa Thr Xaa Leu Gln Ser Xaa Leu
1               5                   10                  15
```

```
<210> SEQ ID NO 39
<211> LENGTH: 16
<212> TYPE: PRT
<213> ORGANISM: Artificial Sequence
<220> FEATURE:
<223> OTHER INFORMATION: Anti-infective peptide consensus sequence
<220> FEATURE:
<221> NAME/KEY: misc_feature
<222> LOCATION: (1)..(1)
<223> OTHER INFORMATION: Xaa = Ser, Thr, Ala or Gln
<220> FEATURE:
<221> NAME/KEY: misc_feature
<222> LOCATION: (2)..(2)
<223> OTHER INFORMATION: Xaa = Gly, Pro or Ala
<220> FEATURE:
<221> NAME/KEY: misc_feature
<222> LOCATION: (8)..(8)
<223> OTHER INFORMATION: Xaa = Val, Ile, Leu or Met
<220> FEATURE:
<221> NAME/KEY: misc_feature
<222> LOCATION: (9)..(9)
<223> OTHER INFORMATION: Xaa = Trp, Phe, Tyr or His
<220> FEATURE:
<221> NAME/KEY: misc_feature
<222> LOCATION: (11)..(11)
<223> OTHER INFORMATION: Xaa = Lys, Arg, Gln, Glu or Asn
<220> FEATURE:
<221> NAME/KEY: misc_feature
<222> LOCATION: (15)..(15)
<223> OTHER INFORMATION: Xaa = Trp, Tyr or Phe

<400> SEQUENCE: 39

Xaa Xaa Ser Trp Leu Arg Asp Xaa Xaa Thr Xaa Leu Gln Ser Xaa Leu
1               5                   10                  15
```

```
<210> SEQ ID NO 40
<211> LENGTH: 16
<212> TYPE: PRT
<213> ORGANISM: Artificial Sequence
<220> FEATURE:
```

```
<223> OTHER INFORMATION: Anti-infective peptide consensus sequence
<220> FEATURE:
<221> NAME/KEY: misc_feature
<222> LOCATION: (1)..(1)
<223> OTHER INFORMATION: Xaa = Ser, Thr, Ala or Gln
<220> FEATURE:
<221> NAME/KEY: misc_feature
<222> LOCATION: (2)..(2)
<223> OTHER INFORMATION: Xaa = Gly, Pro or Ala
<220> FEATURE:
<221> NAME/KEY: misc_feature
<222> LOCATION: (8)..(8)
<223> OTHER INFORMATION: Xaa = Val, Ile, Leu or Met
<220> FEATURE:
<221> NAME/KEY: misc_feature
<222> LOCATION: (9)..(9)
<223> OTHER INFORMATION: Xaa = Trp, Phe, Tyr or His
<220> FEATURE:
<221> NAME/KEY: misc_feature
<222> LOCATION: (11)..(11)
<223> OTHER INFORMATION: Xaa = Ala, Ser, Gly or Thr
<220> FEATURE:
<221> NAME/KEY: misc_feature
<222> LOCATION: (15)..(15)
<223> OTHER INFORMATION: Xaa = Trp, Tyr or Phe

<400> SEQUENCE: 40

Xaa Xaa Ser Trp Leu Arg Asp Xaa Xaa Thr Xaa Leu Gln Ser Xaa Leu
1               5                   10                  15
```

BROAD-SPECTRUM ANTI-INFECTIVE PEPTIDES

This application is a continuation application of U.S. application Ser. No. 17/081,166, filed Oct. 27, 2020, which is a continuation application of Ser. No. 16/421,119, filed May 23, 2019, which is a continuation application of U.S. application Ser. No. 15/738,730, filed Dec. 21, 2017 (now U.S. Pat. No. 10,351,604), which is a national stage of International Patent Application No. PCT/SG2016/050291, filed on Jun. 24, 2016, which claims the benefit of U.S. Provisional Application No. 62/184,354, filed Jun. 25, 2015, each of which is incorporated herein by reference in its entirety.

Incorporated herein by reference is the Sequence Listing being concurrently submitted via EFS-Web as an ASCII text file named "14312-007-999_SEQ_LISTING.txt," created on Jun. 15, 2021 and having 23,812 bytes in size.

1. INTRODUCTION

Provided herein are anti-infective peptides and uses thereof. Such anti-infective peptides are useful against bacteria and viruses. Also provided herein are compositions comprising said anti-infective peptides.

2. BACKGROUND

Antibiotics are the most common drug class to treat bacterial infections and are a key part of the pharmaceutical industry. There are high annual expenses for antibiotics of more than US$10 billion in the United States. The global expenses are much greater than this estimate and most of these expenses are for outpatient drug prescriptions. There is significant prescription and over-prescription of antibiotics for many different kinds of illnesses. Sometimes, the cause of the illness may have a low chance to be bacterial but doctors want to be careful and still give antibiotics to patients. This high usage of antibiotics is a major public health problem because it creates drug-resistant bacteria. These are bacteria that cannot be killed by common antibiotics and they can cause serious infections that spread in the body. There is significant concern about bacterial resistance, especially multidrug-resistant bacterial strains that are called "super bacteria." The biggest issue is that infections caused by these drug-resistant bacteria cannot be treated by common antibiotics.

The market potential for treating drug-resistant bacterial infections is very large. Antibiotic-resistant bacterial strains are estimated to affect 2 million patients annually in the European Union, for example. In the United States, the cost of antibiotic resistance is more than US$20 billion per year and patients need an additional one to two weeks of hospital care. Among different antibiotic-resistant bacteria, methicillin-resistant *S. aureus* (MRSA) is well-known and has been identified as the leading cause of skin and soft-tissue infections, which include acute bacterial skin and skin structure infections (ABSSSIs). MRSA is easily transmitted through skin-to-skin contact. It also shows resistance towards many drugs that have been resurrected or developed as Gram-positive antibiotics. It is estimated that more than 53 million people worldwide are MRSA carriers. The annual cost of MRSA infections in USA alone is more than US$14 billion. While MRSA skin infections are merely one example, the numbers from this case alone support that there are significant human and economic costs from infections caused by multidrug-resistant bacterial strains.

It is important to note that the market need is unmet. The development of new antibiotics is a low priority for many companies because the treatment time is short and it is difficult to identify new classes of antibiotics. Between the 1960s and 2011, only four new classes of antibiotics were developed and marketed. At present, only four large pharmaceutical companies have active research and development programs to create new antibiotics. For comparison, in the 1980's, there were 20 large companies trying to develop new antibiotics. The drop in antibiotic research has three main reasons. It is difficult to find new classes of antibiotics because it was already significantly researched. There are also many generic antibiotics available over the counter and companies worry that these drugs create high competition that could decrease possible profits from a new antibiotic. It is very expensive and takes a long time to develop a new drug so that drug should have patent protection and fill a need that is unmet by generic antibiotics. In addition, it has been difficult to get new antibiotics approved by regulatory agencies, including the United States Food and Drug Administration (FDA).

Recently, there is more attention to the issue because the number of super bacteria is growing. The FDA created a new product category called the Qualified Infectious Disease Product (QIDP). Drugs in this category have a special designation from the FDA, which shortens the approval review process and increases the time (an additional 5 years) for exclusive marketing. These benefits are important because it means that new antibiotics can reach patients more quickly and there is more economic motivation for pharmaceutical companies to develop new antibiotics. One particular focus of need is on treating acute bacterial skin and skin structure infections, including regular and antibiotic-resistant strains. The current management for these infections is incision and drainage, and antibiotics may also be given if they can treat the bacterial infection. Because standard antibiotics are resistant, there are several other antibiotics that are used in such cases. Table 1 describes the antibiotics, including their mechanism and long-term challenges.

TABLE 1

Summary of Antibiotics Used to Treat MRSA Skin Infections.

| Drug | Status | Issue |
| --- | --- | --- |
| Vancomycin | Top choice antibiotic to treat MRSA patients in hospitals | Poor drug properties require intravenous administration |
| Trimethoprim-Sulfamethoxazole | Used by clinical doctors in MRSA treatments (with drainage) | No research supports effectiveness; does not improve clinical treatment outcomes |

TABLE 1-continued

Summary of Antibiotics Used to Treat MRSA Skin Infections.

| Drug | Status | Issue |
| --- | --- | --- |
| Clindamycin | Used by clinical doctors in MRSA treatments (with drainage) | No research supports effectiveness; does not improve clinical treatment outcomes |
| Mupirocin | Used as a topical antibiotic for MRSA treatment | Drug-resistant bacteria quickly emerge so cannot be used for a long time. |
| Fusidic Acid | Used as a topical antibiotic for MRSA treatment | Drug-resistant bacteria quickly emerge so cannot be used for a long time and in cocktails. |
| Finafloxacin | Approved in 2014 under QIDP designation | Approved for ear infections, member of fluoroquinoline class that have serious side effects and fast bacterial mutation |
| Dalvance (dalbavancin) | Approved in 2014 under QIDP designation | Is a second-generation Vancomyocin, and still requires intravenous administration. |
| Sivextro (tedizolid phosphate) | Approved in 2014 under QIDP designation | Member of oxazolidinone class, and antibiotic resistance has been reported. |
| Orbactiv (oritavancin) | Approved in 2014 under QIDP designation | Is a second-generation Vancomyocin, and still requires intravenous administration. |

As can be seen from these statistics, there are two major problems. There are a limited number of topical antibiotics, and all classes of antibiotics have problems with resistant strains quickly emerging. One alternative is antimicrobial peptides that are membrane-active but these peptides have not found wide application because they have relatively expensive production costs (due to lengthy amino acid sequences) and there were two failed clinical trials in the 90's which led already risk-averse pharmaceutical companies to stick with small molecule antibiotics. However, with the impending rise of drug-resistant bacteria, there is growing recognition of the need for new classes of antibiotics, and several classes of antibacterial peptides are now in early- and late-stage clinical trials. Of note, no membrane-active antibacterial peptide is currently under clinical development despite the promise of membrane interference to serve as the basis for long-term sustained therapies with high barriers to the emergence of drug-resistant bacterial strains.

The treatment of viruses faces similar challenges with the emergence and re-emergence of viruses fast eclipsing the rates at which new antiviral drugs can be developed. This gap has motivated the development of broad-spectrum antiviral drugs and the lipid bilayer of enveloped viruses is a key antiviral. Small molecules with membrane active behaviors targeting the virus envelope have largely indiscriminate activity, whereas antiviral peptides are more selective and have strong potential to form the basis of new antiviral therapies. Importantly, targeting the virus envelope is therapeutically attractive because there is a very high barrier to the development of drug-resistant virus strains. This is because the envelope is not encoded in the virus genome, but rather derived from host cells. Two antiviral peptides that target the virus envelope have been reported and can function as topical microbicides. However, these peptides completely lack antibacterial activity.

In order to motivate the clinical development of an anti-infective peptide, it is important to invent peptides that have broad-spectrum activity against both viruses and bacteria. In one preferred embodiment, to treat bacterial skin infections, an antibiotic with a topical formulation would be easy-to-use for patients and doctors. However, topical antibiotics have serious problems because bacteria can easily mutate. Other types of antibiotics used to treat MRSA skin infections require intravenous administration or have questionable efficacy. The market needs a new antibiotic that has long-term potential to address these problems. An ideal antibiotic would have i) a topical formulation; ii) a high barrier to mutations developing, iii) low side effects; iv) high efficacy; and v) a broad spectrum. With other proper suitable therapeutic properties, an antibiotic of this kind could be suitable for treating a wide range of bacterial, viral, and fungal infections in humans and animals through intravenous, intraperitoneal, subcutaneous, topical, oral, nasal, and other administration routes.

Zika Virus

An example of the growing need for anti-infective peptides is the ongoing Zika virus (ZIKV) epidemic, which has been declared a global public health emergency (Gulland, B M J 352, i657 (2016), Lucey and Gostin, JAMA 315, 865 (2016)). While ZIKV was discovered more than half a century ago, until recently, it was classified as a neglected tropical disease with limited geographical scope and few cases of human infection (Faye et al., PLoS Negl Trop Dis 8, e2636 (2014)). In 2007, more than 70% of the population on Micronesia's Yap Island became infected and it was the first episode of human infection outside of Africa or Asia (Duffy et al., New England Journal of Medicine 360, 2536 (2009)). In 2016, the global spread of ZIKV has reached epidemic levels across at least four continents and there is growing concern about the pathogenic clinical symptoms caused by circulating strains, including neurological damage such as Guillain-Barré syndrome (Cao-Lormeau et al., The Lancet, (2016)) and links between ZIKV infection and the rise of microcephaly among neonates (Mlakar et al., New England Journal of Medicine 374, 951 (2016)). Moreover, there are a number of possible transmission routes including mosquito vectors and human bloodborne and sexual transmission (Musso et al., Emerging Infectious Diseases 21, 359 (2015)). Given the accelerating pace of viral spread worldwide, the lack of countermeasures to prevent or blunt ZIKV infection is a major challenge, and there are currently no approved vaccines or therapies (Malone et al., PLoS Negl Trop Dis 10, e0004530 (2016)).

ZIKV is a member of the Flaviviridae family and is a mosquito-borne flavivirus related to the Dengue, Yellow Fever, Japanese Encephalitis and West Nile viruses (Chan et al., Journal of Infection, (2016)). Like other flaviviruses, ZIKV is an enveloped, positive strand RNA virus which possesses an approximately 11,000 base genome (Mukhopadhyay et al., Nature Reviews Microbiology 3, 13 (2005)).

The RNA genome is packaged together with capsid proteins, and is enclosed within an icosahedral shell consisting of envelope (E) glycoprotein, membrane (M) protein, and precursor membrane (prM) protein that are embedded in a lipid bilayer (Lindenbach et al., Flaviviridae, p 712-746. Fields Virology 1, (2013)). Flavivirus particles exist in three forms—immature (noninfectious), mature (infectious) or host membrane-bound states—and the maturation process involves a structural transformation from a spiky to smooth surface morphology. It has long been known that infectious ZIKV particles are spherical with around 40-55 nm diameter (Dick, Transactions of the Royal Society of Tropical Medicine and Hygiene 46, 521 (1952)).

Recently, using cryo-electron microscopy, Sirohi et al. showed that the structure of ZIKV particles is similar to those of other flaviviruses, while noting that the ZIKV E protein has a distinct, highly variable region near the fusion loop that may influence sensitivity to antibodies (Sirohi et al., Science 352, 467 (2016)). Furthermore, Kostyuchenko et al. reported structural similarities between ZIKV and other flaviviruses, and also identified that ZIKV particles exhibit particularly high thermal stability due to a compact structure (Kostyuchenko et al., Structure of the thermally stable Zika virus. Nature advance online publication, doi:10.1038/nature17994 (2016)). Given the high structural stability of ZIKV particles, it has been suggested that therapeutic drugs which destabilize ZIKV particles would be useful agents for reducing disease outcome or limiting viral spread (Kostyuchenko et al., Structure of the thermally stable Zika virus. Nature advance online publication, doi:10.1038/nature17994 (2016)). Indeed, Wang and Shi have also recommended the development of flavivirus entry inhibitors that directly interfere with virus particles (Wang, ACS Infectious Diseases 1, 428 (2015)).

Towards this goal, a flavivirus broadly neutralizing antibody was demonstrated to bind to the ZIKV E protein of immature virus particles and protect against ZIKV infection, although this protection may occur through a complement-dependent effector function (Dai et al., Cell Host & Microbe 19, 696 (2016)). It has also been reported that ZIKV in plasma samples could be inactivated by exposure to a combination of photosensitive amotosalen intercalating agent and ultraviolet A illumination (Aubry et al., Transfusion 56, 33 (2016)). However, the identification of an antiviral agent that destabilizes ZIKV particles in the context of preventing virus entry remains elusive, particularly one which is both therapeutically selective and broadly applicable. In this regard, disruption of the lipid membrane surrounding enveloped viruses is an emerging approach towards developing virus entry inhibitors, and there is strong motivation to identify membrane-active compounds that achieve this goal with high selectivity and potency (Vigant et al., Nature Reviews Microbiology 13, 426 (2015), Jackman et al., "Nanomedicine for Infectious Disease Applications: Innovation towards Broad—Spectrum Treatment of Viral Infections," Small 12, No. 9 (2016): 1133-1139, (2015)).

3. SUMMARY

In one aspect, provided herein are anti-infective peptides. In a specific embodiment, an anti-infective peptide described herein possesses broad spectrum antiviral activity as well as antibacterial activity, while exhibiting a low cytotoxicity against human cell lines and vaginal bacteria. In a particular embodiment, an anti-infective peptide described herein has a therapeutic index of greater than 10. In another specific embodiment, the anti-infective peptides are soluble in aqueous solutions.

In one embodiment, an anti-infective peptide described herein comprises, consists essentially of, or consists of a peptide set forth in Table 2A. In another embodiment, an anti-infective peptide is 16 to 26 amino acid residues in length and comprises the amino acid sequence of a peptide set forth in Table 2A. In another embodiment, an anti-infective peptide described herein comprises, consists essentially of, or consists of a peptide set forth in Table 2B. In another embodiment, an anti-infective peptide is 16 to 26 amino acid residues in length and comprises the amino acid sequence of a peptide set forth in Table 2B. In some embodiments, an anti-infective peptide described herein is pegylated or modified to include a hydrophilic polymer. In certain embodiments, an anti-infective peptide is stapled or lipidated. In some embodiments, an anti-infective peptide comprises D amino acids, L amino acids, or a combination thereof.

In another embodiment, an anti-infective peptide is 16 to 26 amino acid residues in length and comprises the following amino acid sequence: $X_1X_2SWLRDX_3X_4TX_5LQSX_6L$, wherein $X_1$ is S, G or A; $X_2$ is S or G; $X_3$ is V or I, $X_4$ is W or L; $X_5$ is W, K, A or L; and $X_6$ is W, K, L or A (SEQ ID NO:12). In another embodiment, an anti-infective peptide is 16 to 26 amino acid residues in length and comprises the following amino acid sequence: $X_1X_2SWLRDX_3X_4TX_5LQSX_6L$, wherein $X_1$ is S or G; $X_2$ is S or G; $X_3$ is V; $X_4$ is W; $X_5$ is W or K; and $X_6$ is W, K or A (SEQ ID NO: 13). In another embodiment, an anti-infective peptide is 16 to 26 amino acid residues in length and comprises the following amino acid sequence: $X_1X_2SWLRDX_3X_4TX_5LQSX_6L$, wherein $X_1$ is S or G; $X_2$ is S or G; $X_3$ is V, $X_4$ is W; $X_5$ is W; and $X_6$ is K or A (SEQ ID NO:14). In another embodiment, an anti-infective peptide is 16 to 26 amino acid residues in length and comprises the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W or A; and $X_6$ is W or K (SEQ ID NO:15). In another embodiment, an anti-infective peptide is 16 to 26 amino acid residues in length and comprises the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W, K or A; and $X_6$ is W, K or A (SEQ ID NO:16). In another embodiment, an anti-infective peptide is 16 to 26 amino acid residues in length and comprises the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W or A; and $X_6$ is W, K or A (SEQ ID NO:17). In another embodiment, an anti-infective peptide is 16 to 26 amino acid residues in length and comprises the following amino acid sequence: $X_1X_2SWLRDX_3X_4TX_5LQSX_6L$, wherein $X_1$ is S or G; $X_2$ is S or G; $X_3$ is V or I, $X_4$ is $X_5$ is W, K or A; and $X_6$ is W or K (SEQ ID NO:19).

In another embodiment, an anti-infective peptide consists of the following amino acid sequence: $X_1X_2SWLRDX_3X_4TX_5LQSX_6L$, wherein $X_1$ is S, G or A; $X_2$ is S or G; $X_3$ is V or I, $X_4$ is W or L; $X_5$ is W, K, A or L; and $X_6$ is W, K, L or A (SEQ ID NO:12). In another embodiment, an anti-infective peptide consists of the following amino acid sequence: $X_1X_2SWLRDX_3X_4TX_5LQSX_6L$, wherein $X_1$ is S or G; $X_2$ is S or G; $X_3$ is V; $X_4$ is W; $X_5$ is W or K; and $X_6$ is W, K or A (SEQ ID NO:13). In another embodiment, an anti-infective peptide consists of the following amino acid sequence: $X_1X_2SWLRDX_3X_4TX_5LQSX_6L$, wherein $X_1$ is S or G; $X_2$ is S or G; $X_3$ is V, $X_4$ is W; $X_5$ is W; and $X_6$ is K or A (SEQ ID NO:14). In another embodiment, an anti-infective peptide consists of the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W or A; and $X_6$ is W or K (SEQ ID NO:15). In another embodiment, an anti-infective peptide consists of the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W, K or A; and $X_6$ is W, K or A (SEQ ID NO:16). In another embodiment, an anti-infective peptide consists of the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W or A; and $X_6$ is W, K or A (SEQ ID NO:17). In another embodiment, an anti-infective peptide consists of the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W, K or A; and $X_6$ is W or K (SEQ ID NO:19).

In another embodiment, an anti-infective peptide described herein comprises, consists essentially of, or consists of a peptide set forth in Table 4. In another embodiment, an anti-infective peptide is 16 to 26 amino acid residues in length and comprises the amino acid sequence of a peptide set forth in Table 4. In another embodiment, an anti-infective peptide is 16 to 26 amino acid residues in length and comprises the following amino acid sequence: SGSWLRDVWTWLQSKL (SEQ ID NO:1). In another embodiment, an anti-infective peptide is 16 to 26 amino acid residues in length and comprises the following amino acid sequence: GSSWLRDVWTWLQSKL (SEQ ID NO:2). In another embodiment, an anti-infective peptide is 16 to 26 amino acid residues in length and comprises the following amino acid sequence: GSSWLRDVWTWLQSKL (SEQ ID NO:3). In another embodiment, an anti-infective peptide is 16 to 26 amino acid residues in length and comprises the following amino acid sequence: GSSWLRDVWTKLQSWL (SEQ ID NO:4). In another embodiment, an anti-infective peptide is 16 to 26 amino acid residues in length and comprises the following amino acid sequence: GSSWLRDIWTKLQSWL (SEQ ID NO:5). In another embodiment, an anti-infective peptide is 16 to 26 amino acid residues in length and comprises the following amino acid sequence: GSSWLRDIWTALQSWL (SEQ ID NO:6). In another embodiment, an anti-infective peptide is 16 to 26 amino acid residues in length and comprises the following amino acid sequence: GSSWLRDILTALQSLL (SEQ ID NO:7). In another embodiment, an anti-infective peptide is 16 to 26 amino acid residues in length and comprises the following amino acid sequence: AGSWLRDIWTWLQSAL (SEQ ID NO:8). In another embodiment, an anti-infective peptide is 16 to 26 amino acid residues in length and comprises the following amino acid sequence: AGSWLRDILTLLQSAL (SEQ ID NO:9).

In another embodiment, an anti-infective peptide consists of the following amino acid sequence: SGSWLRDVWTWLQSKL (SEQ ID NO:1). In another embodiment, an anti-infective peptide consists of the following amino acid sequence: GSSWLRDVWTWLQSKL (SEQ ID NO:2). In another embodiment, an anti-infective peptide consists of the following amino acid sequence: GSSWLRDVWTWLQSAL (SEQ ID NO:3). In another embodiment, an anti-infective peptide consists of the following amino acid sequence: GSSWLRDVWTKLQSWL (SEQ ID NO:4). In another embodiment, an anti-infective peptide consists of the following amino acid sequence: GSSWLRDIWTKLQSWL (SEQ ID NO:5). In another embodiment, an anti-infective peptide consists of the following amino acid sequence: GSSWLRDIWTALQSWL (SEQ ID NO:6). In another embodiment, an anti-infective peptide consists of the following amino acid sequence: GSSWLRDILTALQSLL (SEQ ID NO:7). In another embodiment, an anti-infective peptide consists of the following amino acid sequence: AGSWLRD1WTWLQSAL (SEQ ID NO:8). In another embodiment, an anti-infective peptide consists of the following amino acid sequence: AGSWLRDILTLLQSAL (SEQ ID NO:9).

In one embodiment, an anti-infective peptide described herein is a pegylated peptide and the pegylated peptide comprises, consists essentially of, or consists of a peptide set forth in Table 2A. In another embodiment, an anti-infective peptide described herein is a pegylated peptide and the pegylated peptide comprises, consists essentially of, or consists of a peptide set forth in Table 2B.

In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: $X_1X_2SWLRDX_3X_4TX_5LQSX_6L$, wherein $X_1$ is S, G or A; $X_2$ is S or G; $X_3$ is V or I, $X_4$ is W or L; $X_5$ is W, K, A or L; and $X_6$ is W, K, L or A (SEQ ID NO:12). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: $X_1X_2SWLRDX_3X_4TX_5LQSX_6L$, wherein $X_1$ is S or G; $X_2$ is S or G; $X_3$ is V: $X_4$ is W; $X_5$ is W or K; and $X_6$ is W, K or A (SEQ ID NO:13). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: $X_1X_2SWLRDX_3X_4TX_5LQSX_6L$, wherein $X_1$ is S or G; $X_2$ is S or G; $X_3$ is V, $X_4$ is W; $X_5$ is W; and $X_6$ is K or A (SEQ ID NO:14). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W or A; and $X_6$ is W or K (SEQ ID NO:15). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W, K or A; and $X_6$ is W, K or A (SEQ ID NO:16). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W or A; and $X_6$ is W, K or A (SEQ ID NO:17). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W, K or A; and $X_6$ is W or K (SEQ ID NO:19).

In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: $X_1X_2SWLRDX_3X_4TX_5LQSX_6L$, wherein $X_1$ is S, G or A; $X_2$ is S or G; $X_3$ is V or I, $X_4$ is W or L; $X_5$ is W, K, A or L; and $X_6$ is W, K, L or A (SEQ ID NO:12). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: $X_1X_2SWLRDX_3X_4TX_5LQSX_6L$, wherein $X_1$ is S or G; $X_2$ is S or G; $X_3$ is V; $X_4$ is W; $X_5$ is W or K; and $X_6$ is W, K or A (SEQ ID NO:13). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: $X_1X_2SWLRDX_3X_4TX_5LQSX_6L$, wherein $X_1$ is S or G; $X_2$ is S or G; $X_3$ is V, $X_4$ is W; $X_5$ is W; and $X_6$ is K or A (SEQ ID NO:14). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W or A; and $X_6$ is W or K (SEQ ID NO:15). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W, K or A; and $X_6$ is W, K or A (SEQ ID NO:16). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W or A; and $X_6$ is W, K or A (SEQ ID NO:17). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: $X_1X_2SWLRDX_3X_4TX_5LQSX_6L$, wherein $X_1$ is S or G; $X_2$ is S or G; $X_3$ is V or I, $X_4$ is W; $X_5$ is W, K or A; and $X_6$ is W or K (SEQ ID NO:19).

In another embodiment, an anti-infective peptide described herein is a pegylated peptide and the pegylated peptide comprises, consists essentially of, or consists of a peptide set forth in Table 4. In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: SGSWLRDVWTWLQSKL (SEQ ID NO:1). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: GSSWLRDVWTWLQSKL (SEQ ID NO:2). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: GSSWLRDVWTWLQSAL (SEQ ID NO:3). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: GSSWLRDVWTKLQSWL (SEQ ID NO:4). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: GSSWLRDIWTKLQSWL (SEQ ID NO:5). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: GSSWLRDIWTALQSWL (SEQ ID NO:6). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: GSSWLRDILTALQSLL (SEQ ID NO:7). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: AGSWLRDIWTWLQSAL (SEQ ID NO:8). In another embodiment, an anti-infective peptide described herein is a pegylated peptide and the pegylated peptide comprises a peptide of 16 to 26 amino acid residues in length linked to one, two or more polyethylene glycol (PEG) polymers, wherein the peptide comprises the following amino acid sequence: AGSWLRDILTLLQSAL (SEQ ID NO:9).

In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: SGSWLRDVWTWLQSKL (SEQ ID NO:1). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: GSSWLRDVWTWLQSKL (SEQ ID NO:2). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: GSSWLRDVWTWLQSAL (SEQ ID NO:3). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: GSSWLRDVWTKLQSWL (SEQ ID NO:4). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: GSSWLRDIWTKLQSWL (SEQ ID NO:5). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: GSSWLRDIWTALQSWL (SEQ ID NO:6). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: GSSWLRDILTALQSLL (SEQ ID NO:7). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: AGSWLRDIWTWLQSAL (SEQ ID NO:8). In another embodiment, an anti-infective peptide described herein is a pegylated peptide and the pegylated peptide comprises a peptide linked to one, two, or more polyethylene glycol (PEG) polymers, wherein the peptide consists of the following amino acid sequence: AGSWLRDILTLLQSAL (SEQ ID NO:9).

In some embodiments, a pegylated peptide described herein comprises one, two or more PEG polymers in the molecular weight range of 500 to 5000 daltons. In certain embodiments, the PEG polymers are branched. In other embodiments, the PEG polymers are non-branched.

In certain embodiments, the amino acid residues of the anti-infective peptide are L amino acids. In some embodiments, the amino acid residues of the anti-infective peptide are D amino acids. In certain embodiments, the amino acid residues of the anti-infective peptide are a mixture of D and L amino acids.

In another aspect, provided herein are compositions comprising an anti-infective peptide described herein and a carrier. In certain embodiments, the composition comprises an anti-infective peptide in an amount effective to inhibit microbial growth. In some embodiments, the composition comprises an anti-infective peptide in an amount effective to inhibit viral replication. In a specific embodiment, the carrier is an aqueous solution, such as distilled water. In certain embodiments, the compositions are pharmaceutical compositions and the carrier is a pharmaceutically acceptable carrier. The pharmaceutical composition may be formulated for any route of administration, e.g., topical, subcutaneous, intravenous, or intraperitoneal. In a specific embodiment, the pharmaceutical composition is formulated for topical administration. In another specific embodiment, the pharmaceutical composition is formulated for topical administration as a gel, wherein the effective amount of the anti-infective peptide is 0.1% to 5% in the gel formulation.

In another aspect, provided herein is a vial containing a lyophilized composition comprising 200 mg to 300 mg of an anti-infective peptide described herein. In a specific embodiment, provided herein is a vial containing a pharmaceutical composition, wherein the pharmaceutical composition comprises 200 mg to 300 mg of peptide in a 1 ml aqueous solution (e.g., sterile water).

In another aspect, provided herein is a method for inhibiting growth, replication, or infectivity of a microorganism, comprising contacting the microorganism with an effective amount of an anti-infective peptide described herein. The microorganism may be in vivo, in vitro or ex vivo. In a specific embodiment, provided herein is a method for inhibiting bacterial growth, comprising contacting the bacteria with an effective amount of an anti-infective peptide herein. The bacteria may be in viva, in vitro or ex vivo. In another specific embodiment, provided herein is a method for inhibiting viral replication in a cell, comprising contacting a cell infected with a virus with an effective amount of an anti-infective peptide described herein. The cell may be in vivo, in vitro or ex vivo.

In another aspect, provided herein are methods for treating a microorganism infection, or treating or preventing a disease associated or caused by a microorganism, in a subject, comprising administering to the subject an anti-infective peptide described herein or a pharmaceutical composition described herein. In one embodiment, provided herein is a method for treating a microorganism infection in a subject, comprising administering to the subject an anti-infective peptide described herein or a pharmaceutical composition described herein. In another embodiment, provided herein is a method for preventing a disease in a subject caused by or associated with a microorganism infection, comprising administering to the subject an anti-infective peptide described herein or a pharmaceutical composition described herein. In some embodiments, an effective amount of an anti-infective peptide that is administered to a subject in accordance with a method disclosed herein is a dose of 10 mg to 300 mg of peptide per day. In certain embodiments, an effective amount of an anti-infective peptide that is administered to a subject in accordance with a method disclosed herein is a dose of 10 mg to 300 mg of peptide twice per day. The anti-infective peptide or pharmaceutical composition may be administered to a subject via any route. In a specific embodiment, the anti-infective peptide is administered to a subject subcutaneously, topically, intravenously or intraperitoneally.

In another aspect, provided herein are methods for treating a bacterial infection, or treating or preventing a disease associated or caused by a bacteria, in a subject, comprising administering to the subject an anti-infective peptide described herein or a pharmaceutical composition described herein. In one embodiment, provided herein is a method for treating a bacterial infection in a subject, comprising administering to the subject an anti-infective peptide described herein or a pharmaceutical composition described herein. In another embodiment, provided herein is a method for preventing a disease in a subject caused by or associated with a bacterial infection, comprising administering to the subject an anti-infective peptide described herein or a pharmaceutical composition described herein. In another embodiment, provided herein is a method for inhibiting bacterial growth in a subject, comprising administering to the subject an anti-infective peptide described herein or a pharmaceutical composition described herein. In some embodiments, an effective amount of an anti-infective peptide that is administered to a subject in accordance with a method disclosed herein is a dose of 10 mg to 300 mg of peptide per day. In certain embodiments, an effective amount of an anti-infective peptide that is administered to a subject in accordance with a method disclosed herein is a dose of 10 mg to 300 mg of peptide twice per day. The anti-infective peptide or pharmaceutical composition may be administered to a subject via any route. In a specific embodiment, the anti-infective peptide is administered to a subject subcutaneously, topically, intravenously or intraperitoneally.

In another aspect, provided herein are methods for treating a viral infection, or treating or preventing a disease associated or caused by a virus, in a subject, comprising administering to the subject an anti-infective peptide described herein or a pharmaceutical composition described herein. In one embodiment, provided herein is a method for treating a viral infection in a subject, comprising administering to the subject an anti-infective peptide described herein or a pharmaceutical composition described herein. In another embodiment, provided herein is a method for preventing a disease in a subject caused by or associated with a viral infection, comprising administering to the subject an anti-infective peptide described herein or a pharmaceutical composition described herein. In some embodiments, an effective amount of an anti-infective peptide that is administered to a subject in accordance with a method disclosed herein is a dose of 10 mg to 300 mg of peptide per day. In certain embodiments, an effective amount of an anti-infective peptide that is administered to a subject in accordance with a method disclosed herein is a dose of 10 mg to 300 mg of peptide twice per day. The anti-infective peptide or pharmaceutical composition may be administered to a subject via any route. In a specific embodiment, the anti-infective peptide is administered to a subject subcutaneously, topically, intravenously or intraperitoneally.

In certain embodiments, a microorganism is bacteria. In some embodiments, the bacteria is Gram-positive. The Gram-positive bacteria may be *Staphylococcus aureus*, enterococci (e.g., *Enterococcus faecalis*), streptococci (e.g., *Streptococcus pneumonia*), *Clostridium difficile*, *Propionibacterium acnes*, or *Bacillus anthracis*. In other embodiments, the bacteria is Gram-negative. The Gram-negative bacteria may be *Pseudomonas aeruginosa*, *Moraxella catarrhalis*, or *Haemophilus influenzae*. In specific embodiments, the bacteria is Methicillin-sensitive *Staphylococcus aureus*, Methicillin-resistant *Staphylococcus aureus*, Vancomycin-sensitive enterococci, Vancomycin-resistant enterococci, penicillin-sensitive *Streptococcus pneumoniae*, penicillin-resistant *Streptococcus pneumoniae*, ciprofloxacin-resistant or clindamycin-resistant.

In certain embodiments, a virus is a virus belonging to the Flaviviridae, Togaviridae, Filoviridae, Retroviridae, Arenaviridae, Bunyaviridae, or Poxviridae family. In specific embodiments, a virus is a dengue virus, Chikungunya virus, Ebola virus, HIV, or influenza virus.

In another aspect, provided herein is a disinfecting solution or composition comprising anti-infective peptide described herein. In another aspect, provided herein is a method for disinfecting an inanimate object or biological material, comprising contacting the object with a disinfecting solution or composition. In a specific embodiment, provided herein is a method for disinfecting an inanimate object or biological material, comprising contacting the object with a wipe containing an anti-infective peptide described herein.

In another aspect, provided herein is an inanimate surface or biological surface, which comprises a linkage to or a coating with an anti-infective peptide.

3.1 Terminology

4. BRIEF DESCRIPTION OF THE DRAWINGS

Figure 1B:
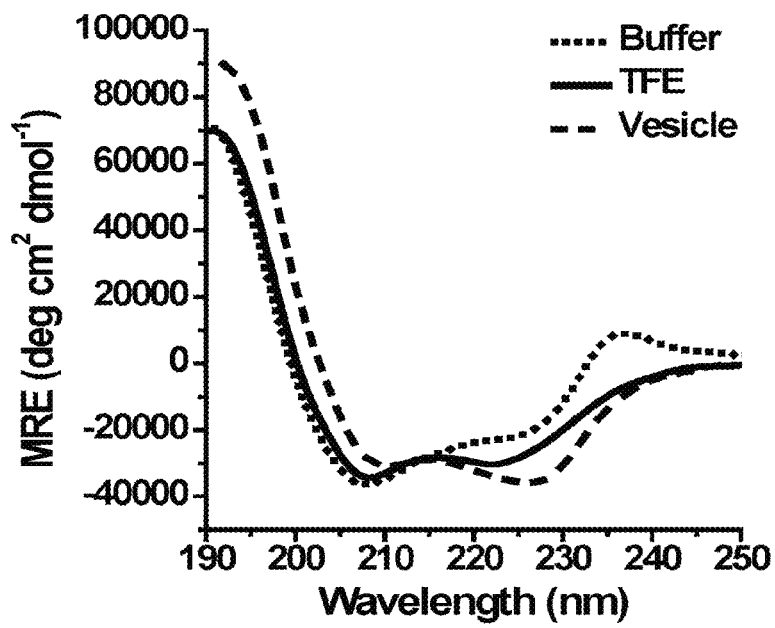
Figure 1C:
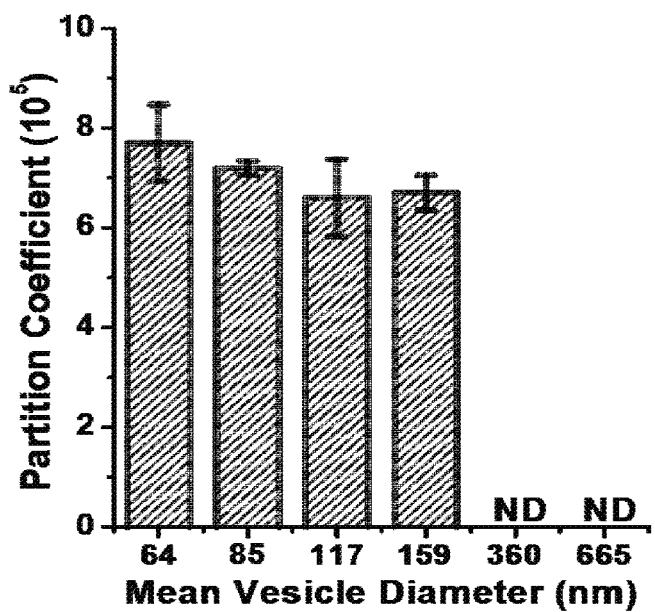

FIG. 1A, FIG. 1B and FIG. 1C. FIG. 1A: Virus neutralization occurs by directly lysing virus particles, thereby preventing viral infection ("viral entry inhibition"). FIG. 1B: Circular dichroism spectra were recorded for anti-infective peptide TSG001 (SEQ ID NO:1) in buffer (dotted line), 50 v/v % 2,2,2-trifluoroethanol (TFE) (solid line), and POPC lipid vesicles (dashed line) at 25° C. FIG. 1C: Mole fraction partition coefficients, $K_x$, are presented as a function of mean vesicle diameter for the anti-infective peptide TSG001 (SEQ ID NO:1) (mean±standard deviation for n=3 independent experiments). ND means not determined in cases where the partition coefficient could not be determined due to minimal partitioning.

Figure 2A:
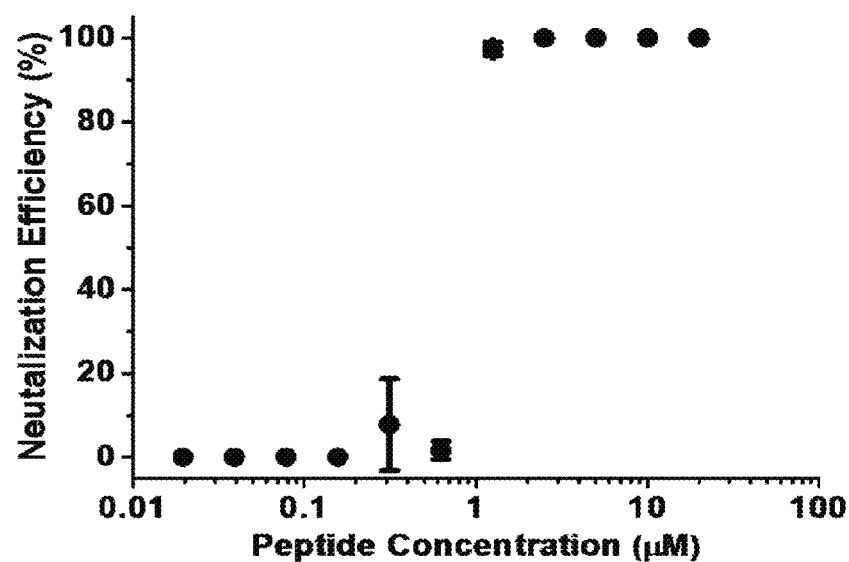
Figure 2B:
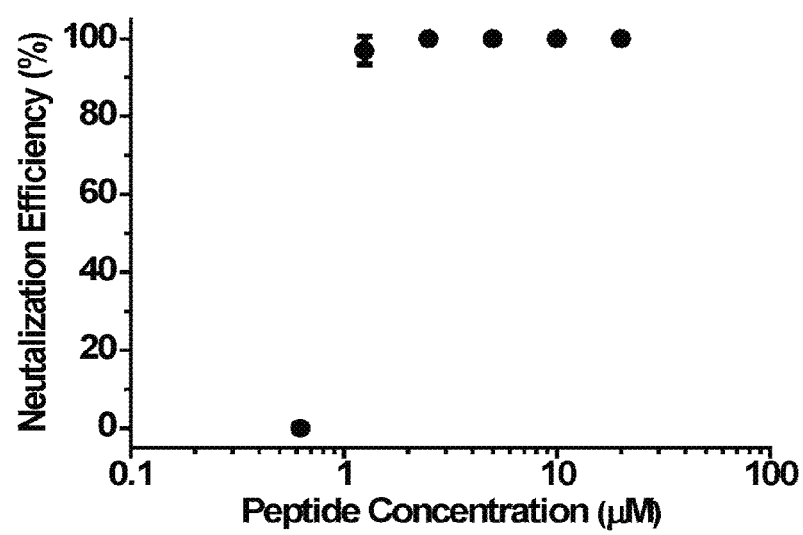
Figure 2C:
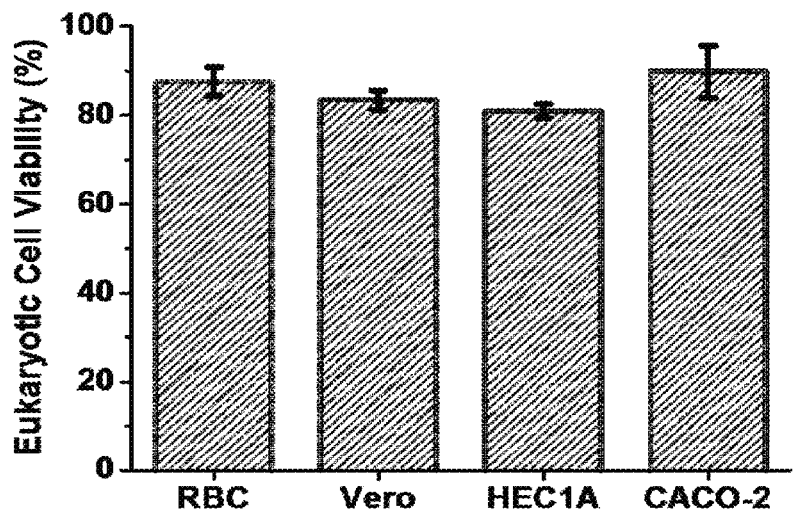
Figure 2D:
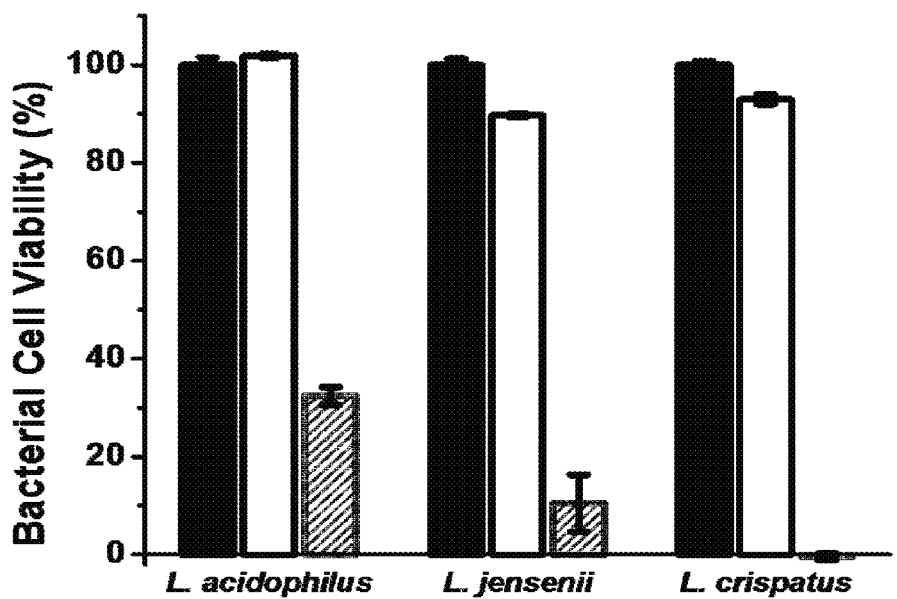

FIG. 2A, FIG. 2B, FIG. 2C and FIG. 2D. FIG. 2A: Neutralization efficiency of anti-infective peptide TSG001 (SEQ ID NO:1) against ZIKV strain FSS13025 as a function of peptide concentration in a plaque reduction assay. FIG. 2B: Neutralization efficiency of anti-infective peptide TSG001 (SEQ ID NO:1) against ZIKV strain FSS13025 as a function of peptide concentration in a virus yield reduction assay. FIG. 2C: Cell viability of various cell lines, expressed as % live cells, after treatment with 50 μM anti-infective peptide TSG001 (SEQ ID NO:1). FIG. 2D: Evaluation of vaginal microflora bacterial growth inhibition after treatment with 50 μM anti-infective peptide TSG001 (SEQ ID NO:1). Black columns (negative control; no peptide), white columns (treatment with 50 μM TSG001), dashed columns (positive control; antibiotic treatment).

Figures 3A, 3B:
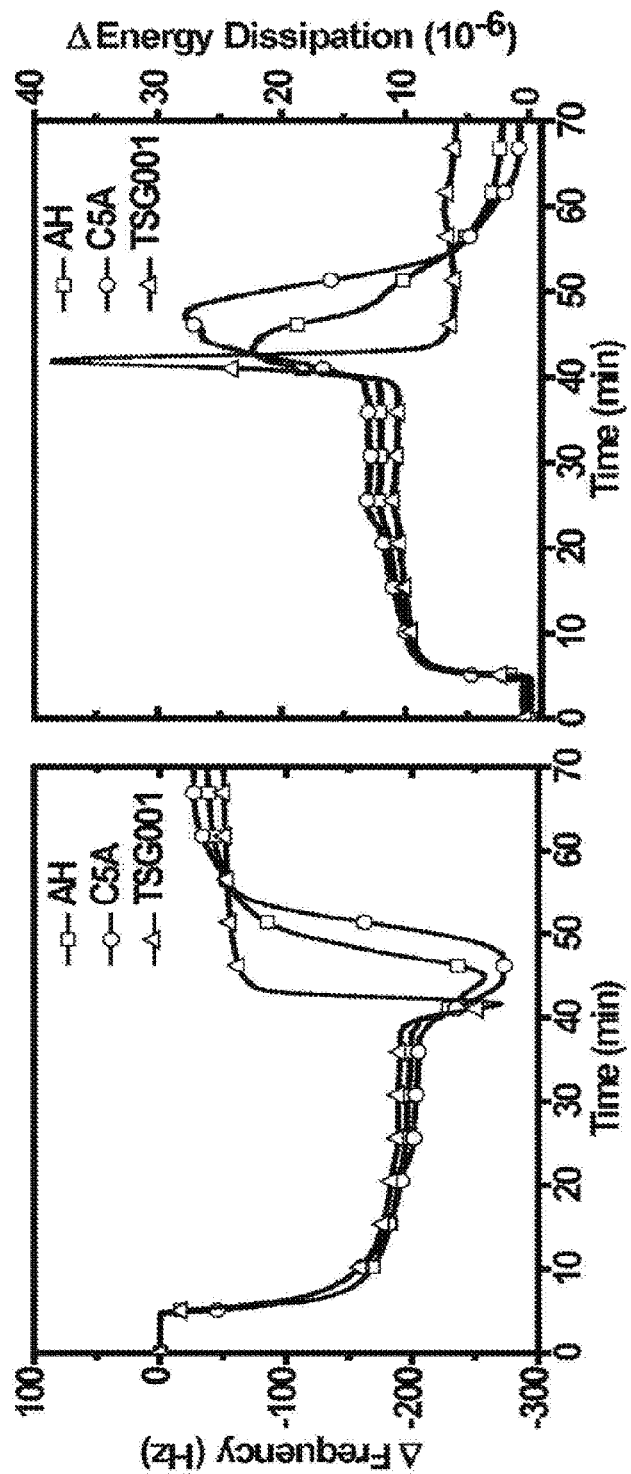

FIG. 3A and FIG. 3B: QCM-D (FIG. 3A) frequency and (FIG. 3B) energy dissipation kinetic curves capture the interaction between TSG001 (SEQ ID NO:1), AH (SEQ ID NO:10) or C5A (SEQ ID NO:11) peptides and surface-adsorbed vesicles (50 mol % DOPC and 50 mol % Cholesterol). The arrow indicates the time point when peptides were added to the adsorbed vesicle layers.

5. DETAILED DESCRIPTION

Short, amphipathic peptides have been developed that have potent, broad-spectrum anti-infective activity against many clinically-important viruses (e.g., Zika virus), including dengue virus (DENY), Chikungunya virus, Yellow Fever virus, Rift Valley fever virus, and Japanese encephalitis virus, with EC50 values in the range of 0.5-3 μM or 1-3 μM. Strikingly, the peptides also demonstrate strong antibacterial activity against *S. aureus* skin bacteria (MIC value of, e.g., 6 μM or 1.5 μM), with comparable antibacterial activities to melittin and a much more attractive therapeutic profile (low cytoxicity; >50 μM). It also works against many other medically important bacteria. As a drug candidate, this peptide is particularly attractive because its acts via a membrane-disrupting mechanism with a high harrier to the evolution of drug-resistant bacterial and viral strains. It is the first known peptide with potent broad-spectrum antiviral and antibacterial activity.

Peptides described herein are the only peptides known with potent antiviral and antibacterial activity. Competitors' antiviral peptides have almost zero antibacterial activity. The peptides target many viruses of medical and biodefense importance including but not limited to members of the Flaviviridae, Togaviridae, Filoviridae, Retroviridae, and Orthomyxoviridae families. Exemplary viruses include Dengue, Chikungunya, Ebola, HIV, Zika virus and Influenza. The mechanism of action allows the peptide to target standard and antibiotic-resistant bacterial strains. The peptide has an excellent therapeutic index (typically more than 10 depending on pathogen) compared to classical antimicrobial peptides (in many cases, less than 1). The peptide has a short amino acid sequence compared to most therapeutic peptides in clinics (e.g., 16 amino acids vs. 36 amino acids for anti-HIV drug Enfuvirtide marketed by Roche). The peptide is highly soluble in water for easy formulation. Competitors' antiviral peptides are poorly soluble and require organic solvent in formulation. Bacteria and viruses have a very high barrier (effectively zero) to become resistant to product (the anti-infective peptide described herein).

5.1 Anti-Infective Peptides

Provided herein are anti-infective peptides (e.g., synthetic peptides). In a specific embodiment, an anti-infective peptide provided herein comprises or consists of an amino acid sequence listed in Table 2A or Table 2B. In a specific embodiment, an anti-infective peptide provided herein consists essentially of an amino acid sequence listed in Table 2A or Table 2B.

TABLE 2A

Anti-infective peptides
Amino Acid Sequence of Anti-infective
Peptide Consensus Sequences (SEQ ID NO)

$X_1X_2SWLRDX_3X_4TX_5LQSX_6L$,
wherein:
$X_1$: small amino acid;
$X_2$: small amino acid;
$X_3$: hydrophobic amino acid
with an aliphatic side chain;
$X_4$: hydrophobic amino acid;
$X_5$: hydrophilic amino acid or
polar amino acid;
$X_6$: hydrophilic amino acid or
polar amino acid
(SEQ ID NO: 21).

$X_1X_2SWLRDX_3X_4TX_5LQSX_6L$,
wherein:
$X_1$: small amino acid;
$X_2$: small amino acid;
$X_3$: hydrophobic amino acid
with an aliphatic side chain;
$X_4$: hydrophobic amino acid;
$X_5$: hydrophilic amino acid;
$X_6$: hydrophilic amino acid
(SEQ ID NO: 22).

$X_1X_2SWLRDX_3X_4TX_5LQSX_6L$,
wherein:
$X_1$: small amino acid;
$X_2$: small amino acid;
$X_3$: hydrophobic amino acid with
an aliphatic side chain;
$X_4$: hydrophobic amino acid;
$X_5$: polar amino acid;
$X_6$: polar amino acid
(SEQ ID NO: 23).

$X_1X_2SWLRDX_3X_4TX_5LQSX_6L$,
wherein:
$X_1$: small amino acid;
$X_2$: small amino acid;
$X_3$: hydrophobic amino acid
with an aliphatic side chain;
$X_4$: hydrophobic amino acid;
$X_5$: hydrophilic amino acid;
$X_6$: polar amino acid
(SEQ ID NO: 24).

$X_1X_2SWLRDX_3X_4TX_5LQSX_6L$,
wherein:
$X_1$: small amino acid;
$X_2$: small amino acid;
$X_3$: hydrophobic amino acid
with an aliphatic side chain;
$X_4$: hydrophobic amino acid;

TABLE 2A-continued

Anti-infective peptides
Amino Acid Sequence of Anti-infective
Peptide Consensus Sequences (SEQ ID NO)

$X_5$: polar amino acid;
$X_6$: hydrophilic amino acid
(SEQ ID NO: 25).

$X_1X_2SWLRDX_3X_4TX_5LQSX_6L$,
wherein:
$X_1$: conservative amino acid substitution
for serine, glycine or alanine;
$X_2$: conservative amino acid substitution
for serine, glycine or alanine;
$X_3$: conservative amino acid substitution
for valine or isoleucine;
$X_4$: conservative amino acid substitution
for tryptophan or leucine;
$X_5$: conservative amino acid substitution
for tryptophan, lysine, alanine or leucine;
$X_6$: conservative amino acid substitution
for tryptophan, lysine, alanine or leucine
(SEQ ID NO: 26).

$X_1X_2SWLRDX_3X_4TX_5LQSX_6L$,
wherein:
$X_1$: A, C, G, P, S, T;
$X_2$: A, C, G, P, S, T;
$X_3$: A, I, L, P or V;
$X_4$: W, F, Y, H, A, I, L, P or V;
$X_5$: W, F, Y or H;
$X_6$: W, F, Y or H
(SEQ ID NO: 27).

$X_1X_2SWLRDX_3X_4TX_5LQSX_6L$,
wherein:
$X_1$: A, C, G, P, S, T:
$X_2$: A, C, G, P, S, T;
$X_3$: A, I, L, P or V;
$X_4$: W, F, Y, H, A, I, L, P or V;
$X_5$: W, F, Y or H;
$X_6$: K, Y, R, H, N, Q, S, or T
(SEQ ID NO: 28).

$X_1X_2SWLRDX_3X_4TX_5LQSX_6L$,
wherein:
$X_1$: A, C, G, P, S, T;
$X_2$: A, C, G, P, S, T;
$X_3$: A, I, L, P or V;
$X_4$: W, F, Y, H, A, I, L, P or V;
$X_5$: W, F, Y or H:
$X_6$: A, C, G, P, S, I, L, V or T
(SEQ ID NO: 29).

$X_1X_2SWLRDX_3X_4TX_5LQSX_6L$,
wherein:
$X_1$: A, C, G, P, 5, T;
$X_2$: A, C, G, P, S, T;
$X_3$: A, I, L, P or V;
$X_4$: W, F, Y, H, A, I, L, P or V;
$X_5$: K, Y, R, H, N, Q, S, or T;
$X_6$: W, F, Y or H
(SEQ ID NO: 30).

$X_1X_2SWLRDX_3X_4TX_5LQSX_6L$.
wherein:
$X_1$: A, C, G, P, S, T:
$X_2$: A, C, G, P, S, T;
$X_3$: A, I, L, P or V;
$X_4$: W, F, Y, H, A, I, L, P or V;
$X_5$: K, Y, R, H, N, Q, S, or T;
$X_6$: K, Y, R, H, N, Q, S, or T
(SEQ ID NO: 31).

$X_1X_2SWLRDX_3X_4TX_5LQSX_6L$,
wherein:
$X_1$: A, C, G, P, S, T:
$X_2$: A, C, G, P, S, T:
$X_3$: A, I, L, P or V;
$X_4$: W, F, Y, H, A, I, L, P or V;

TABLE 2A-continued

Anti-infective peptides
Amino Acid Sequence of Anti-infective
Peptide Consensus Sequences (SEQ ID NO)

$X_5$: K, Y, R, H, N, Q, S, or T;
$X_6$: A, C, G, P, S, I, L, V or T
(SEQ ID NO: 32).

$X_1X_2SWLRDX_3X_4TX_5LQSX_6L$,
wherein:
$X_1$: A, C, G, P, S, T;
$X_2$: A, C, G, P, S, T:
$X_3$: A, I, L, P or V;
$X_4$: W, F, Y, H, A, I, L, P or V;
$X_5$: A, C, G, P, S, I, L, V or T;
$X_6$: W, F, Y or H
(SEQ ID NO: 33).

$X_1X_2SWLRDX_3X_4TX_5LQSX_6L$;
wherein:
$X_1$: A, C, G, P, S, T;
$X_2$: A, C, G, P, S, T:
$X_3$: A, I, L, P or V;
$X_4$: W, F, Y, H, AA, L, P or V;
$X_5$: A, C, G, P, S, I, L, V or T;
$X_6$: K, Y, R, H, N, Q, S, or T
(SEQ ID NO: 34).

$X_1X_2SWLRDX_3X_4TX_5LQSX_6L$,
wherein:
$X_1$: A, C, G, P, S, T;
$X_2$: A, C, G, P, S, T:
$X_3$: A, I, L, P or V;
$X_4$: W, F, Y, H, A, I, L, P or V;
$X_5$: A, C, G, P, 5, I, L, V or T;
$X_6$: A, C, G, P, S, I, L, V or T
(SEQ ID NO: 35).

$X_1X_2SWLRDX_3X_4TX_5LQSX_6L$,
wherein:
$X_1$: G, P, or A;
$X_2$: G, P, or A;
$X_3$: V, I, L or M;
$X_4$: W, F, Y or H;
$X_5$: W, Y, or F;
$X_6$: K, R, Q, E or N
(SEQ ID NO: 36).

$X_1X_2SWLRDX_3X_4TX_5LQSX_6L$,
wherein:
$X_1$: S, T, A or Q;
$X_2$: G, P, or A;
$X_3$: V, I, L or M;
$X_4$: W, F, Y or H;
$X_5$: W, Y, or F;
$X_6$: K, R, Q, E or N
(SEQ ID NO: 37).

$X_1X_2SWLRDX_3X_4TX_5LQSX_6L$,
wherein:
$X_1$: G, P, or A;
$X_2$: G, P, or A;
$X_3$: V, I, L or M;
$X_4$: W, F, Y or H;
$X_5$: K, R, Q, E or N;
$X_6$: W, Y, or F
(SEQ ID NO: 38).

$X_1X_2SWLRDX_3X_4TX_5LQSX_6L$,
wherein:
$X_1$: S, T, A or Q;
$X_2$: G, P, or A;
$X_3$: V, I, L or M;
$X_4$: W, F, Y or H;
$X_5$: K, R, Q, E or N;
$X_6$: W, Y, or F
(SEQ ID NO: 39).

TABLE 2A-continued

Anti-infective peptides
Amino Acid Sequence of Anti-infective
Peptide Consensus Sequences (SEQ ID NO)

$X_1X_2SWLRDX_3X_4TX_5LQSX_6L$,
wherein:
$X_1$: S, T, A or Q;
$X_2$: G, P, or A;
$X_3$: V, I, L or M;
$X_4$: W, F, Y or H;
$X_5$: A, S, G or T;
$X_6$: W, Y, or F
(SEQ ID NO: 40).

$X_1X_2SWLRDX_3X_4TX_5LQSX_6L$,
wherein:
$X_1$: G, P, or A;
$X_2$: G, P, or A;
$X_3$: V, I, L or M;
$X_4$: W, F, Y or H;
$X_5$: A, S, G or T;
$X_6$: W, Y, or F
(SEQ ID NO: 18).

TABLE 2B

Anti-infective peptides
Amino Acid Sequence of Anti-infective
Peptide Consensus Sequences (SEQ ID NO)

$X_1X_2SWLRDX_3X_4TX_5LQSX_6L$,
wherein $X_1$ is S, G or A;
$X_2$ is S or G;
$X_3$ is V or I;
$X_4$ is W or L;
$X_5$ is W, K, A or L;
and $X_6$ is W, K, L or A
(SEQ ID NO: 12)

$X_1X_2SWLRDX_3X_4TX_5LQSX_6L$,
wherein $X_1$ is S or G;
$X_2$ is S or G;
$X_3$ is V;
$X_4$ is W;
$X_5$ is W or K;
and $X_6$ is W, K or A
(SEQ ID NO: 13)

$X_1X_2SWLRDX_3X_4TX_5LQSX_6L$,
wherein $X_1$ is S or G;
$X_2$ is S or G;
$X_3$ is V;
$X_4$ is W;
$X_5$ is W;
and $X_6$ is K or A
(SEQ ID NO: 14)

$X_1X_2SWLRDX_3X_4TX_5LQSX_6L$,
wherein $X_1$ is S or G;
$X_2$ is S or G;
$X_3$ is V or I;
$X_4$ is W;
$X_5$ is W or A;
and $X_6$ IS W or K
(SEQ ID NO: 15)

$X_1X_2SWLRDX_3X_4TX_5LQSX_6L$,
wherein $X_1$ is S or G;
$X_2$ is S or G;
$X_3$ is V or I;
$X_4$ is W;
$X_5$ is W, K or A;
and $X_6$ is W, K or A
(SEQ ID NO: 16)

TABLE 2B-continued

Anti-infective peptides
Amino Acid Sequence of Anti-infective
Peptide Consensus Sequences (SEQ ID NO)

X₁X₂SWLRDX₃X₄TX₅LQSX₆L,
wherein X₁ is S or G;
X₂ is S or G;
X₃ is V or I;
X₄ is W; X₅ is W or A;
and X₆ is W, K or A
(SEQ ID NO: 17)

X₁X₂SWLRDX₃X₄TX₅LQSX₆L,
wherein X₁ is S or G;
X₂ is S or G;
X₃ is V or I;
X₄ is W;
X₅ is W, K or A;
and X₆ iS W or K
(SEQ ID NO: 19)

As one of skill in the art would appreciate, amino acids can be categorized in different classes depending upon the chemical and physical properties of the amino acid residue. For example, some amino acid residues are classified based upon their side chains as hydrophilic or polar amino acids, while other amino acids are classified as hydrophobic or nonpolar amino acids. The term "polar amino acid" is a term known to one of skill in the art. Typically a "polar amino acid" refers to a hydrophilic amino acid having a side chain that is charged or uncharged at physiological pH and are generally hydrophilic, meaning that they have an amino acid side chain that is attracted by aqueous solution. Examples of polar amino acids include aspartate, glutamate, glutamine, lysine, arginine, histidine, asparagine, serine, threonine and tyrosine. Hydrophobic amino acids are known to one of skill in the art. Typically, hydrophobic amino acids can be further classified as having an aliphatic side chain or an aromatic side chain. Aliphatic amino acids and aromatic amino acids are known one of skill in the art. Typically, aliphatic amino acids have a side chain containing hydrogen and carbon atoms. Examples of aliphatic amino acids include alanine, isoleucine, proline, and valine. Typically, aromatic amino acids contain a side chain containing an aromatic ring. Examples of aromatic amino acids include phenylalanine, tyrosine, histidine and tryptophan. In some instances, amino acids are classified as small amino acids because they are small in size. Examples of small amino acids include alanine, cysteine, glycine, proline, serine and threonine.

One skilled in the art would appreciate that an amino acid may be substituted with an amino acid with similar chemical and physical properties. These substitutions are typically referred to as conservative substitutions. In particular embodiments, a conservative substitution does not alter the structure or function, or both, of a peptide. For example, a hydrophobic amino acid may be substituted for another hydrophobic amino acid, a neutral hydrophilic amino acid may be substituted for another neutral hydrophilic amino acid, an acidic amino acid may be substituted for another acidic amino acid, a basic amino acid may be substituted for another basic amino acid, an aromatic amino acid may be substituted for another aromatic amino acid, etc. Examples of conservative amino acid substitutions are as follows in Table 3.

TABLE 3

| Original Residue | Conservative substitution |
|---|---|
| Ala | Ser, Gly, Thr |
| Arg | Lys, Gln, His, Lys |
| Asn | Asp, Gln, His, Lys, Ser, Thr |
| Asp | Asn, Glu |
| Cys | Ser |
| Gln | Arg, ASn, Glu, His, Lys, Met |
| Gly | Ala, Pro |
| His | Asn, Arg, Gln, Tyr |
| Ile | Leu, Val, Met |
| Leu | Ile, Met, Phe, Val |
| Lys | Arg, Asn, Gln, Glu |
| Met | Gln, Ile, Leu, Val |
| Phe | Leu, Trp, Tyr, Met |
| Ser | Ala, Asn, Thr |
| Thr | Ser, Ala, Asn |
| Trp | Phe, Tyr |
| Tyr | His, Phe, Trp |
| Val | Ile, Leu, Met |

In a specific embodiment, an anti-infective peptide provided herein comprises or consists of an amino acid sequence listed in Table 4.

TABLE 4

Amino acid sequences of anti-infective peptides TSG001-TSG009.

| Name of Anti-Infective Peptide | Amino Acid Sequence (SEQ ID NO) |
|---|---|
| TSG001 | SGSWLRDVWTWLQSKL (SEQ ID NO: 1) |
| TSG002 | GSSWLRDVWTWLQSKL (SEQ ID NO: 2) |
| TSG003 | GSSWLRDVWTWLQSAL (SEQ ID NO: 3) |
| TSG004 | GSSWLRDVWTKLQSWL (SEQ ID NO: 4) |
| TSG005 | GSSWLRDIWTKLQSWL (SEQ ID NO: 5) |
| TSG006 | GSSWLRDIWTALQSWL (SEQ ID NO: 6) |
| TSG007 | GSSWLRDILTALQSLL (SEQ ID NO: 7) |
| TSG008 | AGSWLRDIWTWLQSAL (SEQ ID NO: 8) |
| TSG009 | AGSWLRDILTLLQSAL (SEQ ID NO: 9) |

In a specific embodiment, the anti-infective peptide comprises or consists of the amino acid sequence SGSWLRDVWTWLQSKL (SEQ ID NO: 1). In a specific embodiment, the anti-infective peptide comprises or consists of the amino acid sequence GSSWLRDVWTWLQSKL (SEQ ID NO:2). In a specific embodiment, the anti-infective peptide comprises or consists of the amino acid sequence GSSWLRDVWTWLQSAL (SEQ ID NO:3). In a specific embodiment, the anti-infective peptide comprises or consists of the amino acid sequence GSSWLRDVWTKLQSWL (SEQ ID NO:4). In a specific embodiment, the anti-infective peptide comprises or consists of the amino acid sequence GSSWLRDIWTKLQSWL (SEQ ID NO:5). In a specific embodiment, the anti-infective peptide comprises or consists of the amino acid sequence GSSWLRDIWTALQSWL (SEQ ID NO:6). In a specific embodiment, the anti-infective peptide comprises or consists of the amino acid sequence GSSWLRDILTALQSLL (SEQ ID NO:7). In a specific embodiment, the anti-infective peptide comprises or consists of the amino acid sequence AGSWLRDIWTWLQSAL (SEQ ID NO:8). In a specific embodiment, the anti-infective peptide comprises or consists of the amino acid sequence AGSWLRDILTLLQSAL (SEQ ID NO:9).

In a specific embodiment, an anti-infective peptide provided herein consists essentially of an amino acid sequence listed in Table 4. In another specific embodiment, the anti-infective peptide consists essentially of the amino acid sequence SGSWLRDVWTWLQSKL (SEQ ID NO: 1). In another specific embodiment, the anti-infective peptide consists essentially of the amino acid sequence GSSWLRDVWTWLQSKL (SEQ ID NO:2). In a specific embodiment, the anti-infective peptide consists essentially of the amino acid sequence GSSWLRDVWTWLQSAL (SEQ ID NO:3). In another specific embodiment, the anti-infective peptide consists essentially of the amino acid sequence GSSWLRDVWTKLQSWL (SEQ ID NO:4). In another specific embodiment, the anti-infective peptide consists essentially of the amino acid sequence GSSWLRDIWTKLQSWL (SEQ ID NO:5). In another specific embodiment, the anti-infective peptide consists essentially of the amino acid sequence GSSWLRDIWTALQSWL (SEQ ID NO:6). In another specific embodiment, the anti-infective peptide consists essentially of the amino acid sequence GSSWLRDILTALQSLL (SEQ ID NO:7). In another specific embodiment, the anti-infective peptide consists essentially of the amino acid sequence AGSWLRDIWTWLQSAL (SEQ ID NO:8). In a specific embodiment, the anti-infective peptide consists essentially of the amino acid sequence AGSWLRDILTLLQSAL (SEQ ID NO:9).

In a specific embodiment, an anti-infective peptide provided herein comprises a peptide sequence disclosed herein and additional amino acid residues (e.g., 1, 2, 3, 4, 5, 6, 7, 8, 9, or 10 amino acid residues) that do not impart a significant effect on the basic structural and functional characteristics of a peptide described in Section 6. For example, the additional amino acid residues do not have a significant effect on the EC50 and CC50 of the peptide and the structure of the peptide described in Section 6 is maintained, as assessed by a technique known to one skilled in the art, such as described in Section 5.8 and/or Section 6. In a particular embodiment, the additional amino acid residues do not increase the EC50 by more than 5 fold and do not decrease the CC50 by more than 5 fold.

In a specific embodiment, an anti-infective peptide provided herein comprises a peptide described herein and is between 16 and 26 amino acid residues in length. In a specific embodiment, an anti-infective peptide provided herein comprises a peptide described herein and is 16 amino acid residues in length. In a specific embodiment, an anti-infective peptide provided herein comprises a peptide described herein and is 17 amino acid residues in length. In a specific embodiment, an anti-infective peptide provided herein comprises a peptide described herein and is 18 amino acid residues in length. In a specific embodiment, an anti-infective peptide provided herein comprises a peptide described herein and is 19 amino acid residues in length. In a specific embodiment, an anti-infective peptide provided herein comprises a peptide described herein and is 20 amino acid residues in length. In a specific embodiment, an anti-infective peptide provided herein comprises a peptide described herein and is 21 amino acid residues in length. In a specific embodiment, an anti-infective peptide provided herein comprises a peptide described herein and is 22 amino acid residues in length. In a specific embodiment, an anti-infective peptide provided herein comprises a peptide described herein and is 23 amino acid residues. In a specific embodiment, an anti-infective peptide provided herein comprises a peptide described herein and is 24 amino acid residues in length. In a specific embodiment, an anti-infective peptide provided herein comprises a peptide described herein and is 25 amino acid residues in length. In a specific embodiment, an anti-infective peptide provided herein comprises a peptide described herein and is 26 amino acid residues in length.

In certain embodiments, an anti-infective peptide comprises an amino acid sequence in Table 2A, Table 2B, or Table 4 but with 1, 2, 3, 4, or 5 consecutive amino acids deleted from the N-terminus or C-terminus. In some embodiments, the anti-infective peptide comprises an amino acid sequence in Table 2A, Table 2B, or Table 4 but with 1, 2, 3, 4, or 5 consecutive amino acids deleted from the N-terminus and 1, 2, 3, 4, or 5 consecutive amino acids deleted from C-terminus.

In certain embodiments, an anti-infective peptide described herein is linked (directly or indirectly) to a peptide tag (e.g., a HIS-tag or FLAG-tag). In some embodiments, a linker sequence (e.g., a 1-5, 1-10 or 5-10 amino acid linker, such as a glycine linker) is used to link a peptide tag to an anti-infective peptide described herein. In other embodiments, a peptide tag is linked directly to an anti-infective peptide. The linkage between the peptide tag and anti-infective peptide may be covalent or non-covalent.

In a specific embodiment, the amino acid residues of an anti-infective peptide described herein are L amino acids. In a specific embodiment, the amino acid residues of an anti-infective peptide described herein are D amino acids. In a specific embodiment, the amino acid residues of an anti-infective peptide described herein are a mixture of D and L amino acids. In a specific embodiment, the amino acid sequence of an anti-infective peptide described herein contains L amino acids. In a specific embodiment, the amino acid sequence of an anti-infective peptide described herein contains D amino acids. In a specific embodiment, the amino acid sequence of an anti-infective peptide described herein contains a mixture of D and L amino acids.

In a specific embodiment, an anti-infective peptide described herein (see Section 5.1, Section 5.2, and Section 6) comprises one, two, or more amino acid derivatives. For example, in a specific embodiment, an anti-infective peptide described herein comprises one, two, or more non-naturally occurring or non-genetically encoded amino acids. Non-limiting examples of non-genetically encoded amino acids include α-amino hexanoic acid, α-amino valeric acid, 1,2,3,4-tetrahydro-isoquinoline-3-carboxylic acid, 2,3,-diaminobutyric acid 2,3-diaminopropionic acid, 2,4-diamino butyric acid, 2-fluorophenylalanine, 3-bezothienyl alanine, 3-fluorophenylalanine, 4-chlorophenylalanine, 4-fluorophenylalanine, A-2-thienylalanine, A-alanine, A-aminoisobutyric acid, citrulline, cyclohexylalanine, henylglycine, homoarginine, homocysteine, homoserine, methionine sulfoxide, N-acetyl lysine, N-aminophenylalanine, N-methylglycine, N-methylisoleucine, N-methylvaline, naphthylalanine, norleucine, ornithine, penicillamine, pyridylalanine, t-butylalanine, and t-butylglycine.

In a specific embodiment, an anti-infective peptide described herein comprises one, two, or more modified peptide linkages. Non-limiting examples of modified peptide linkages include —CH$_2$NH—, —CH$_2$S—, —CH=CH— (cis and trans), —COCH$_2$—, —CH(OH) CH$_2$—, and —CH$_2$SO—.

Side chain crosslinking is one of the numerous strategies that aim to stabilize and/or mimic peptide helices. In certain embodiments, an anti-infective peptide described herein is a stapled peptide. In a specific embodiment, an anti-infective peptide described herein comprises one, two, three or more staples. See, e.g., U.S. Patent Application Publication No. 2010/0093086A1 and Bird et al., "Hydrocarbon double-stapling remedies the proteolytic instability of a lengthy peptide therapeutic," PNAS 107 (32): 14093-14098 (2010), each of which is incorporated herein by reference, for a description of stapled peptides and methods for producing stapled peptides.

In some embodiments, an anti-infective peptide described herein is lipidated. In a specific embodiment, one, two or more lipids or fatty acids is added to the peptide. See, e.g., Zhang and Bulaj, "Converting peptides into drug leads by lipidation," Curr. Med. Chem. 19(11): 1602-1618 (2012) and Ward et al., "Peptide lipidation stabilizes structure to enhance biological function," Mol. Metabol. 2(4): 468-479 (2013), each of which is incorporated herein by reference for a description of peptide lipidation and methods for lipidating peptides.

In a specific embodiment, an anti-infective peptide described herein is pegylated. See Sections 5.2 and 6 for a description of the pegylation of a peptide described herein. In another specific embodiment, an anti-infective peptide described herein is linked (directly or indirectly) to a hydrophilic polymer. See Section 5.2 for a description of hydrophilic polymers.

In a specific embodiment, an anti-infective peptide described herein is effective against one, two, or more of microorganisms described in Section 5.7. For example, an anti-infective peptide described herein or a composition comprising such an anti-infective peptide (see Section 5.4) is effective at achieving one, two, or more of the following results: (i) inhibition of the growth of one, two, or more of microorganisms described in Section 5.7; (ii) inhibition of the replication of one, two, or more of microorganisms described in Section 5.7; (iii) killing of one, two, or more of microorganisms described in Section 5.7; (iv) treating an infection with by one, two, or more of microorganisms described in Section 5.7; (v) preventing an infection with one, two, or more of microorganisms described in Section 5.7; (vi) treating a disease caused by or associated with one, two, or more of microorganisms described in Section 5.7; (vii) preventing a disease caused by or associated with one, two, or more of microorganisms described in Section 5.7; (viii) disinfecting an inanimate surface or a biological surface; and/or (viii) disinfecting an inanimate or biological material. In a specific embodiment, an anti-infective peptide described herein is effective against one, two, or more of the virus families described in Section 5.7. In another specific embodiment, an anti-infective peptide described herein is effective against one, two, or more of the viruses described in Section 5.7. In a specific embodiment, an anti-infective peptide described herein is effective against one, two, or more of the bacterial families described in Section 5.7. In another specific embodiment, an anti-infective peptide described herein is effective against one, two, or more of the bacteria described in Section 5.7. In another specific embodiment, an anti-infective peptide described herein is effective against one, two, or more of the virus families described in Section 5.7 and one, two, or more of the bacterial families described in Section 5.7. In another specific embodiment, an anti-infective peptide described herein is effective against one, two, or more of the virus families described in Section 5.7 and one, two, or more of the bacteria described in Section 5.7. In another specific embodiment, an anti-infective peptide described herein is effective against one, two, or more of the viruses described in Section 5.7 and one, two, or more of the bacterial families described in Section 5.7. In another specific embodiment, an anti-infective peptide described herein is effective against one, two, or more of the viruses described in Section 5.7 and one, two, or more of the bacteria described in Section 5.7. In another specific embodiment, an anti-infective peptide described herein is not effective against vaginal microflora. For example, in a specific embodiment, an anti-infective peptide described herein has an MIC of >50 µM against a bacterium of the vaginal microflora. In a specific embodiment, an anti-infective peptide described herein is not effective against one, two, or more bacteria of the vaginal microenvironment. In a specific embodiment, a bacteria of the vaginal microenvironment is *Lactobacillus jensenii*. In a specific embodiment, a bacteria of the vaginal microenvironment is *Lactobacillus crispatus*. In a specific embodiment, a bacteria of the vaginal microenvironment is *Lactobacillus acidophilus*.

In a specific embodiment, an anti-infective peptide described herein is an amphipathic helix. In a specific embodiment, the anti-infective peptide is weakly helical. In a specific embodiment, an anti-infective peptide described herein has a fractional helicity between 0.1 to 0.5 in distilled water, and 0.1 to 0.6 in phosphate-buffered saline. Fractional helicity may be determined using any technique known to one of skill in the art or described herein. For example, circular dichroism may be used as follows: CD experiments are conducted on a AVIV Model 420 spectrometer (AVIV Biomedical, Lakewood, NJ, USA) using quartz curvette with a 1 mm path length (Hellma). Spectral data are collected with a step size of 0.5 nm and averaging time of 4 s. All spectra are recorded at 25° C. from 190 to 260 nm using a bandwidth of 1-nm and averaged over three scans. The CD spectra are recorded before and after the addition of 2.5 mM POPC lipid vesicles to 50 µM peptide. Baseline scans in buffer only or liposomes only are also performed using the same instrument settings, and this contribution was substracted from respective data scans with peptides. The corrected spectra are expressed in mean residue molar ellipticity ($\Theta$), and the fractional helicity of peptides is calculated as follows: fH=($[\Theta]_{222}$–3,000)/(–36,000–3000), where $[\Theta]_{222}$ is the molar ellipticity at 222 nm. See, e.g., J. D. Morrisett, J. S. David, H. J. Pownall, A. M. Gotto Jr, Interaction of an apolipoprotein (apoLP-alanine) with phosphatidylcholine. *Biochemistry* 12, 1290-1299 (1973), which is incorporated herein for a description of techniques for determining fractional helicity.

In a specific embodiment, an anti-infective peptide described herein undergoes significant helical induction (e.g., a greater than 20% increase) in zwitterionic lipid vesicles. In other words, there is a helicity increase from its secondary structure state in solution (in PBS) to its secondary structure state when inserted into lipid membranes (in PBS). If the helicity of a peptide becomes greater in the lipid membrane, it prefers to associate into the lipid membrane because it is more stable. In a specific embodiment, an anti-infective peptide undergoes a 21% to 50% or 21% to 30% increase helical induction in zwitterionic lipid vesicles. In another specific embodiment, an anti-infective peptide undergoes the helical induction set forth in Table 5 below in zwitterionic lipid vesicles. In a specific embodiment, an anti-infective peptide described herein is folded into an alpha-helical state in zwitterionic lipid vesicles. In a specific embodiment, an anti-infective peptide described herein has 83% helicity in zwitterionic lipid vesicles. In a specific embodiment, the helical induction is determined according to circular dichroism (see, e.g., Section 5.8). In other embodiments, the helical induction is determined using a protein algorithim or FTIR spectroscopy. See, e.g., Haris, Parvez I., and Dennis Chapman. "The conformational analysis of peptides using Fourier transform IR spectroscopy." Biopolymers 37.4 (1995): 251-263 for a description of the FTIR spectroscopy method.

TABLE 5

| Peptide | Fractional Helicity in PBS | Fractional Helicity in Liposome | Helical Induction Fraction | Helical Induction % |
|---|---|---|---|---|
| TSG001 (SEQ ID NO: 1) | 0.56 | 0.83 | 0.27 | 27 |
| TSG002 (SEQ ID NO: 2) | 0.42 | 0.64 | 0.22 | 22 |
| TSG003 (SEQ ID NO: 3) | 0.37 | 0.66 | 0.29 | 29 |
| TSG004 (SEQ ID NO: 4) | 0.24 | 0.51 | 0.27 | 27 |
| TSG005 (SEQ ID NO: 5) | 0.41 | 0.65 | 0.24 | 24 |
| TSG006 (SEQ ID NO: 6) | 0.17 | 0.26 | 0.09 | 9 |
| TSG007 (SEQ ID NO: 7) | 0.65 | 0.68 | 0.03 | 3 |
| TSG008 (SEQ ID NO: 8) | 0.38 | 0.56 | 0.18 | 18 |
| TSG009 (SEQ ID NO: 9) | 0.51 | 0.71 | 0.2 | 20 |

Without being bound by any particular theory, in a specific embodiment, an anti-infective peptide described herein acts as a membrane curvature sensor, which is preferentially active against highly curved membranes, such as, for example, small, enveloped viruses. For example, in a specific embodiment, the anti-infective peptide exhibits strong partitioning into zwitterionic lipid bilayers. In a specific embodiment, an anti-infective peptide described herein has a lipid-water partition coefficient (also known as partition constant) of approximately $10^5$ for high-curvature, zwitterionic lipid vesicles of less than 200 nm in diameter. In a specific embodiment, an anti-infective peptide described herein has negligible partitioning into larger vesicles. Negligible partitioning means a lipid-water partition coefficient of less than $1 \times 10^4$. In a specific embodiment, the partitioning of the peptide into zwitterionic 1-palmitoyl-2-oleoyl-sn-glycero-3-phosphocholine lipid bilayers is determined according to fluorescence spectroscopy (see, e.g., Section 5.8).

In a specific embodiment, an anti-infective peptide described herein is cationic. In a specific embodiment, an anti-infective peptide described herein has a net charge of +1. For example, each of TSG001 (SEQ ID NO:1), TSG002 (SEQ ID NO:2), TSG004 (SEQ ID NO:4), and TSG005 (SEQ ID NO:5) have a net charge of +1. In other specific embodiments, an anti-infective peptide described herein has a net charge of zero. For example, each of TSG003 (SEQ ID NO:3), TSG006 (SEQ ID NO:6), TSG007 (SEQ ID NO:7), TSG008 (SEQ ID NO:8), and TSG009 (SEQ ID NO:9) have a net charge of zero. In a specific embodiment, the anti-infective peptide is a peptide described in Table 2A, 2B or 4.

In a specific embodiment, an anti-infective peptide described herein has a low tendency to aggregate. The tendency to aggregate can be determined by absorbance measurements at 280 nm wavelength, which can determine the molar concentration of peptide based on the molar extinction coefficient that is defined by the number of tryptophans, tyrosines, and phenylalanines. A low tendency to aggregate (in other words, good dispersion) means that the peptide reconstitutes well in an aqueous solution (e.g., distilled water) and is defined as ≥60%, where is defined as experimental molar mass measured by absorbance measurements/theoretical molar mass based on dry mass and molecular weight×100%. In contrast, a high tendency to aggregate (in other words, bad dispersion) is defined as <60%, where % is defined as experimental molar mass measured by absorbance measurements divided by the theoretical molar mass, calculated based on the dry mass and molecular weight of the peptide, ×100%.

In a specific embodiment, an anti-infective peptide described herein has an EC50 described herein against a virus described in Section 5.7. One skilled in the art would recognize that "EC50" refers to the concentration of an active compound (e.g., an anti-infective peptide or composition described herein) required to yield the half-maximal response. In a specific embodiment, an anti-infective peptide described herein has an EC50 of between 0.1 μM and 20 μM. In a specific embodiment, the EC50 is between 0.1 μM and 2.5 μM, 0.1 μM and 5 μM, 0.1 μM and 10 μM, 0.1 μM and 15 μM, 0.1 μM and 20 μM, 1 μM and 2.5 μM, 1 μM and 5 μM, 1 μM and 15 μM, 1 μM and 15 μM, or 1 μM and 20 μM. In a specific embodiment, the EC50 is less than 20 μM, less than 15 μM, less than 10 μM, less than 5 μM, less than 2.5 μM, less than 1 μM, or less than 0.1 μM. In a specific embodiment, the EC50 is determined as described in Section 5.8 and/or Section 6.

In a specific embodiment, an anti-infective peptide described herein has an IC50 described herein against a virus described in Section 5.7. One skilled in the art would recognize that "IC50" refers to the concentration of an active compound (e.g., an anti-infective peptide or composition described herein) required to inhibit a given biological process or component of a biological process (e.g., a bacterial or viral infection) by half. In a specific embodiment, an anti-infective peptide described herein has an IC50 of between 0.1 μM and 20 μM. In a specific embodiment, the IC50 is between 0.1 μM and 2.5 μM, 0.1 μM and 5 μM, 0.1 μM and 10 μM, 0.1 μM and 15 μM, 0.1 μM and 20 μM, 1 μM and 2.5 μM, 1 μM and 5 μM, 1 μM and 10 μM, 1 μM and 15 μM, or 1 μM and 20 μM. In a specific embodiment, an anti-infective peptide described herein has an IC50 less than 20 μM, less than 15 μM, less than 10 μM, less than 5 μM, less than 2.5 μM, less than 1 μM, or less than 0.1 μM. In a specific embodiment, the IC50 is determined as described in Section 5.8 and/or Section 6.

In a specific embodiment, an anti-infective peptide described herein has a CC50 described herein. One skilled in the art would recognize that "CC50" refers to the concentration of an active compound (e.g., an anti-infective peptide or composition described herein) required to be cytotoxic to half of the cells in the treated population. In a specific embodiment, an anti-infective peptide described herein has an CC50 of between 1 μM and 200 μM in animal cells (e.g., human cells, such as human cells from a cell line). In a specific embodiment, the CC50 is between 10 μM and 25 μM, 10 μM and 50 μM, 10 μM and 100 μM, 10 μM and 150 μM, 10 μM and 200 μM, 15 μM and 25 μM, 15 μM and 50 μM, 15 μM and 100 μM, 15 μM and 150 μM, 15 μM and 200 μM, 25 μM and 50 μM, 25 μM and 100 μM, 25 μM and 150 μM, 25 μM and 200 μM, 50 μM and 75 μM, 50 μM and 100 μM, 50 μM and 125 μM, 50 μM and 150 μM, 50 μM and 200 μM, 75 μM, and 100 μM, 75 μM and 125 μM, 75 μM and 150 μM, 75 μM and 200 μM, 125 μM and 150 μM, 125 μM and 200 μM, or 150 μM and 200 μM μM in animal cells (e.g., human cells, such as human cells from a cell line). In a specific embodiment, an anti-infective peptide described herein has a CC50 greater than 10 μM, greater than 25 μM, greater than 50 μM, greater than 75 μM, greater than 100 μM, greater than 125 μM, or greater than 150 μM in animal cells (e.g., human cells, such as human cells from a cell line). In a specific embodiment, the CC50 is determined as described in Section 5.8 and/or Section 6.

In a specific embodiment, an anti-infective peptide described herein has a therapeutic index ("TI") described herein. One skilled in the art would recognize that a therapeutic index refers to a comparison of the amount of an active compound (e.g., an anti-infective peptide or composition described herein) required to be have a therapeutic effect to the amount of an active compound (e.g., an anti-infective peptide or composition described herein) that causes toxicity. In a specific embodiment, an anti-infective peptide described herein has a TI of between 1 and 150. In a specific embodiment, the TI is between 2 and 5, 2 and 10, 2 and 15, 2 and 20, 20 and 25, 10 and 25, 10 and 50, 10 and 100, 10 and 125, 10 and 150, 25 and 50, 25 and 100, 25 and 125, 25 and 150, 50 and 75, 50 and 100, 50 and 125, 50 and 150, 75 and 100, 75 and 125, or 75 and 150. In a specific embodiment, an anti-infective peptide described herein has a TI greater than 10, greater than 25, greater than 50, greater than 75, greater than 100, or greater than 125. In a specific embodiment, an anti-infective peptide described herein has a TI of between 1 and 150. In a specific embodiment, the TI is between 2 and 5, 2 and 10, 2 and 15, 2 and 20, 20 and 25, 10 and 25, 10 and 50, 10 and 100, 10 and 125, 10 and 150, 25 and 50, 25 and 100, 25 and 125, 25 and 150, 50 and 75, 50 and 100, 50 and 125, 50 and 150, 75 and 100, 75 and 125, or 75 and 150 against Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2). In a specific embodiment, an anti-infective peptide described herein has a TI greater than 10, greater than 25, greater than 50, greater than 75, greater than 100, or greater than 125 Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2). In a specific embodiment, the TI is determined as described in Section 5.8 and/or Section 6.

In certain embodiments, an anti-infective peptide described herein is not effective as an antiviral agent for an infection with a virus of the Orthomyxoviridae family. In a specific embodiment, anti-infective peptide described herein is not effective as an antiviral agent for an influenza A virus infection. In some embodiments, anti-infective peptide described herein is not effective as an antiviral agent for a herpes simplex virus 1 (HSV-1) infection (e.g., infection by an HSV-1 described in Kern et al., Antimicrob Agents Chemother. 49(3): 1039-1045 (2005)). In some embodiments, anti-infective peptide described herein is not effective as an antiviral agent for a LaCrosse encephalitis virus (LACY) infection (e.g., infection with LACV H44-71017, such as in GenBank Accession No. DQ380208.1).

In certain embodiments, an anti-infective peptide described herein is effective as an antiviral agent for an infection with a virus of the Orthomyxoviridae family. In a specific embodiment, anti-infective peptide described herein is effective as an antiviral agent for an influenza A virus infection. In some embodiments, anti-infective peptide described herein is effective as an antiviral agent for a herpes simplex virus 1 (HSV-1) infection (e.g., infection by an HSV-1 described in Kern et al., Antimicrob Agents Chemother. 49(3): 1039-1045 (2005)). In some embodiments, anti-infective peptide described herein is effective as an antiviral agent for a LaCrosse encephalitis virus (LACV) infection (e.g., infection with LACV H44-71017, such as in GenBank Accession No. DQ380208.1).

In a specific embodiment, an anti-infective peptide described herein has a hemotoxicity level, for example, hemolysis activity, described herein. One skilled in the art would recognize that hemolysis activity (calculated as, for example, minimal hemolytic concentration ("MHC")), refers to the minimal concentration of an active compound (e.g., an anti-infective peptide or composition herein) required to lyse red blood cells. In a specific embodiment, the hemolysis activity is the minimum hemolysis concentration. In a specific embodiment, an anti-infective peptide described herein has an MHC of between 0.5 μM and 100 μM. In a specific embodiment, the MHC is between 0.5 μM and 10 μM, 0.5 μM and 25 μM, 0.5 μM and 50 μM, 0.5 μM and 100 μM, 1 μM and 5 μM, 1 μM and 10 μM, 1 μM and 25 μM, 1 μM and 50 μM, 1 μM and 100 μM, 10 μM and 15 μM, 10 μM and 25 μM, 10 μM and 50 μM, 10 μM and 100 μM, 10 μM and 15 μM, 20 μM and 30 μM, 20 μM and 50 μM, 20 μM and 100 μM, 50 μM and 75 μM, or 50 μM and 100 μM. In a specific embodiment, an anti-infective peptide described herein has an MHC greater than 2 μM, greater than 5 μM, greater than 10 μM, greater than 25 μM, greater than 50 μM, or greater than 75 μM. In a specific embodiment, the MHC is determined as described in Section 5.8 and/or Section 6.

In a specific embodiment, an anti-infective peptide described herein has a minimum inhibitory concentration ("MIC") described herein against a bacteria described in Section 5.7. One skilled in the art would recognize that MIC refers to the minimum concentration of an active compound (e.g., an anti-infective peptide or composition described herein) required to prevent visible growth of bacterium. In a specific embodiment, an anti-infective peptide described herein has an MTC of between 0.1 μM and 20 μM. In a specific embodiment, an anti-infective peptide described herein has an MIC between 0.1 μM and 2.5 μM, 0.1 μM and 5 μM, 0.1 μM and 10 μM, 0.1 μM and 15 μM, 0.1 μM and 20 μM, 1 μM and 2.5 μM, 1 μM and 5 μM, 1 μM and 15 μM, 1 μM and 15 μM, or 1 μM and 20 μM. In a specific embodiment, an anti-infective peptide described herein has an MIC less than 20 μM, less than 15 μM, less than 10 μM, less than 5 μM, less than 2.5 μM, or less than 1 μM. In a specific embodiment, an anti-infective peptide described herein has an MIC of between 0.1 μg/mL and 64 μg/mL. In a specific embodiment, an anti-infective peptide described herein has an MIC between 0.1 μg/mL and 2.5 μg/mL, 0.1 μg/mL and 5 μg/mL, 0.1 μg/mL and 10 μg/mL, 0.1 μg/mL and 15 μg/mL, 0.1 μg/mL and 20 μg/mL, 1 μg/mL and 2.5 μg/mL, 1 μg/mL and 5 μg/mL, 1 μg/mL and 15 μg/mL, 1 μg/mL and 15 μg/mL, or 1 μg/mL and 20 μg/mL. In a specific embodiment, an anti-infective peptide described herein has an MIC less than 20 µg/mL, less than 15 µg/mL, less than 10 µg/mL, less than 5 µg/mL, less than 2.5 µg/mL, or less than 1 µg/mL. In a specific embodiment, an anti-infective peptide described herein has an MIC between 20 µg/mL and 25 µg/mL, 20 µg/mL and 30 µg/mL, 20 µg/mL and 35 µg/mL, 20 µg/mL and 40 µg/mL, 20 µg/mL and 45 µg/mL, 20 µg/mL and 50 µg/mL, 20 µg/mL and 55 µg/mL, 20 µg/mL and 60 µg/mL, or 20 µg/mL and 64 µg/mL. In a specific embodiment, an anti-infective peptide described herein has an MIC less than 64 µg/mL, less than 55 µg/mL, less than 45 µg/mL, less than 35 µg/mL, or less than 25 µg/mL. In a specific embodiment, the MIC is determined as described in Section 5.8 and/or Section 6.

In a specific embodiment, an anti-infective peptide comprises of the amino acid sequence set forth in Table 2A, Table 2B, or Table 4 and is 16 to 24 amino acid residues in length, and exhibits (i) a CC50 of between 15 µM and 200 µM in human cells (e.g., human cells from a human cell line, such as Caski, HEC1A, Caco-2, and ME180, or nonhuman cells from nonhuman cell lines, such as, Vero, MDCK or MCBK cells) as measured by a technique known to one of skill in the art or described herein, (ii) an MHC of between 2 µM and 100 µM on human erythrocyte cells as measured by a technique known to one of skill in the art or described herein, and (iii) a TI of between 1 and 150. In a specific embodiment, the TI is between 2 and 5, 2 and 10, 2 and 15, 2 and 20, 20 and 25, 10 and 25, 10 and 50, 10 and 100, 10 and 125, 10 and 150, 25 and 50, 25 and 100, 25 and 125, 25 and 150, 50 and 75, 50 and 100, 50 and 125, 50 and 150, 75 and 100, 75 and 125, or 75 and 150 against Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2). In another specific embodiment, an anti-infective peptide consists of the amino acid sequence set forth in Table 2A, Table 2B, or Table 4 and exhibits (i) a CC50 of between 15 µM an 200 µM in human cells (e.g., human cells from a human cell lines, such as Caski, HEC1A, Caco-2, and ME180, or nonhuman cells from nonhuman cell lines, such as, Vero, MDCK or MCBK cells) as measured by a technique known to one of skill in the art or described herein, (ii) an MHC of between 2 µM and 100 µM on human erythrocyte cells as measured by a technique known to one of skill in the art or described herein, and (iii) a TI of between 1 and 150. In a specific embodiment, the TI is between 2 and 5, 2 and 10, 2 and 15, 2 and 20, 20 and 25, 10 and 25, 10 and 50, 10 and 100, 10 and 125, 10 and 150, 25 and 50, 25 and 100, 25 and 125, 25 and 150, 50 and 75, 50 and 100, 50 and 125, 50 and 150, 75 and 100, 75 and 125, or 75 and 150 against Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2). In accordance with these embodiments, the anti-infective peptide, in certain embodiments, exhibits an MIC of between 0.1 µM and 20 µM against *Staphylococcus aureus* (e.g., methicillin-sensitive and methicillin-resistant), *enterococci* (e.g., vancomycin-sensitive and Vancomycin-resistant), *streptococci* (e.g., penicillin-sensitive and penicillin-resistant), *Bacillus anthracis, Pseudomonas aeruginosa, Moraxella catarrhalis, Haemophilus influenzae, Clostridium difficile*, and *Propionibacterium acnes*. In accordance with these embodiments, the anti-infective peptide, in certain embodiments, exhibits an MIC of between 0.1 µg/mL and 20 µg/mL against *Staphylococcus aureus* (e.g., methicillin-sensitive and methicillin-resistant), *enterococci* (e.g., vancomycin-sensitive and Vancomycin-resistant), *streptococci* (e.g., penicillin-sensitive and penicillin-resistant), *Bacillus anthracis, Pseudomonas aeruginosa, Moraxella catarrhalis, Haemophilus influenzae, Clostridium difficile*, and *Propionibacterium acnes*.

In a specific embodiment, an anti-infective peptide comprises of the amino acid sequence set forth in Table 2A, Table 2B, or Table 4 and is 16 to 24 amino acid residues in length, and exhibits (i) an MTC of between 0.1 µM and 20 µM as measured by a technique known to one of skill in the art or described herein, and (ii) a TI of between 1 and 100. In a specific embodiment, the TI is between 2 and 5, 2 and 10, 2 and 15, 2 and 20, 20 and 25, 10 and 25, 10 and 50, 10 and 100, 10 and 125, 10 and 150, 25 and 50, 25 and 100, 25 and 125, 25 and 150, 50 and 75, or 50 and 100 against *Staphylococcus aureus* (e.g., methicillin-sensitive and methicillin-resistant), *enterococci* (e.g., vancomycin-sensitive and Vancomycin-resistant), *streptococci* (e.g., penicillin-sensitive and penicillin-resistant), *Bacillus anthracis, Pseudomonas aeruginosa, Moraxella catarrhalis, Haemophilus influenzae, Clostridium difficile*, and *Propionibacterium acnes*. In accordance with these embodiments, the anti-infective peptide, in certain embodiments, exhibits an MIC of between 0.1 µg/mL and 20 µg/mL against *Staphylococcus aureus* (e.g., methicillin-sensitive and methicillin-resistant), *enterococci* (e.g., vancomycin-sensitive and Vancomycin-resistant), *streptococci* (e.g., penicillin-sensitive and penicillin-resistant), *Bacillus anthracis, Pseudomonas aeruginosa, Moraxella catarrhalis, Haemophilus influenzae, Clostridium difficile*, and *Propionibacterium acnes*. In a specific embodiment, an anti-infective peptide consists of the amino acid sequence set forth in Table 2A, Table 2B, or Table 4 and exhibits (i) an MIC of between 0.1 µM and 20 µM as measured by a technique known to one of skill in the art or described herein, and (ii) a TI of between 1 and 100. In a specific embodiment, the TI is between 2 and 5, 2 and 10, 2 and 15, 2 and 20, 20 and 25, 10 and 25, 10 and 50, 10 and 100, 10 and 125, 10 and 150, 25 and 50, 25 and 100, 25 and 125, 25 and 150, 50 and 75, or 50 and 100 against *Staphylococcus aureus* (e.g., methicillin-sensitive and methicillin-resistant), *enterococci* (e.g., vancomycin-sensitive and Vancomycin-resistant), *streptococci* (e.g., penicillin-sensitive and penicillin-resistant), *Bacillus anthracis, Pseudomonas aeruginosa, Moraxella catarrhalis, Haemophilus influenzae, Clostridium difficile*, and *Propionibacterium acnes*. In accordance with these embodiments, the anti-infective peptide, in certain embodiments, exhibits an MIC of between 0.1 µg/mL and 20 µg/mL against *Staphylococcus aureus* (e.g., methicillin-sensitive and methicillin-resistant), *enterococci* (e.g., vancomycin-sensitive and Vancomycin-resistant), *streptococci* (e.g., penicillin-sensitive and penicillin-resistant), *Bacillus anthracis, Pseudomonas aeruginosa, Moraxella catarrhalis, Haemophilus influenzae, Clostridium difficile*, and *Propionibacterium acnes*. In accordance with these embodiments, the anti-infective peptide, in certain embodiments, exhibits a TI of between 2 and 5, 2 and 10, 2 and 15, 2 and 20, 20 and 25, 10 and 25, 10 and 50, 10 and 100, 10 and 125, 10 and 150, 25 and 50, 25 and 100, 25 and 125, 25 and 150, 50 and 75, 50 and 100, 50 and 125, 50 and 150, 75 and 100, 75 and 125, or 75 and 150 against Dengue serotype 1 (e.g., Dengue serotype 1

PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241). Chikungunya virus (e.g., Chikungunya virus 181/25), Yellow Fever Virus (e.g., Yellow Fever Virus 17D), and Japanese encephalitis virus (e.g., Japanese encephalitis virus 14-14-2).

In a specific embodiment, an anti-infective peptide described herein is soluble (e.g., highly soluble) in distilled water. The solubility of an anti-infective peptide in distilled water or another aqueous solution may be determined by any technique known to one of skill in the art or described herein (see, Section 6). In a specific embodiment, at least 80%, 85%, 90% or more of an anti-infective peptide described herein reconstitutes in distilled water using a technique known to one of skill in the art or described herein.

In a specific embodiment, an anti-infective peptide described herein is non-immunogenic or has low immunogenicity. Any technique known to one of skill in the art can be used to assess the immunogenicity of an anti-infective peptide.

In a specific embodiment, an anti-infective peptide described herein acts via a membrane-disrupting mechanism. Examples of membrane-disrupting mechanism include one or more of the following: pore formation in membranes, membrane solubilization, impairment of membrane fluidity, coating the membrane surface, and any process resulting in morphological changes in membrane structure or function of pathogenic proteins or sugars in the membrane. These processes can be enacted by physical and/or chemical processes.

In a specific embodiment, the anti-infective peptide is an anti-infective peptide described in Section 6. In a specific embodiment, the anti-infective peptide is pegylated or modified as described in Section 5.2. In a specific embodiment, the anti-infective peptide is synthesized as described in Section 5.3. In a specific embodiment, the anti-infective peptide is formulated as part of a composition as described in Section 5.4. In a specific embodiment, the anti-infective peptide is used in a method described in Section 5.5. In a specific embodiment, the anti-infective peptide is used in an assay described in Section 5.8. In a specific embodiment, the anti-infective peptide is a component of a kit described in 5.9.

In some embodiments, an anti-infective peptide described herein is multimerized. The multimer may comprise two, three or more anti-infective peptides.

In one embodiment, an anti-infective peptide is a peptide described in Table 2A. In one embodiment, an anti-infective peptide is a peptide described in Table 2B. In one embodiment, an anti-infective peptide is a peptide in Table 4.

In one embodiment, an anti-infective peptide described herein is isolated. In another embodiment, an anti-infective peptide described herein is synthetic.

5.2 Pegylated Anti-Infective Peptides

In a specific embodiment, an anti-infective peptide described herein (see Section 5.1 and Section 6) is modified with a polyethylene glycol (PEG) polymer(s) (the term "anti-infective peptide," as used herein, includes a peptide described in Sections 5.1 and 6 as well as pegylated forms thereof). For example, in a specific embodiment, an anti-infective peptide described herein is linked to one, two, or more PEG polymers. In a specific embodiment, an anti-infective peptide described herein is linked to one, two, or more PEG polymers, wherein the peptide comprises, consists essentially of or consists of an amino acid sequence set forth in Table 2A or Table 2B. In a specific embodiment, an anti-infective peptide described herein is linked to one, two, or more PEG polymers, wherein the peptide comprises, consists essentially of or consists of an amino acid sequence set forth in Table 4. In certain embodiments, the PEG polymer(s) is covalently linked to the peptide. In other embodiments, the PEG polymer(s) is non-covalently linked to the peptide. In specific embodiments, the PEG polymer(s) is directly linked to the peptide. In other embodiments, the PEG polymer(s) is linked indirectly to the peptide. In a specific embodiment, the PEG polymer(s) is in the molecular weight range of 500 to 1,000 daltons, 500 to 2,000 daltons, 500 to 3,000 daltons, 500 to 4,000 daltons, or 500 to 5,000 daltons. In a specific embodiment, the PEG polymer is in the molecular weight range or 1,000 to 5,000 daltons, 2,000 to 5,000 daltons, 3,000 to 5,000 daltons, or 4,000 to 5,000 daltons. In another embodiment, the PEG polymer(s) is in the molecular weight range of 500 to 5,000 daltons. The PEG polymer(s) may be branched, non-branched or forked. In certain embodiments, one, two or more of the PEG polymers is branched. In some embodiments, one, two or more of the PEG polymers is non-branched. In certain embodiments, one, two or more of the PEG polymers is forked.

In a specific embodiment, an anti-infective peptide described herein contains one PEG monomer. In a specific embodiment, an anti-infective peptide described herein contains oligomerized PEG (PEG polymer). In a specific embodiment, an anti-infective peptide described herein contains between 2 and hundreds of PEG monomers. In a specific embodiment, an anti-infective peptide described herein contains 1-5, 5-10, 10-15, 15-20, 10-20, 20-25, 20-30, 30-40, 40-50, 50-60, 60-70, 70-80, 80-90, 90-100, or 100-200 PEG units. In a specific embodiment, an anti-infective peptide described herein contains 24 PEG monomers. In a specific embodiment, an anti-infective peptide described herein contains two PEG polymers, wherein each PEG polymer comprises 12 PEG monomers.

An anti-infective peptide described herein may be linked to one, two, or more PEG polymers at, for example, the N-terminus of the peptide, the C-terminus of the peptide, a lysine residue in the peptide, or an arginine residue in the peptide. In a specific embodiment, the one, two, or more PEG polymers is linked to the N-terminus of the peptide. In another specific embodiment, the one, two, or more PEG polymers is linked to the C-terminus of the peptide. In another specific embodiment, the one, two, or more PEG polymers is linked to a lysine residue in the peptide. In another specific embodiment, the one, two, or more PEG polymer is linked to an arginine residue in the peptide. In certain embodiments, an anti-infective peptide described herein is linked to two or more PEG polymers at two or more of the following: the N-terminus of the peptide, the C-terminus of the peptide, a lysine residue in the peptide, and/or an arginine residue in the peptide.

In a specific embodiment, an anti-infective peptide comprising, consisting essentially of or consisting of the amino acid sequence SGSWLRDVWTWLQSKL (SEQ ID NO: 1) contains a 24-unit PEG polymer attached at the N-terminus of the anti-infective peptide. In another specific embodiment, an anti-infective peptide comprising, consisting essentially of or consisting of the amino acid sequence GSSWLRDVWTWLQSKL (SEQ ID NO:2) contains a 24-unit PEG polymer attached at the N-terminus of the anti-infective peptide. In another specific embodiment, an anti-infective peptide comprising, consisting essentially of or consisting of the amino acid sequence GSSWLRDVWTWLQSAL (SEQ ID NO:3) contains a 24-unit PEG polymer attached at the N-terminus of the anti-infective peptide. In another specific embodiment, an anti-infective peptide comprising, consisting essentially of or consisting of the amino acid sequence GSSWLRDV WTKLQSWL (SEQ ID NO:4) contains a 24-unit PEG polymer attached at the N-terminus of the anti-infective peptide. In another specific embodiment, an anti-infective peptide comprising, consisting essentially of or consisting of the amino acid sequence GSS-WLRDIWTALQSWL (SEQ ID NO:6) contains a 24-unit PEG polymer attached at the N-terminus of the anti-infective peptide.

In a specific embodiment, an anti-infective peptide comprising, consisting essentially of or consisting of the amino acid sequence SGSWLRDVWTWLQSKL (SEQ ID NO: 1) contains two 12-unit PEG polymers attached at the N-terminus of the anti-infective peptide. In another specific embodiment, an anti-infective peptide comprising, consisting essentially of or consisting of the amino acid sequence GSSWLRDVWTWLQSKL (SEQ ID NO:2) contains two 12-unit PEG polymers attached at the N-terminus of the anti-infective peptide. In another specific embodiment, an anti-infective peptide comprising, consisting essentially of or consisting of the amino acid sequence GSS-WLRDVWTWLQSAL (SEQ ID NO:3) contains two 12-unit PEG polymers attached at the N-terminus of the anti-infective peptide. In another specific embodiment, an anti-infective peptide comprising, consisting essentially of or consisting of the amino acid sequence GSS-WLRDVWTKLQSWL (SEQ ID NO:4) contains two 12-unit PEG polymers attached at the N-terminus of the anti-infective peptide. In another specific embodiment, an anti-infective peptide comprising, consisting essentially of or consisting of the amino acid sequence GSS-WLRDIWTALQSWL (SEQ ID NO:6) contains two 12-unit PEG polymers attached at the N-terminus of the anti-infective peptide. As used herein, "PEG12" refers to a PEG polymer of 12 PEG monomeric units.

In a specific embodiment, a pegylated peptide comprises the following structure: $NH_2$-PEG12-Amide-PEG12-peptide, wherein the peptide is 16 to 24 amino acid residues in length and comprises an amino acid sequence set forth in Table 2A or Table 2B. In a specific embodiment, a pegylated peptide comprises the following structure: $NH_2$-PEG12-Amide-PEG12-peptide, wherein the peptide consists of an amino acid sequence set forth in Table 2A or Table 2B. In a specific embodiment, a pegylated peptide comprises the following structure: $NH_2$-PEG12-Amide-PEG12-peptide, wherein the peptide is 16 to 24 amino acid residues in length and comprises an amino acid sequence set forth in Table 4. In a specific embodiment, a pegylated peptide comprises the following structure: $NH_2$-PEG12-Amide-PEG12-peptide, wherein the peptide consists of an amino acid sequence set forth in Table 4. In certain embodiments, the peptide is amidated at the C-terminus.

In a specific embodiment, a pegylated peptide comprises the following structure: $NH_2$-PEG12-Amide-PEG12-peptide-$NH_2$, wherein the peptide is 16 to 24 amino acid residues in length and comprises an amino acid sequence set forth in Table 2A or Table 2B. In a specific embodiment, a pegylated peptide comprises the following structure: $NH_2$-PEG12-Amide-PEG12-peptide-$NH_2$, wherein the peptide consists of an amino acid sequence set forth in Table 2A or Table 2B. In a specific embodiment, a pegylated peptide comprises the following structure: $NH_2$-PEG12-Amide-PEG12-peptide-$NH_2$, wherein the peptide is 16 to 24 amino acid residues in length and comprises an amino acid sequence set forth in Table 4. In a specific embodiment, a pegylated peptide comprises the following structure: $NH_2$-PEG12-Amide-PEG12-peptide-$NH_2$, wherein the peptide consists of an amino acid sequence set forth in Table 4. In certain embodiments, the peptide is amidated at the C-terminus.

In a specific embodiment, a pegylated peptide comprises the following structure: $NH_2$-PEG12-Amide-PEG12-peptide-COOH, wherein the peptide is 16 to 24 amino acid residues in length and comprises an amino acid sequence set forth in Table 2A or Table 2B. In a specific embodiment, a pegylated peptide comprises the following structure: $NH_2$-PEG12-Amide-PEG12-peptide-COOH, wherein the peptide consists of an amino acid sequence set forth in Table 2A or Table 2B. In a specific embodiment, a pegylated peptide comprises the following structure: $NH_2$-PEG12-Amide-PEG12-peptide-COOH, wherein the peptide is 16 to 24 amino acid residues in length and comprises an amino acid sequence set forth in Table 4. In a specific embodiment, a pegylated peptide comprises the following structure: $NH_2$-PEG12-Amide-PEG12-peptide-COOH, wherein the peptide consists of an amino acid sequence set forth in Table 4.

In certain embodiments, a hydrophilic polymer is added to an anti-infective peptide. A hydrophilic polymer may be linked (directly or indirectly) to an anti-infective peptide. In a specific embodiment, a linker (e.g., a 1-5, 5-10 or 1-10 amino acid linker, such as a glycine linker) is used to link a hydrophilic polymer to an anti-infective peptide. A hydrophilic polymer may be covalently or non-covalently linked to an anti-infective peptide. A hydrophilic polymer may be a basically unstructured, hydrophilic amino acid polymer that is a functional analog of PEG. Examples of hydrophilic polymers include XTEN (Amunix; it is 864 amino acids long and comprised of six amino acids (A, E, G, P, S and T)), PAS (XL-Protein GmbH; A random coil polymer comprised of an even more restricted set of only three small uncharged amino acids, proline, alanine and serine), poly(methacrylate), polyvinylpyrrolidone, polyvinyl alcohol, polyacrylic acid, polyacrylamides, N-(2-Hydroxypropyl) methacrylamide (HPMA), Divinyl Ether-Maleic Anhydride (DIVEMA), polyoxazoline, polyphosphates, polyphosphazenes, and derivatives of conventional PEG (e.g., hydroxy-PEG). In certain embodiments, two, three or more hydrophilic polymers are liked to an anti-infective peptide. The hydrophilic polymer(s) may be linked to the peptide at the C-terminus, N-terminus or at both the C-terminus and N-terminus.

In a specific embodiment, the pegylation of an anti-infective peptide described herein (e.g., in Sections 5.1 and 6) or the addition of a hydrophilic polymer to an anti-infective peptide described herein increases the half-life of the peptide in vivo as assessed by techniques known to one of skill in the art. See, e.g., Bird, Gregory H., et al. "Hydrocarbon double-stapling remedies the proteolytic instability of a lengthy peptide therapeutic." Proceedings of the National Academy of Sciences 107.32 (2010): 14093-14098, which is incorporated herein by reference, for a description of techniques for assessing the half-life of a peptide. For example, one non-human animal (e.g., mice) may be administered a certain concentration of an anti-infective peptide and another non-human animal of the same species (e.g., mice) may be administered the same anti-infective peptide that is pegylated or includes a hydrophilic polymer. At various time points after administration of the peptides, blood may be drawn from each animal and the concentration of peptide in the blood from each animal at each time point may be assessed by, e.g., liquid chromatography/mass spectrometry (LC/MS).

In certain embodiments, the pegylation of an anti-infective peptide described herein (e.g., in Sections 5.1 and 6) or the addition of a hydrophilic polymer to an anti-infective peptide described herein increases the half-life of the peptide in vivo by 2 to 5 times, 2 to 10 times, 2 to 20 times, 2 to 25 times, 2 to 50 times, 2 to 75 times, or 2 to 100 times as assessed by techniques known to one of skill in the art. In some embodiments, the pegylation of an anti-infective peptide described herein (e.g., in Sections 5.1 and 6) or the addition of a hydrophilic polymer to an anti-infective peptide described herein increases the half-life of the peptide in vivo by 5 to 10 times, 5 to 20 times, 5 to 25 times, 5 to 50 times, 5 to 75 times, or 5 to 100 times as assessed by techniques known to one of skill in the art. In certain embodiments, the pegylation of an anti-infective peptide described herein (e.g., in Sections 5.1 and 6) or the addition of a hydrophilic polymer to an anti-infective peptide described herein increases the half-life of the peptide in vivo by 10 to 20 times, 10 to 25 times, 10 to 50 times, 10 to 75 times, or 10 to 100 times as assessed by techniques known to one of skill in the art. In some embodiments, the pegylation of an anti-infective peptide described herein (e.g., in Sections 5.1 and 6) or the addition of a hydrophilic polymer to an anti-infective peptide described herein increases the half-life of the peptide in vivo by 25 times to 50 times, 25 to 75 times, or 25 to 100 times as assessed by techniques known to one of skill in the art. In certain embodiments, the pegylation of an anti-infective peptide described herein (e.g., in Sections 5.1 and 6) or the addition of a hydrophilic polymer to an anti-infective peptide described herein increases the half-life of the peptide in vivo by 50 to 75 times or 2 to 100 times as assessed by techniques known to one of skill in the art.

In specific embodiments, the pegylation of an anti-infective peptide described herein (e.g., in Sections 5.1 and 6) or the addition of a hydrophilic polymer to an anti-infective peptide described herein does not increase the EC50 of the peptide against an enveloped virus (e.g., Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2), Ebola virus and/or Marburg virus) by more than 2 to 5 times, 2 to 10 times, 2 to 20 times, 2 to 25 times, 2 to 50 times or 2 to 75 times as assessed by techniques known to one of skill in the art or described herein. In some specific embodiments, the pegylation of an anti-infective peptide described herein (e.g., in Sections 5.1 and 6) or the addition of a hydrophilic polymer to an anti-infective peptide described herein does not increase the EC50 of the peptide against an enveloped virus (e.g., Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2), Ebola virus and/or Marburg virus) by more than 5 to 10 times, 5 to 20 times, 5 to 25 times, 5 to 50 times or 5 to 75 times as assessed by techniques known to one of skill in the art or described herein. In certain specific embodiments, the pegylation of an anti-infective peptide described herein (e.g., in Sections 5.1 and 6) or the addition of a hydrophilic polymer to an anti-infective peptide described herein does not increase the EC50 of the peptide against an enveloped virus (e.g., Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2), Ebola virus and/or Marburg virus) by more than 10 to 20 times, 2 to 25 times, 10 to 50 times or 10 to 75 times as assessed by techniques known to one of skill in the art or described herein. In some specific embodiments, the pegylation of an anti-infective peptide described herein (e.g., in Sections 5.1 and 6) or the addition of a hydrophilic polymer to an anti-infective peptide described herein does not increase the EC50 of the peptide against an enveloped virus (e.g., Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2). Ebola virus and/or Marburg virus) by more than 25 to 50 times or 25 to 75 times as assessed by techniques known to one of skill in the art or described herein.

In a specific embodiment, the pegylation of a peptide comprising, consisting essentially of or consisting of SGSWLRDVWTWLQSKL (SEQ ID NO:1) increases the EC50 of the peptide against an enveloped virus (e.g., Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2), Ebola virus and/or Marburg virus) by the approximate amount set forth in Section 6 using an assay described herein or known to one skilled in the art. In another specific embodiment, the pegylation of a peptide comprising, consisting essentially of or consisting of GSSWLRDVWTWLQSKL (SEQ ID NO:2) increases the EC50 of the peptide against an enveloped virus (e.g., Dengue serotype (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2), Ebola virus and/or Marburg virus) by the approximate amount set forth in Section 6 using an assay described herein or known to one skilled in the art.

In a specific embodiment, the addition of a hydrophilic polymer to a peptide comprising, consisting essentially of or consisting of SGSWLRDVWTWLQSKL (SEQ ID NO:1) increases the EC50 of the peptide against an enveloped virus (e.g., Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2), Ebola virus and/or Marburg virus) by the approximate amount set forth in Section 6 using an assay described herein or known to one skilled in the art. In another specific embodiment, the addition of a hydrophilic polymer to a peptide comprising, consisting essentially of or consisting of GSSWLRDVWTWLQSKL (SEQ ID NO:2) increases the EC50 of the peptide against an enveloped virus (e.g., Dengue serotype 1 (e.g., Dengue serotype 1 PRS41393), Dengue serotype 2 (e.g., Dengue serotype 2 New Guinea C), Dengue serotype 3 (e.g., Dengue serotype 3 H87), Dengue serotype 4 (e.g., Dengue serotype 4 H241), Chikungunya virus (e.g., Chikungunya virus 181/25), Yellow Fever Virus (e.g., Yellow Fever Virus 17D), and Japanese encephalitis virus (e.g., Japanese encephalitis virus 14-14-2), Ebola virus and/or Marburg virus) by the approximate amount set forth in Section 6 using an assay described herein or known to one skilled in the art.

As used herein, the term "about" or "approximately" when used in conjunction with a number refers to any number within 1, 5 or 10% of the referenced number. In certain embodiments, the term "about" or "approximately" refers the exact number recited.

An anti-infective peptide described herein (see, e.g., Sections 5.1 and 6) can be linked to one, two, or more PEG polymers by any method known in the art for the pegylation of peptides, or by any method described herein (see, e.g., Section 6). An anti-infective peptide described herein (see, e.g., Sections 5.1 and 6) can be linked to one, two or more hydrophilic polymers using techniques known to one of skill in the art. The methods provided herein encompass, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art.

In a specific embodiment, an anti-infective peptide described in Section 5.1 is pegylated by any technique known to one of skill in the art or described herein. In another specific embodiment, an anti-infective peptide described in Section 6 is pegylated by any technique known to one of skill in the art or described herein. In another specific embodiment, the pegylated anti-infective peptide is synthesized as described in Section 5.3. In a specific embodiment, the pegylated anti-infective peptide is formulated as part of a composition as described in Section 5.4. In a specific embodiment, the pegylated anti-infective peptide is used in a method described in Section 5.5. In a specific embodiment, the pegylated anti-infective peptide is used in an assay described in Section 5.8. In a specific embodiment, the pegylated anti-infective peptide is a component of a kit described in 5.9.

In a specific embodiment, an anti-infective peptide linked to one, two, or more hydrophilic polymers is formulated as part of a composition as described in Section 5.4. In a specific embodiment, an anti-infective peptide linked to one, two, or more hydrophilic polymers is used in a method described in Section 5.5. In a specific embodiment, an anti-infective peptide linked to one, two, or more hydrophilic polymers is used in an assay described in Section 5.8. In a specific embodiment, an anti-infective peptide linked to one, two, or more hydrophilic polymers is a component of a kit described in 5.9.

In one embodiment, an anti-infective peptide described herein is isolated. In another embodiment, an anti-infective peptide described herein is synthetic.

5.3 Synthesis of Anti-Infective Peptides

An anti-infective peptide described herein (see, e.g., Section 5.1, Section 5.2, and Section 6) can be produced by any method known in the art for the synthesis of peptides, in particular, by chemical synthesis or recombinant expression techniques, or by any method described herein (see, e.g., Section 6). The methods provided herein encompass, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, NY; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

In a specific embodiment, an anti-infective peptide described herein is produced synthetically. The anti-infective peptides described herein may be prepared using conventional step-wise solution or solid phase synthesis (see, e.g., Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein).

Alternatively, the anti-infective peptides described herein may be prepared by way of segment condensation, as described, for example, in Liu et al., 1996, Tetrahedron Lett. 37(7):933-936; Baca, et al., 1995, J. Am. Chem. Soc. 117:1881-1887; Tam et al., 1995, Int. J. Peptide Protein Res. 45:209-216; Schnolzer and Kent, 1992, Science 256:221-225; Liu and Tam, 1994, J. Am. Chem. Soc. 116(10):4149-4153; Liu and Tam, 1994, Proc. Natl. Acad. Sci. USA 91:6584-6588; Yamashiro and Li, 1988, Int. J. Peptide Protein Res. 31:322-334. Other methods useful for synthesizing the anti-infective peptides described herein are described in Nakagawa et al., 1985, J. Am. Chem. Soc. 107:7087-7092.

In a specific embodiment, the anti-infective peptide is generated by standard F-moc solid phase synthesis. For example, the anti-infective peptide is generated by standard F-moc solid phase synthesis and purified by reverse-phase, high-performance liquid chromatography. The molecular weight of the purified peptide is determined by MALDI mass spectrometry. Lyophilized peptide samples are kept at −20° C. for long-term storage. Aliquots are prepared by solubilizing the peptide in deionized water at room temperature to a stock concentration of 2 mg/mL, and then stored at −20° C. until use. The molar concentration of the peptide in solution is estimated by taking into account the molar extinction coefficient of each aromatic tryptophan residue present in the amino acid sequence, as determined by absorbance measurements at 280 nm.

Anti-infective peptides comprising linkers can be synthesized by adding the linker(s) to the anti-infective peptide chain at the appropriate step in the synthesis. Suitable protecting schemes and chemistries are well known, and will be apparent to those of skill in the art.

In certain embodiments, an anti-infective peptide is recombinantly produced. In a specific embodiment, provided herein is a nucleic acid sequence encoding an anti-infective peptide described herein (e.g., in Sections 5.1 and 6). Due to the degeneracy of the genetic code, any nucleic acid that encodes an anti-infective peptide described herein is encompassed herein. In a particular embodiment, provided herein is a nucleic acid sequence encoding an anti-infective peptide listed in Table 2A or Table 2B. In another embodiment, provided herein is a nucleic acid sequence encoding an anti-infective peptide listed in Table 4. In a specific embodiment, provided herein is a nucleic acid sequence encoding an anti-infective peptide described in Section 6.

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded.

Also provided herein are nucleic acid sequences capable of hybridizing to a nucleic acid sequence encoding an anti-infective peptide. In certain embodiments, provided herein are nucleic acids capable of hybridizing to a fragment of a nucleic acid encoding an anti-infective peptide. In other embodiments, provided herein are nucleic acids capable of hybridizing to the full length of a nucleic acid encoding an anti-infective peptide. General parameters for hybridization conditions for nucleic acids are described in Sambrook et al., Molecular Cloning—A Laboratory Manual (2nd Ed.), Vols. 1-3, Cold Spring Harbor Laboratory, Cold Spring Harbor, New York (1989), and in Ausubel et al., Current Protocols in Molecular Biology, vol. 2, Current Protocols Publishing, New York (1994). Hybridization may be performed under high stringency conditions, medium stringency conditions, or low stringency conditions. Those of skill in the art will understand that low, medium and high stringency conditions are contingent upon multiple factors all of which interact and are also dependent upon the nucleic acids in question. For example, high stringency conditions may include temperatures within 5° C. melting temperature of the nucleic acid(s), a low salt concentration (e.g., less than 250 mM), and a high co-solvent concentration (e.g., 1-20% of the co-solvent, e.g., DMSO). Low stringency conditions, on the other hand, may include temperatures greater than 10° C. below the melting temperature of the nucleic acid(s), a high salt concentration (e.g., greater than 1000 mM) and the absence of co-solvents.

In some embodiments, a nucleic acid sequence encoding an anti-infective peptide is isolated. In certain embodiments, an "isolated" nucleic acid sequence refers to a nucleic acid molecule which is separated from other nucleic acid molecules which are present in the natural source of the nucleic acid. In other words, the isolated nucleic acid sequence can comprise heterologous nucleic acids that are not associated with it in nature. In other embodiments, an "isolated" nucleic acid sequence, such as a cDNA molecule, can be substantially free of other cellular material, or culture medium when produced by recombinant techniques, or substantially free of chemical precursors or other chemicals when chemically synthesized. The term "substantially free of cellular material" includes preparations of nucleic acid sequence in which the nucleic acid sequence is separated from cellular components of the cells from which it is isolated or recombinantly produced. Thus, the nucleic acid sequence that is substantially free of cellular material includes preparations of the nucleic acid sequence having less than about 30%, 20%, 10%, or 5% (by dry weight) of other nucleic acids. The term "substantially free of culture medium" includes preparations of nucleic acid sequence in which the culture medium represents less than about 50%, 20%, 10%, or 5% of the volume of the preparation. The term "substantially free of chemical precursors or other chemicals" includes preparations in which the nucleic acid sequence is separated from chemical precursors or other chemicals which are involved in the synthesis of the nucleic acid sequence. In specific embodiments, such preparations of the nucleic acid sequence have less than about 50%, 30%, 20%, 10%, 5% (by dry weight) of chemical precursors or compounds other than the nucleic acid sequence of interest.

Provided herein are vectors, including expression vectors, containing a nucleic acid sequence encoding an anti-infective peptide described herein. In a specific embodiment, the vector is an expression vector that is capable of directing the expression of a nucleic acid sequence encoding an anti-infective peptide described herein. Non-limiting examples of expression vectors include, but are not limited to, plasmids and viral vectors, such as replication defective retroviruses, adenoviruses, adeno-associated viruses and baculoviruses. Expression vectors also may include, without limitation, transgenic animals and non-mammalian cells/organisms, e.g., mammalian cells/organisms that have been engineered to perform mammalian N-linked glycosylation.

An expression vector comprises a nucleic acid sequence encoding an anti-infective peptide described herein and in a form suitable for expression of the nucleic acid in a host cell. In a specific embodiment, an expression vector includes one or more regulatory sequences, selected on the basis of the host cells to be used for expression, which is operably linked to the nucleic acid to be expressed. Within an expression vector, "operably linked" is intended to mean that a nucleic acid sequence of interest is linked to the regulatory sequence(s) in a manner which allows for expression of the nucleic acid sequence (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid sequence in many types of host cells, those which direct expression of the nucleic acid sequence only in certain host cells (e.g., tissue-specific regulatory sequences), and those which direct the expression of the nucleic acid sequence upon stimulation with a particular agent (e.g., inducible regulatory sequences). It will be appreciated by those skilled in the art that the design of the expression vector can depend on such factors as the choice of the host cell to be transformed, the level of expression of protein desired, etc. The term "host cell" is intended to include a particular subject cell transformed or transfected with a nucleic acid sequence and the progeny or potential progeny of such a cell. Progeny of such a cell may not be identical to the parent cell transformed or transfected with the nucleic acid sequence due to mutations or environmental influences that may occur in succeeding generations or integration of the nucleic acid sequence into the host cell genome. In specific embodiments, the host cell is a cell line.

Expression vectors can be designed for expression of an anti-infective peptide described herein using prokaryotic (e g., E. coli) or eukaryotic cells (e.g., insect cells (using baculovirus expression vectors, see, e.g., Treanor et al., 2007, JAMA, 297(14):1577-1582 incorporated by reference herein in its entirety), yeast cells, plant cells, algae, avian, or mammalian cells). Examples of yeast host cells include, but are not limited to *S. pombe* and *S. cerevisiae*. An example of avian cells includes, but is not limited to EB66 cells. Examples of mammalian host cells include, but are not limited to, Crucell Per.C6 cells, Vero cells, CHO cells, VERO cells, BHK cells, HeLa cells, COS cells, MDCK cells, 293 cells, 3T3 cells or WI38 cells. In certain embodiments, the hosts cells are myeloma cells, e.g., NS0 cells, 45.6 TG1.7 cells, AF-2 clone 9B5 cells, AF-2 clone 9B5 cells, J558L cells, MOPC 315 cells, MPC-11 cells, NCI-H929 cells, NP cells, NS0/1 cells, P3 NS1 Ag4 cells, P3/NS1/1-Ag4-1 cells, P3U1 cells, P3X63Ag8 cells, P3X63Ag8.653 cells, P3X63Ag8U.1 cells, RPMI 8226 cells, Sp20-Ag14 cells, U266B1 cells, X63AG8.653 cells, Y3.Ag.1.2.3 cells, and YO cells. Non-limiting examples of insect cells include Sf9, Sf21, *Trichoplusia ni, Spodoptera frugiperda* and *Bombyx mori*. In a particular embodiment, a mammalian cell culture system (e.g. Chinese hamster ovary or baby hamster kidney cells) is used for expression of an anti-infective peptide. In another embodiment, a plant cell culture system is used for expression of an anti-infective peptide. See, e.g., U.S. Pat. Nos. 7,504,560; 6,770,799; 6,551,820; 6,136,320; 6,034,298; 5,914,935; 5,612,487; and 5,484,719, and U.S. patent application publication Nos. 2009/0208477, 2009/0082548, 2009/0053762, 2008/0038232, 2007/0275014 and 2006/0204487 for plant cells and methods for the production of proteins utilizing plant cell culture systems. The host cells comprising a nucleic acid sequence that encodes an anti-infective peptides described herein can be isolated, i.e., the cells are outside of the body of a subject. In certain embodiments, the host cells are engineered to express a nucleic acid sequence that encodes an anti-infective peptide described herein. In specific embodiments, the host cells are cells from a cell line.

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning—A Laboratory Manual, 2nd Edition, Cold Spring Harbor Press, New York, and other laboratory manuals. In certain embodiments, a host cell is transiently transfected with an expression vector containing a nucleic acid sequence encoding an anti-infective peptide. In other embodiments, a host cell is stably transfected with an expression vector containing a nucleic acid sequence encoding an anti-infective peptide For stable transfection of mammalian cells, it is known that, depending upon the expression vector and transfection technique used, only a small fraction of cells may integrate the foreign DNA into their genome. In order to identify and select these integrants, a nucleic acid sequence that encodes a selectable marker (e.g., for resistance to antibiotics) is generally introduced into the host cells along with the nucleic acid sequence of interest. Examples of selectable markers include those which confer resistance to drugs, such as G418, hygromycin and methotrexate. Cells stably transfected with the introduced nucleic acid sequence can be identified by drug selection (e.g., cells that have incorporated the selectable marker gene will survive, while the other cells die).

As an alternative to recombinant expression of an anti-infective peptide using a host cell, an expression vector containing a nucleic acid sequence encoding an anti-infective peptide can be transcribed and translated in vitro using, e.g., T7 promoter regulatory sequences and T7 polymerase. In a specific embodiment, a coupled transcription/translation system, such as Promega TNT®, or a cell lysate or cell extract comprising the components necessary for transcription and translation may be used to produce an anti-infective peptide.

Once an anti-infective peptide has been produced, it may be isolated or purified by any method known in the art for isolation or purification of a protein, for example, by chromatography (e.g., ion exchange, affinity, particularly by affinity for the specific antigen, by Protein A, and sizing column chromatography), centrifugation, differential solubility, or by any other standard technique for the isolation or purification of proteins.

Accordingly, provided herein are methods for producing an anti-infective peptide. In one embodiment, the method comprises culturing a host cell containing a nucleic acid sequence encoding an anti-infective peptide in a suitable medium such that the peptide is produced. In some embodiments, the method further comprises isolating the peptide from the medium or the host cell.

5.4 Compositions

Provided herein are compositions (e.g., pharmaceutical compositions) comprising an effective amount of an anti-infective peptide described herein (see, e.g., Section 5.1, Section 5.2, and Section 6). Also provided herein are compositions comprising an effective amount of an anti-infective peptide described herein (see Section 5.1, Section 5.2, and Section 6) and a carrier or diluent. In a specific embodiment, the carrier is an aqueous solution. In a specific embodiment, the aqueous solution is sterile water. In another specific embodiment, the aqueous solution is distilled water. In a specific embodiment, the carrier is a pharmaceutically acceptable carrier. Also provided herein are compositions comprising an effective amount of an anti-infective peptide described herein (see Section 5.1, Section 5.2, and Section 6) and a vehicle. In another embodiment, provided herein are compositions, comprising an effective amount of an anti-infective peptide and a pharmaceutically acceptable carrier or vehicle, wherein a pharmaceutically acceptable carrier or vehicle can comprise an excipient, diluent, or a mixture thereof. In one embodiment, the composition is a pharmaceutical composition. In some embodiments, the composition comprises two, three or more anti-infective peptides described herein.

In a specific embodiment, a composition described herein is for use in a method described herein (see Section 5.5). For example, an anti-infective peptide can be administered to a subject or utilized in an in vitro cell culture assay alone or as a component of a composition. The subject anti-infective peptides may be formulated for administration in any convenient way for use in human or veterinary medicine or for use in an in vivo, ex vivo or in vitro method described herein.

The formulation of a pharmaceutical composition will vary depending upon the route of administration to a subject. An anti-infective peptide described herein can be administered orally, intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition or the type of bacteria or virus infection.

For example, the anti-infective peptides can be administered to a patient orally or parenterally in the conventional form of preparations, such as capsules, tablets, microcapsules, granules, troches, powder, pills, injections, suppositories, suspensions and syrups. Suitable formulations can be prepared by methods commonly employed using conventional, organic or inorganic additives, such as an excipient (e.g., sucrose, glucose, lactose, cellulose, sorbitol, talc, mannitol, calcium phosphate, starch, or calcium carbonate), a binder (e.g., cellulose, hydroxymethylcellulose, methylcellulose, polyvinylpyrrolidone, polypropylpyrrolidone, gum arabic, gelatin, polyethyleneglycol, starch, or sucrose), a disintegrator (e.g., starch, hydroxypropylstarch, carboxymethylcellulose, low substituted hydroxypropylcellulose, calcium phosphate, sodium bicarbonate, or calcium citrate), a lubricant (e.g., magnesium stearate, talc, light anhydrous silicic acid, or sodium lauryl sulfate), a flavoring agent (e.g., citric acid, glycine, menthol, or orange powder), a preservative (e.g., sodium benzoate, methylparaben, sodium bisulfite, or propylparaben), a stabilizer (e.g., citric acid, acetic acid, or sodium citrate), a suspending agent (e.g., methylcellulose, aluminum stearate, or polyvinyl pyrrolicione), a dispersing agent (e.g., hydroxypropylmethylcellulose), a diluent (e.g., water), and base wax (e.g., cocoa butter, polyethylene glycol, or white petrolatum). In one embodiment, provided herein are capsules containing an anti-infective peptide without an additional carrier, excipient or vehicle In another example, for topical applications, the composition may comprise an anti-infective peptide in an aqueous solution that includes one, two, or more, or a combination of: 5 wt % or less (between 0.5 and 5%) hydroxyethylcellulose, 5 wt % or less (between 0.5 and 5%) glycerin, and PEG 3 wt % or less (between 0.3 and 3%). In another example, the composition of topical application is formulated as a conventional gel formulation for topical microbicides. In another example, the composition is formulated as a gel, capsule, tablet, film or intravaginal ring.

In certain embodiments, an anti-infective peptide is formulated in a suspension, such as a liposome, micelle, nanoparticle, or polyelectrolyte suspension. In some embodiments, an anti-infective peptide is non-covalently or covalently linked to the surface of a liposome, micelle, nanoparticle, or polyelectrolyte. The linkage may be direct or via a flexible tether (e.g., a PEG spacer chain).

In a specific embodiment, the compositions provided herein have a pH of 4 to 7.5, 4.5 to 7.5, 5 to 7.5, 5.5 to 7.5, 6 to 7.5, or 6.5 to 7.5. In another specific embodiment, the compositions provided herein have a pH of about 4.5, about 5 about 5.5, about 6, about 6.5, about 7 or about 7.5.

In a specific embodiment, a composition described herein comprises the anti-infective peptide in an amount effective to inhibit microbial growth. In a specific embodiment, a composition described herein comprises the anti-infective peptide in an amount effective to inhibit microbial growth and a carrier. In a specific embodiment, a composition described herein comprises the anti-infective peptide in an amount effective to inhibit microbial growth by at least 2-fold, 3-fold, 4-fold, 5-fold, 6-fold, 7-fold, 8-fold, 9-fold, 10-fold, 20-fold, 50-fold, 75-fold, 100-fold, or 1,000-fold as compared to microbial growth in the absence of the composition. In a specific embodiment a composition described herein comprises the anti-infective peptide in an amount effective to inhibit microbial growth by between 2-fold and 5-fold, between 2-fold and 10-fold, between 2-fold and 20-fold, between 5-fold and 100-fold, between 10-fold and 50-fold, between 10-fold and 100-fold, or between 100-fold and 1,000-fold as compared to microbial growth in the absence of the composition. In a specific embodiment, the microbial growth that is inhibited is growth of a microbe described in Section 5.7.

In a specific embodiment, a composition described herein comprises the anti-infective peptide in an amount effective to inhibit viral growth. In a specific embodiment, a composition described herein comprises the anti-infective peptide in an amount effective to inhibit viral growth and a carrier. In a specific embodiment, a composition described herein comprises the anti-infective peptide in an amount effective to inhibit viral growth by at least 2-fold, 3-fold, 4-fold, 5-fold, 6-fold, 7-fold, 8-fold, 9-fold, 10-fold, 20-fold, 50-fold, 75-fold, 100-fold, or 1,000-fold as compared to viral growth in the absence of the composition. In a specific embodiment, a composition described herein comprises the anti-infective peptide in an amount effective to inhibit viral growth by between 2-fold and 5-fold, between 2-fold and 10-fold, between 2-fold and 20-fold, between 5-fold and 100-fold, between 10-fold and 50-fold, between 10-fold and 100-fold, or between 100-fold and 1,000-fold as compared to viral growth in the absence of the composition. In a specific embodiment, the viral growth that is inhibited is growth of a virus described in Section 5.7.

In a specific embodiment, a composition described herein comprises the anti-infective peptide in an amount effective to inhibit viral replication. In a specific embodiment, a composition described herein comprises the anti-infective peptide in an amount effective to inhibit viral replication and a carrier. In a specific embodiment, a composition described herein comprises the anti-infective peptide in an amount effective to inhibit viral replication by at least 2-fold, 3-fold, 4-fold, 5-fold, 6-fold, 7-fold, 8-fold, 9-fold, 10-fold, 20-fold, 50-fold, 75-fold, 100-fold, or 1,000-fold as compared to viral replication in the absence of the composition. In a specific embodiment, a composition described herein comprises the anti-infective peptide in an amount effective to viral replication growth by between 2-fold and 5-fold, between 2-fold and 10-fold, between 2-fold and 20-fold, between 5-fold and 100-fold, between 10-fold and 50-fold, between 10-fold and 100-fold, or between 100-fold and 1,000-fold as compared to viral replication in the absence of the composition. In a specific embodiment, a composition described herein comprises the anti-infective peptide in an amount effective to inhibit viral replication by at least 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs as compared to viral replication in the absence of the composition. In a specific embodiment, a composition described herein comprises the anti-infective peptide in an amount effective to viral replication growth by between 0.5 log and 2.5 logs, 1 log and 3 logs, 2 logs and 4 logs, 3 logs and 5 logs, 4 logs and 6 logs, 5 logs and 7 logs, 6 logs and 8 logs, 7 logs and 9 logs, or 8 logs and 10 logs as compared to viral replication in the absence of the composition. In a specific embodiment, the viral replication that is inhibited is replication of a virus described in Section 5.7.

In a specific embodiment, a composition described herein comprises the anti-infective peptide in an amount effective to kill a virus. In a specific embodiment, a composition described herein comprises the anti-infective peptide in an amount effective to kill a virus and a carrier. In a specific embodiment, a composition described herein comprises the anti-infective peptide in an amount effective to kill at least 10%, at least 20%, at least 30%, at least 40%, at least 50%, at least 60%, at least 70%, at least 80%, at least 90%, at least 95%, at least 98%, at least 99%, or 100% of virus in a population. In a specific embodiment, a composition described herein comprises the anti-infective peptide in an amount effective to kill between 10% and 20%, 10% and 30%, 10% and 40%, 10% and 50%, 10% and 60%, 10% and 70%, 10% and 80%, 10% and 90%, or 10% and 100% of a virus in a population. In a specific embodiment, a composition described herein comprises the anti-infective peptide in an amount effective to kill between 10% and 40%, 20% and 60%, 30% and 50%, 40% and 60%, 50% and 70%, 60% and 80%, 70% and 90%, 90% and 95%, 90% and 98%, or 90% and 100% of virus in a population. In a specific embodiment, the virus is a virus described in Section 5.7.

In a specific embodiment, a composition described herein comprises the anti-infective peptide in an amount effective to inhibit bacterial growth. In a specific embodiment, the composition comprises the anti-infective peptide in an amount effective to inhibit bacterial growth and a carrier. In a specific embodiment, a composition described herein comprises the anti-infective peptide in an amount effective to inhibit bacterial growth by at least 2-fold, 3-fold, 4-fold, 5-fold, 6-fold, 7-fold, 8-fold, 9-fold, 10-fold, 20-fold, 50-fold, 75-fold, 100-fold, or 1,000-fold as compared to bacterial growth in the absence of the composition. In a specific embodiment, a composition described herein comprises the anti-infective peptide in an amount effective to inhibit bacterial growth by between 2-fold and 5-fold, between 2-fold and 10-fold, between 2-fold and 20-fold, between 5-fold and 100-fold, between 10-fold and 50-fold, between 10-fold and 100-fold, or between 100-fold and 1,000-fold as compared to bacterial growth in the absence of the composition. In a specific embodiment, the bacterial growth that is inhibited is growth of a bacterium described in Section 5.7.

In a specific embodiment, a composition described herein comprises the anti-infective peptide in an amount effective to inhibit bacterial replication. In a specific embodiment, a composition described herein comprises the anti-infective peptide in an amount effective to inhibit bacterial replication and a carrier. In a specific embodiment, a composition described herein comprises the anti-infective peptide in an amount effective to inhibit bacterial replication by at least 2-fold, 3-fold, 4-fold, 5-fold, 6-fold, 7-fold, 8-fold, 9-fold, 10-fold, 20-fold, 50-fold, 75-fold, 100-fold, or 1,000-fold as compared to bacterial replication in the absence of the composition. In a specific embodiment, a composition described herein comprises the anti-infective peptide in an amount effective to inhibit bacterial replication by between 2-fold and 5-fold, between 2-fold and 10-fold, between 2-fold and 20-fold, between 5-fold and 100-fold, between 10-fold and 50-fold, between 10-fold and 100-fold, or between 100-fold and 1,000-fold as compared to bacterial replication in the absence of the composition. In a specific embodiment, the bacterial replication that is inhibited is replication of a bacterium described in Section 5.7.

In a specific embodiment, a composition described herein comprises the anti-infective peptide in an amount effective to kill bacteria. In a specific embodiment, the composition comprises the anti-infective peptide in an amount effective to kill a bacteria and a carrier. In a specific embodiment, a composition described herein comprises the anti-infective peptide in an amount effective to kill at least 10%, at least 20%, at least 30%, at least 40%, at least 50%, at least 60%, at least 70%, at least 80%, at least 90%, at least 95%, at least 98%, at least 99%, or 100% of a bacterium in a population. In a specific embodiment, a composition described herein comprises the anti-infective peptide in an amount effective to kill between 10% and 20%, 10% and 30%, 10% and 40%, 10% and 50%, 10% and 60%, 10% and 70%, 10% and 80%, 10% and 90%, or 10% and 100% of a bacterium in a population. In a specific embodiment, a composition described herein comprises the anti-infective peptide in an amount effective to kill between 10% and 40%, 20% and 60%, 30% and 50%, 40% and 60%, 50% and 70%, 60% and 80%, 70% and 90%, 90% and 95%, 90% and 98%, or 90% and 100% of a bacterium in a population. In a specific embodiment, the bacterium is a bacterium described in Section 5.7.

In a specific embodiment, a pharmaceutical composition is formulated for topical administration. In a specific embodiment, a pharmaceutical composition formulated for topical administration is a gel formulation. In a specific embodiment, the effective amount of the anti-infective peptide in the gel formulation is between 0.1% and 5%. In a specific embodiment, a pharmaceutical composition formulated for use as an intravaginal ring. In a specific embodiment, the pharmaceutical composition formulated for topical administration is used in a prophylactic method of treatment described in Section 5.5. In a specific embodiment, the pharmaceutical composition formulated for topical administration is used in a therapeutic method of treatment described in Section 5.5.

In a specific embodiment, a pharmaceutical composition is formulated for systemic administration. In a specific embodiment, a pharmaceutical composition formulated for systemic administration is a lyophilized powder or cake. In a specific embodiment, the lyophilized powder or cake comprises between 10 mg and 300 mg of the anti-infective peptide. In a specific embodiment, the lyophilized powder or cake comprises between 10 mg and 100 mg, 50 and 150 mg, 100 and 200 mg, 150 mg and 250 mg, or between 200 mg and 300 mg of the anti-infective peptide. In a specific embodiment, the lyophilized powder or cake comprises 200 mg to 300 mg of the anti-infective peptide. In a specific embodiment, the lyophilized powder or cake is resuspended in 1 mL of aqueous solution. In a specific embodiment, the pharmaceutical composition is administered once daily to a subject. In a specific embodiment, the composition is administered twice daily to a subject. In a specific embodiment, the anti-infective peptide formulated for systemic administration is used in a prophylactic method of treatment described in Section 5.5. In a specific embodiment, the anti-infective peptide formulated for systemic administration is used in a therapeutic method of treatment described in Section 5.5.

In a specific embodiment, the composition is a disinfecting solution comprising an anti-infective peptide described herein (see, e.g., Section 5.1, Section 5.2, and Section 6). In a specific embodiment, the disinfecting solution is formulated for disinfecting an inanimate object. When the disinfecting solution is formulated for disinfecting an inanimate object, the disinfecting solution may be a wipe or a spray. In another embodiment, the composition is formulated for use in disinfecting a biological material or non-biological material. Biological material(s) includes, but is not limited to, biological fluids (e.g., blood), blood components, tissues, organs and cell cultures. Biological surfaces include skin (e.g., hands, site being prepped for surgery, etc.). When disinfecting a biological surface, an anti-infective peptide(s) described herein can be administered in the form of formulated as topical creams, ointments, lotions, gels, powders, liquids, solids, detergents or soaps.

In a specific embodiment, the disinfecting solution is formulated for disinfecting a subject, e.g., a subject described in Section 5.6. When the disinfecting solution is formulated for disinfecting a subject, the disinfecting solution may be a hand or body wash, a wound dressing, a gel, a lotion, a cream, an ointment, a surgical scrub, or a spray that can be sprayed onto a skin, wound, or surface. In a specific embodiment, the disinfectant formulation is aqueous based or glycerol based.

The disinfecting anti-infective peptide-containing compositions may include one or more additional compounds, as desired, with the proviso these additional compounds do not significantly adversely affect anti-viral and/or anti-bacterial activity of the peptide. For example, such compounds may be anti-microbial (e.g., antibacterial, antifungal) agents so as to enhance disinfection with respect to microorganisms.

In certain embodiments, an anti-infective peptide described herein is coated onto the surface of an inanimate surface (e.g., a medical device) or a biological surface. An anti-infective peptide described herein can be directly or indirectly coated onto the surface via covalent or noncovalent methods.

In a specific embodiment, the disinfecting solution is for use in a method described herein (see Section 5.5).

5.5 Methods of Use

In one aspect, provided herein are methods for inhibiting growth, replication, or infectivity of a microorganism, comprising contacting the microorganism with an anti-infective peptide described herein (see, e.g., Section 5.1, Section 5.2 and Section 6) or a composition described herein (see, e.g., Section 5.4). In one embodiment, provided herein is a method for inhibiting growth, replication, or infectivity of a microorganism, comprising contacting the microorganism with an effective amount of an anti-infective peptide described herein (see, e.g., Section 5.1, Section 5.2 and Section 6) or a composition described herein (see, e.g., Section 5.4). In a specific embodiment, the microorganism is in vitro or ex vivo. In other specific embodiments, the microorganism is in vivo. In another specific embodiment, the microorganism is a microorganism described in Section 5.7 or 6.

In another aspect, provided herein are methods for inhibiting bacterial growth, comprising contacting the bacteria with an anti-infective peptide described herein (see, e.g., Section 5.1, Section 5.2 and Section 6) or a composition described herein (see, e.g., Section 5.4). In one embodiments, provided herein is a method for inhibiting bacterial growth, comprising contacting the cell with an effective amount of an anti-infective peptide described herein (see, e.g., Section 5.1, Section 5.2 and Section 6) or a composition described herein (see, e.g., Section 5.4). In a specific embodiment, the bacteria is in vitro or ex vivo. In other specific embodiments, the bacteria is in vivo. In another specific embodiment, the bacteria is a bacteria described in Section 5.7 or Section 6. In certain embodiments, the inhibition in bacterial growth results in a 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold or more reduction in the number of bacteria relative to the number of bacteria resulting when the bacteria are not contacted with the peptide or composition. In some embodiments, the inhibition in bacterial growth results in a 1 log, 2 logs, 3 logs, 4 logs, 5 logs, 6 logs, 7 logs, 8 logs, 9 logs, 10 logs or more reduction in the number of bacteria relative to the number of bacteria resulting when the bacteria are not contacted with the peptide or composition.

In another aspect, provided herein are methods for inhibiting bacterial growth in a cell, comprising contacting the cell with an anti-infective peptide described herein (see, e.g., Section 5.1, Section 5.2 and Section 6) or a composition described herein (see, e.g., Section 5.4). The cell may be contacted before infection with a bacteria or after infection with a bacteria. In one embodiments, provided herein is a method for inhibiting bacterial growth, in a cell, comprising contacting the cell infected with a bacteria with an effective amount of an anti-infective peptide described herein (see, e.g., Section 5.1, Section 5.2 and Section 6) or a composition described herein (see, e.g., Section 5.4). In a specific embodiment, the cell is in vitro or ex vivo. In other specific embodiments, the cell is in vivo. In another specific embodiment, the bacteria is a bacteria described in Section 5.7 or 6. In certain embodiments, the inhibition in bacterial growth results in a 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold or more reduction in the number of bacteria relative to the number of bacteria resulting when the cell is not contacted with the peptide or composition. In some embodiments, the inhibition in bacterial growth results in a 1 log, 2 logs, 3 logs, 4 logs, 5 logs, 6 logs, 7 logs, 8 logs, 9 logs, 10 logs or more reduction in the number of bacteria relative to the number of bacteria resulting when the cell is not contacted with the peptide or composition.

In another aspect, provided herein are methods for inhibiting viral replication in a cell, comprising contacting the cell an anti-infective peptide described herein (see, e.g., Section 5.1, Section 5.2 and Section 6) or a composition described herein (see, e.g., Section 5.4). The cell may be contacted before infection with a virus or after infection with a virus. In one embodiment, provided herein is a method for inhibiting viral replication in a cell, comprising contacting the cell infected with a virus with an effective amount of an anti-infective peptide described herein (see, e.g., Section 5.1, Section 5.2 and Section 6) or a composition described herein (see, e.g., Section 5.4). In a specific embodiment, the cell is in vitro or ex vivo. In other specific embodiments, the cell is in vivo. In another specific embodiment, the virus is a virus described in Section 5.7 or 6. In certain embodiments, the inhibition in viral replication results in a 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold or more reduction in viral particles relative to the number of viral particles when the cell is not contacted with the peptide or composition. In some embodiments, the viral replication is reduced 1 log, 2 logs, 3 logs, 4 logs, 5 logs, 6 logs, 7 logs, 8 logs, 9 logs, 10 logs or more relative to the number of viral particles when the cell is not contacted with the peptide or composition thereof. In another aspect, provided herein are prophylactic and therapeutic methods using an anti-infective peptide described herein or a composition thereof. In a specific embodiment, the anti-infective peptide described herein or a composition comprising the same is used prophylactically. In another specific embodiment, the anti-infective peptide described herein or a composition comprising the same is used therapeutically.

In another embodiment, provided herein are methods for treating a microorganism infection or disease caused by or associated therewith in a subject, comprising administering to the subject an anti-infective peptide described herein (see, e.g., Section 5.1, Section 5.2 and Section 6) or a composition described herein (see, e.g., Section 5.4). In one embodiment, provided herein is a method for treating a microorganism infection in a subject, comprising administering to the subject an effective amount of anti-infective peptide described herein (see, e.g., Section 5.1, Section 5.2 and Section 6) or a composition described herein (see, e.g., Section 5.4). In another embodiment, provided herein is a method for treating a disease caused by or associated with a microorganism infection in a subject, comprising administering to the subject an effective amount of anti-infective peptide described herein (see, e.g., Section 5.1, Section 5.2 and Section 6) or a composition described herein (see, e.g., Section 5.4). In a specific embodiment, the microorganism is a microorganism described in Section 5.7 or 6. In another specific embodiment, the subject is a subject described in Section 5.6.

In a specific embodiment, the treatment of a microorganism infection or disease caused by or associated therewith with an anti-infective peptide described herein or composition thereof, or a combination of an anti-infective peptide described herein and another therapy results in a beneficial or therapeutic effect. In specific embodiments, the treatment of a microorganism infection or disease caused by or associated therewith with an anti-infective peptide described herein or composition thereof, or a combination of an anti-infective peptide described herein and another therapy results in one, two, three, four, five, or more, or all of the following effects: (i) the reduction or amelioration of the severity of a microorganism infection or a disease or a symptom caused by or associated therewith; (ii) the reduction in the duration of a microorganism infection or a disease or a symptom caused by or associated therewith; (iii) the regression of a microorganism infection or a disease or a symptom caused by or associated therewith; (iv) the reduction of the particles/titer of a microorganism; (v) the reduction in organ failure associated with a microorganism infection or a disease caused by or associated therewith; (vi) the reduction in hospitalization of a subject; (vii) the reduction in hospitalization length; (viii) the increase in the survival of a subject; (ix) the elimination of a microorganism infection or a disease or a symptom caused by or associated therewith; (x) the inhibition of the progression of a microorganism infection or a disease or a symptom caused by or associated therewith; (xi) the prevention of the spread of a microorganism from a cell, tissue, organ or subject to another cell, tissue, organ or subject; and/or (xii) the enhancement or improvement the therapeutic effect of another therapy.

In another aspect, provided herein are methods for preventing a disease in a subject caused by or associated with a microorganism infection, comprising administering to the subject an anti-infective peptide described herein (see, e.g., Section 5.1, Section 5.2 and Section 6) or a composition described herein (see, e.g., Section 5.4). In one embodiment, provided herein is a method for preventing a disease in a subject caused by or associated with a microorganism infection, comprising administering to the subject an effective amount of an anti-infective peptide described herein (see, e.g., Section 5.1, Section 5.2 and Section 6) or a composition described herein (see, e.g., Section 5.4). In a specific embodiment, the microorganism is a microorganism described in Section 5.7 or 6. In a specific embodiment, the subject is a subject described in Section 5.6.

In a specific embodiment, the administration of an anti-infective peptide described herein or composition thereof, or a combination of an anti-infective peptide described herein and another therapy to a subject to prevent a disease caused by or associated with a microorganism infection results in one or more of the prophylactic/beneficial effects. In a specific embodiment, the administration of an anti-infective peptide described herein or composition thereof, or a combination of an anti-infective peptide described herein and another therapy to a subject to prevent a disease caused by or associated with a microorganism infection results in one, two or more, or all of the following effects: (i) the inhibition of the development or onset of a disease caused by or associated with a microorganism infection or a symptom thereof; (ii) the inhibition of the recurrence of a disease caused by or associated with a microorganism infection or a symptom associated therewith; and (iii) the reduction or inhibition in microorganism infection and/or replication.

In another aspect, provided herein are methods for inhibiting bacterial growth in a subject, comprising administering to the subject an anti-infective peptide described herein (see, e.g., Section 5.1, Section 5.2 and Section 6) or a composition described herein (see, e.g., Section 5.4). In one embodiment, provided herein is a method for inhibiting bacterial growth in a subject, comprising administering to the subject an effective amount of an anti-infective peptide described herein (see, e.g., Section 5.1, Section 5.2 and Section 6) or a composition described herein (see, e.g., Section 5.4). In a specific embodiment, the bacteria is a bacteria described in Section 5.7 or 6. In another specific embodiment, the subject is a subject described in Section 5.6.

In another aspect, provided herein are methods for treating a bacterial infection in a subject, comprising administering to the subject an anti-infective peptide described herein (see, e.g., Section 5.1, Section 5.2 and Section 6) or a composition described herein (see, e.g., Section 5.4). In one embodiment, provided herein is a method for treating a bacterial infection in a subject, comprising administering to the subject an effective amount of anti-infective peptide described herein (see, e.g., Section 5.1, Section 5.2 and Section 6) or a composition described herein (see, e.g., Section 5.4). In a specific embodiment, the bacteria is a bacteria described in Section 5.7 or 6. In another specific embodiment, the subject is a subject described in Section 5.6.

In another aspect, provided herein are methods for treating a disease in a subject which disease is caused by or associated with a bacterial infection, comprising administering to the subject an anti-infective peptide described herein (see, e.g., Section 5.1, Section 5.2 and Section 6) or a composition described herein (see, e.g., Section 5.4). In one embodiment, provided herein is a method for treating a disease in a subject which disease is caused by or associated with a bacterial infection, comprising administering to the subject an effective amount of an anti-infective peptide described herein (see, e.g., Section 5.1, Section 5.2 and Section 6) or a composition described herein (see, e.g., Section 5.4). In a specific embodiment, the bacteria is a bacteria described in Section 5.7 or 6. In another specific embodiment, the subject is a subject described in Section 5.6.

In a specific embodiment, the treatment of a bacterial infection or disease caused by or associated therewith with an anti-infective peptide described herein or composition thereof, or a combination of an anti-infective peptide described herein and another therapy results in a beneficial or therapeutic effect. In specific embodiments, the treatment of a bacterial infection or disease caused by or associated therewith with an anti-infective peptide described herein or composition thereof, or a combination of an anti-infective peptide described herein and another therapy results in one, two, three, four, five, or more, or all of the following effects: (i) the reduction or amelioration of the severity of a bacterial infection or a disease or a symptom caused by or associated therewith: (ii) the reduction in the duration of a bacterial infection or a disease or a symptom caused by or associated therewith; (iii) the regression of a bacterial infection or a disease or a symptom caused by or associated therewith; (iv) the reduction of the number/titer of bacteria; (v) the reduction in organ failure associated with a bacterial infection or a disease caused by or associated therewith; (vi) the reduction in hospitalization of a subject; (vii) the reduction in hospitalization length; (viii) the increase in the survival of a subject; (ix) the elimination of a bacterial infection or a disease or a symptom caused by or associated therewith; (x) the inhibition of the progression of a bacterial infection or a disease or a symptom caused by or associated therewith; (xi) the prevention of the spread of bacteria from a cell, tissue, organ or subject to another cell, tissue, organ or subject; and/or (xii) the enhancement or improvement the therapeutic effect of another therapy.

In another aspect, provided herein are methods for preventing a disease in a subject which disease is caused by or associated with a bacterial infection, comprising administering to the subject an anti-infective peptide described herein (see, e.g., Section 5.1, Section 5.2 and Section 6) or a composition described herein (see, e.g., Section 5.4). In one embodiment, provided herein is a method for preventing a disease in a subject which disease is caused by or associated with a bacterial infection, comprising administering to the subject an effective amount of an anti-infective peptide described herein (see, e.g., Section 5.1, Section 5.2 and Section 6) or a composition described herein (see, e.g., Section 5.4). In a specific embodiment, the bacteria is a bacteria described in Section 5.7 or 6. In another specific embodiment, the subject is a subject described in Section 5.6.

In a specific embodiment, the administration of an anti-infective peptide described herein or composition thereof, or a combination of an anti-infective peptide described herein and another therapy to a subject to prevent a disease caused by or associated with a bacterial infection results in one or more of the prophylactic/beneficial effects. In a specific embodiment, the administration of an anti-infective peptide described herein or composition thereof, or a combination of an anti-infective peptide described herein and another therapy to a subject to prevent a disease caused by or associated with a bacterial infection results in one, two or more, or all of the following effects: (i) the inhibition of the development or onset of a disease caused by or associated with a bacterial infection or a symptom thereof; (ii) the inhibition of the recurrence of a disease caused by or associated with a bacterial infection or a symptom associated therewith; and (iii) the reduction or inhibition in a bacterial infection and/or replication.

In another aspect, provided herein are methods for inhibiting viral replication in a subject, comprising administering to the subject an anti-infective peptide described herein (see, e.g., Section 5.1, Section 5.2 and Section 6) or a composition described herein (see, e.g., Section 5.4). In one embodiment, provided herein is a method for inhibiting viral replication in a subject, comprising administering to the subject an effective amount of an anti-infective peptide described herein (see, e.g., Section 5.1, Section 5.2 and Section 6) or a composition described herein (see, e.g., Section 5.4). In a specific embodiment, the virus is a virus described in Section 5.7 or 6. In another specific embodiment, the subject is a subject described in Section 5.6.

In another aspect, provided herein are methods for treating a viral infection in a subject, comprising administering to the subject an anti-infective peptide described herein (see, e.g., Section 5.1, Section 5.2 and Section 6) or a composition described herein (see, e.g., Section 5.4). In one embodiment, provided herein is a method for treating a viral infection in a subject, comprising administering to the subject an effective amount of an anti-infective peptide described herein (see, e.g., Section 5.1, Section 5.2 and Section 6) or a composition described herein (see, e.g., Section 5.4). In a specific embodiment, the virus is a virus described in Section 5.7 or 6. In another specific embodiment, the subject is a subject described in Section 5.6.

In another aspect, provided herein are methods for treating a disease in a subject which disease is caused by or associated with a viral infection, comprising administering to the subject an anti-infective peptide described herein (see, e.g., Section 5.1, Section 5.2 and Section 6) or a composition described herein (see, e.g., Section 5.4). In one embodiment, provided herein is a method for treating a disease in a subject which disease is caused by or associated with a viral infection, comprising administering to the subject an effective amount of an anti-infective peptide described herein (see, e.g., Section 5.1, Section 5.2 and Section 6) or a composition described herein (see, e.g., Section 5.4). In a specific embodiment, the virus is a virus described in Section 5.7 or 6. In another specific embodiment, the subject is a subject described in Section 5.6.

In a specific embodiment, the treatment of a viral infection or disease caused by or associated therewith with an anti-infective peptide described herein or composition thereof, or a combination of an anti-infective peptide described herein and another therapy results in a beneficial or therapeutic effect. In specific embodiments, the treatment of a viral infection or disease caused by or associated therewith with an anti-infective peptide described herein or composition thereof, or a combination of an anti-infective peptide described herein and another therapy results in one, two, three, four, five, or more, or all of the following effects: (i) the reduction or amelioration of the severity of a viral infection or a disease or a symptom caused by or associated therewith; (ii) the reduction in the duration of a viral infection or a disease or a symptom caused by or associated therewith; (iii) the regression of a viral infection or a disease or a symptom caused by or associated therewith; (iv) the reduction of the number/titer of virus; (v) the reduction in organ failure associated with a viral infection or a disease caused by or associated therewith; (vi) the reduction in hospitalization of a subject; (vii) the reduction in hospitalization length; (viii) the increase in the survival of a subject; (ix) the elimination of a viral infection or a disease or a symptom caused by or associated therewith; (x) the inhibition of the progression of a viral infection or a disease or a symptom caused by or associated therewith; (xi) the prevention of the spread of virus from a cell, tissue, organ or subject to another cell, tissue, organ or subject; and/or (xii) the enhancement or improvement the therapeutic effect of another therapy.

In another aspect, provided herein are methods for preventing a disease in a subject which disease is caused by or associated with a viral infection, comprising administering to the subject an anti-infective peptide described herein (see, e.g., Section 5.1, Section 5.2 and Section 6) or a composition described herein (see, e.g., Section 5.4). In one embodiment, provided herein is a method for preventing a disease in a subject which disease is caused by or associated with a viral infection, comprising administering to the subject an effective amount of an anti-infective peptide described herein (see, e.g., Section 5.1, Section 5.2 and Section 6) or a composition described herein (see, e.g., Section 5.4). In a specific embodiment, the virus is a virus described in Section 5.7 or 6. In another specific embodiment, the subject is a subject described in Section 5.6.

In a specific embodiment, the administration of an anti-infective peptide described herein or composition thereof, or a combination of an anti-infective peptide described herein and another therapy to a subject to prevent a disease caused by or associated with a viral infection results in one or more of the prophylactic/beneficial effects. In a specific embodiment, the administration of an anti-infective peptide described herein or composition thereof, or a combination of an anti-infective peptide described herein and another therapy to a subject to prevent a disease caused by or associated with a viral infection results in one, two or more, or all of the following effects: (i) the inhibition of the development or onset of a disease caused by or associated with a viral infection or a symptom thereof: (ii) the inhibition of the recurrence of a disease caused by or associated with a viral infection or a symptom associated therewith: and (iii) the reduction or inhibition in viral infection and/or replication.

An anti-infective peptide described herein or composition described herein may be delivered to a subject by a variety of routes. These include, but are not limited to, intranasal, intratracheal, oral, intradermal, intramuscular, intraperitoneal, transdermal, intravenous, conjunctival and subcutaneous routes. In some embodiments, an anti-infective peptide described herein or composition described herein is administered topically to a subject, for example, to the skin of a subject. In specific embodiments, an anti-infective peptide described herein or composition described herein is administered intranasally to the subject. In certain embodiments, an anti-infective peptide described herein or composition described herein is administered intramuscularly. In some embodiments, an anti-infective peptide described herein or composition described herein is administered subcutaneously to the subject. In certain embodiments, an anti-infective peptide described herein or composition described herein is administered intraperitoneally to the subject.

The amount of an anti-infective peptide described herein or composition which will be effective in the treatment and/or prevention of an infection or disease described herein will depend on a number of factors, including, e.g., the nature of the disease. The precise dose to be employed will also depend on the route of administration, and the seriousness of the infection or disease caused by or associated therewith. For example, effective doses may also vary depending upon means of administration, target site, physiological state of the patient (including age, body weight, health), whether the patient is human or an animal, other medications administered, and whether treatment is prophylactic or therapeutic.

In specific embodiments, "effective amount" of an anti-infective peptide or composition thereof administered to a subject refers to the amount of the anti-infective peptide or composition which is sufficient to achieve one, two, three, four, or more of the following effects: (i) reduce or ameliorate the severity of a microorganism, bacterial or viral infection, disease or symptom caused by or associated therewith; (ii) reduce the duration of a microorganism, bacterial or viral infection, disease or symptom caused by or associated therewith; (iii) prevent the progression of a microorganism, bacterial or viral infection, disease or symptom caused by or associated therewith; (iv) cause regression of a microorganism, bacterial or viral infection, disease or symptom caused by or associated therewith; (v) prevent the development or onset of a microorganism, bacterial or viral infection, disease or symptom caused by or associated therewith; (vi) prevent the recurrence of a microorganism bacterial or viral infection, disease or symptom caused by or associated therewith; (vii) reduce or prevent the spread of microorganism, bacteria or virus from one cell to another cell, one tissue to another tissue, or one organ to another organ; (viii) prevent or reduce the spread of a microorganism, bacteria, or virus from one subject to another subject; (ix) reduce organ failure associated with a microorganism, bacterial or viral infection; (x) reduce hospitalization of a subject; (xi) reduce hospitalization length; (xii) increase the survival of a subject with a microorganism, bacterial or viral infection, or disease caused by or associated therewith; (xiii) eliminate a microorganism, bacterial or viral infection, or disease caused by or associated therewith; (xiv) inhibit or reduce microorganism replication; (xv) reduce microorganism, bacterial or viral numbers/titer; and/or (xvi) enhance or improve the prophylactic or therapeutic effect(s) of another therapy.

In certain embodiments, the effective amount does not result in complete protection from a disease caused by or associated with a microorganism infection, but results in a lower titer or reduced number of microorganisms compared to an untreated subject with a microorganism infection. In certain embodiments, the effective amount results in a 0.5 fold, 1 fold, 1.5 fold, 2 fold, 3 fold, 4 fold, 5 fold, 6 fold, 7 fold, 8 fold, 9 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer/number of microorganisms relative to an untreated subject with a microorganism infection. In some embodiments, the effective amount results in a reduction in titer/number of microorganisms relative to an untreated subject with a microorganism infection of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of a microorganism include, but are not limited to, less severe symptoms of the infection, fewer symptoms of the infection and a reduction in the length of the disease caused by or associated with the infection.

In certain embodiments, the effective amount does not result in complete protection from a disease caused by or associated with a bacterial infection, but results in a lower titer or reduced number of bacteria compared to an untreated subject with a bacterial infection. In certain embodiments, the effective amount results in a 0.5 fold, 1 fold, 1.5 fold, 2 fold, 3 fold, 4 fold, 5 fold, 6 fold, 7 fold, 8 fold, 9 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer/number of bacteria relative to an untreated subject with a bacterial infection. In some embodiments, the effective amount results in a reduction in titer/number of bacteria relative to an untreated subject with a bacterial infection of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of bacteria include, but are not limited to, less severe symptoms of the infection, fewer symptoms of the infection and a reduction in the length of the disease caused by or associated with the infection.

In certain embodiments, the effective amount does not result in complete protection from a disease caused by or associated with a viral infection, but results in a lower titer or reduced number of viruses compared to an untreated subject with a viral infection. In certain embodiments, the effective amount results in a 0.5 fold, 1 fold, 1.5 fold, 2 fold, 3 fold, 4 fold, 5 fold, 6 fold, 7 fold, 8 fold, 9 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer/number of viruses relative to an untreated subject with a viral infection. In some embodiments, the effective amount results in a reduction in titer/number of viruses relative to an untreated subject with a viral infection of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of viruses include, but are not limited to, less severe symptoms of the infection, fewer symptoms of the infection and a reduction in the length of the disease caused by or associated with the infection.

In some embodiments, a subject is administered a unit dose of 10 mg to 300 mg of an anti-infective peptide described herein is administered once, twice or three times per day to treat a microorganism, bacterial or viral infection, or a disease caused by or associated with a microorganism, bacterial or viral infection. In certain embodiments, a subject is administered a unit dose of 10 mg to 50 mg, 10 mg to 100 mg, 10 mg to 150 mg, 10 mg to 150 mg, 10 mg to 200 mg, or 10 mg to 250 mg of an anti-infective peptide described herein is administered once, twice or three times per day to treat a microorganism, bacterial or viral infection, or a disease caused by or associated with a microorganism, bacterial or viral infection. In some embodiments, a subject is administered a unit dose of 50 mg to 100 mg, 50 mg to 150 mg, 50 mg to 150 mg, 50 mg to 200 mg, 50 mg to 250 mg or 50 mg to 300 mg of an anti-infective peptide described herein is administered once, twice or three times per day to treat a microorganism, bacterial or viral infection, or a disease caused by or associated with a microorganism, bacterial or viral infection. In certain embodiments, a subject is administered a unit dose of 100 mg to 150 mg, 100 mg to 150 mg, 100 mg to 200 mg, 100 mg to 250 mg or 100 mg to 300 mg of an anti-infective peptide described herein is administered once, twice or three times per day to treat a microorganism, bacterial or viral infection, or a disease caused by or associated with a microorganism, bacterial or viral infection.

In some embodiments, a subject is administered a unit dose of 10 mg to 300 mg of an anti-infective peptide described herein is administered once, twice or three times per day to prevent a disease caused by or associated with a microorganism, bacterial or viral infection. In certain embodiments, a subject is administered a unit dose of 10 mg to 50 mg, 10 mg to 100 mg, 10 mg to 150 mg, 10 mg to 150 mg, 10 mg to 200 mg, or 10 mg to 250 mg of an anti-infective peptide described herein is administered once, twice or three times per day to prevent a disease caused by or associated with a microorganism, bacterial or viral infection. In some embodiments, a subject is administered a unit dose of 50 mg to 100 mg, 50 mg to 150 mg, 50 mg to 150 mg, 50 mg to 200 mg, 50 mg to 250 mg or 50 mg to 300 mg of an anti-infective peptide described herein is administered once, twice or three times per day to prevent a disease caused by or associated with a microorganism, bacterial or viral infection. In certain embodiments, a subject is administered a unit dose of 100 mg to 150 mg, 100 mg to 150 mg, 100 mg to 200 mg, 100 mg to 250 mg or 100 mg to 300 mg of an anti-infective peptide described herein is administered once, twice or three times per day to prevent a disease caused by or associated with a microorganism, bacterial or viral infection.

5.5.1 Sterilization and Disinfecting Uses

In another aspect, provided herein is a method for disinfecting a biological surface or biological material, comprising contacting the surface or material with an anti-infective peptide described herein (see, e.g., Section 5.1, Section 5.2 and Section 6) or a composition described herein (see, e.g., Section 5.4). For example, in a specific embodiment, provided herein is a method for disinfecting a biological material, comprising contacting the biological fluid with an infective peptide described herein or a composition thereof. Exemplary biological materials include: whole blood; anti-coagulated whole blood (AWB); packed red cells obtained from AWB; platelet-rich plasma (PRP) obtained from AWB; platelet concentrate (PC) obtained from AWB or PRP; plasma obtained from AWB or PRP; red cells separated from plasma and resuspended in physiological fluid; platelets separated from plasma and resuspended in physiological fluid; other blood products; and non-blood cells. In one example, a method of disinfecting a biological material comprises contacting (e.g., combining or mixing) the anti-infective peptide or a composition thereof with the biological material (e.g., blood product) or biological surface for a certain period of time. In some embodiments, the anti-infective peptide is immobilized on a solid support or semi-solid and the biological material is a biological fluid that is a passed over or through the solid support. In certain embodiments, the method further comprises washing the biological material or biological surface with, e.g., a buffer rinse removes excess anti-infective peptides before the biological material or biological surface is used.

In certain embodiments, an anti-infective peptide is immobilized on an inanimate surface (e.g., a medical device) or a biological surface. The peptide may be immobilized by covalent or non-covalent means. The immobilized may be through a linker or be direct.

In one embodiment, one or more of the anti-infective peptides described herein is used as an additive in a cosmetic product or a personal hygiene product. In another embodiment, one or more of the anti-infective peptides described herein is used as an additive in an ointment or cream. In another embodiment, one or more anti-infective peptides described herein is used as an additive to soap.

In a specific embodiment, an anti-infective peptide described herein or a composition thereof is used as a functional nutrient (e.g., drink supplement). In another specific embodiment, an anti-infective peptide described herein or a composition thereof is used as a food supplement (e.g., nisin). In a specific embodiment, the anti-infective peptide or a composition comprising the same is used as a skincare product.

In another embodiment, an anti-infective peptide described herein or a composition thereof is used in cell culture or other laboratory techniques.

In another aspect, provided herein is a method for disinfecting an inanimate object (e.g., an inanimate surface or other non-biological surface, such as a countertop, medical instrument (e.g., a medical device and the like)), comprising contacting the object with a composition described herein (see Section 5.4). For example, in a specific embodiment, provided herein is a method for disinfecting an inanimate object (e.g., an inanimate surface or other non-biological surface, such as a countertop, medical instrument (e.g., a medical device and the like)), comprising contacting the object with an infective peptide described herein or a composition thereof for a certain period of time. In certain embodiments, the method further comprises washing the inanimate object with, e.g., a buffer rinse removes an excess anti-infective peptides before the object is used.

Examples of medical devices include those employed by a doctor, nurse, medical technician such as one who collects blood or blood products, or dentist (and as such "medical device" is meant to encompass "dental device"). The term "medical device" is intended to mean any tool employed in the checking, cleaning, and/or collection of fluid from or medical intervention of an animal or human body. Such tools include, without limitation, surgical instruments such as, but not limited to, probes, scalpels, clamps, forceps, needles, suction devices for removing saliva or blood including all nozzles, seals, tubing, filters, containers and reservoirs therein, endoscopes, optical fibers, transducers, wire, surgical loops, and in-line and out-line tubing and filters through which blood or blood product is passed prior to delivery to an individual and/or at the point of collection from an individual. Such medical devices can also serve as a solid support for immobilization of an anti-infective peptide, as discussed above.

In one embodiment, one or more of the anti-infective peptides described herein is used as an additive in a household or industrial cleaning product.

Also contemplated, are methods for reducing microorganism contamination of water or water containers such as found in swimming pools, hot-tubs, Jacuzzis, baths, and whirlpool baths, air-conditioners and humidifiers, involving contacting the water or water container with a composition with an anti-infective peptide disclosed herein of a certain period of time.

Sufficient periods of time for accomplishing disinfection using an anti-infective peptide disclosed herein are dependent upon the choice of peptide and the material to be disinfected. It can also be appreciated that useful anti-infective peptide concentrations and periods of time for disinfecting are interdependent. In certain embodiments, the composition used for disinfecting is not suitable for administration to a subject, e.g., to a human subject. In those instances where the composition is not going to be administered to a subject, a composition may comprise a concentration of an anti-infective peptide that would be unacceptably high concentrations for use in a subject and the formulation of the anti-infective peptide may be one that is not suitable for use in a subject. For example, the composition for use as a disinfective in circumstances where it is not intended for administration to a subject may comprise a surfactant (e.g., detergent), preservative, solvent (e.g., DMSO) disinfectant, compound that provides for a scent, or other compound that is not suitable for administration to a subject, e.g., a human, by any route.

In certain embodiments, the amount of an anti-infective peptide present in a composition for use in disinfecting is the amount sufficient to disrupt at least 80%, 85%, 90%, 95%, 96%, 97%, 98% or 99% of the membranes of a bacteria described in Section 5.7 or 6 in a bacterial culture. In some embodiments, the amount of an anti-infective peptide present in a composition for use in disinfecting is the amount sufficient to disrupt at least 80%, 85%, 90%, 95%, 96%, 97%, 98% or 99% of the envelope of a virus described in Section 5.7 or 6 in a cell culture. In certain embodiments, the amount of an anti-infective peptide present in a composition for use in disinfecting is the amount sufficient to disrupt at least 80%, 85%, 90%, 95%, 96%, 97%, 98% or 99% of the membranes of a bacteria described in Section 5.7 or 6 in a bacterial culture and disrupt at least 80%, 85%, 90%, 95%, 96%, 97%, 98% or 99% of the envelope of a virus described in Section 5.7 in a cell culture.

In certain embodiments, the amount of an anti-infective peptide present in a composition for use in disinfecting is the amount sufficient to kill at least 80%, 85%, 90%, 95%, 96%, 97%, 98% or 99% of a bacteria described in Section 5.7 or 6 in a bacterial culture. In some embodiments, the amount of an anti-infective peptide present in a composition for use in disinfecting is the amount sufficient to kill at least 80%, 85%, 90%, 95%, 96%, 97%, 98% or 99% of a virus described in Section 5.7 or 6 in a cell culture. In certain embodiments, the amount of an anti-infective peptide present in a composition for use in disinfecting is the amount sufficient to kill at least 80%, 85%, 90%, 95%, 96%, 97%, 98% or 99% of a bacteria described in Section 5.7 or 6 in a bacterial culture and kill at least 80%, 85%, 90%, 95%, 96%, 97%, 98% or 99% of a virus described in Section 5.7 in a cell culture.

A suitable temperature used will be selected so as to be compatible with the materials to be disinfected/sterilized. For example, where the material is a biological material, such as blood or component thereof, the blood or component thereof can be contacted with an anti-infective peptide under a temperature of 20° C. or greater, 25° C. or greater, or 30° C. or greater. pH and osmolality can also be adjusted as discussed previously herein provided that these conditions are consistent with maintaining the viability of the material to be disinfected/sterilized.

5.5.2 Combination Therapy

In various embodiments, an anti-infective peptide described herein see, e.g., Section 5.1, Section 5.2 and Section 6), or a composition described herein comprising such an anti-infective peptide (see, e.g., Section 5.4) may be administered to a subject in combination with one or more other therapies (e.g., antiviral, antibacterial, or immunomodulatory therapies). In some embodiments, a composition (e.g., a pharmaceutical composition) described herein may be administered to a subject in combination with one or more therapies. The one or more other therapies may be beneficial in the treatment or prevention of an infectious disease (e.g., disease caused by or associated with a viral or bacterial infection) or may ameliorate a symptom or condition associated with an infectious disease (e.g., disease caused by or associated with a viral or bacterial infection). In some embodiments, the one or more other therapies are pain relievers, anti-fever medications, or therapies that alleviate or assist with breathing. The term "combination" as used in the context of the administration of two or more therapies does not restrict the order in which one therapy is administered relative to another therapy. For example, an anti-infective peptide described herein or a composition thereof may be administered before, concomitantly with, or after the administration of another therapy to a subject. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In a specific embodiment, two or more therapies are administered within the same patient visit.

In some embodiments, a combination therapy comprises administration of two or more different anti-infective peptides described herein (e.g., in Section 5.1, Section 5.2 and Section 6).

5.6 Patient Population

As used herein, the terms "subject" and "patient" when used in the context of administration of an anti-infective peptide described herein or a composition thereof are used interchangeably to refer to an animal. In certain embodiments, a subject is a bird. In some embodiments, a subject is a mammal including a non-primate (e.g., a camel, donkey, zebra, cow, pig, horse, goat, sheep, cat, dog, rat and mouse) and a primate (e.g., a monkey, chimpanzee, and human). In certain embodiments, a subject is a non-human animal. In some embodiments, a subject is a farm animal (e.g., a donkey, cow, pig, horse, goat, or sheep) or pet (e.g., a cat or dog). In some embodiments, a subject is a canine. In certain embodiments, a subject is a feline. In some embodiments, a subject is a horse. In certain embodiments, animal subject is a cow. In a specific embodiment, a subject is a human.

In certain embodiments, an anti-infective peptide described herein (see, e.g., Section 5.1, Section 5.2 and Section 6) or composition described herein (see, e.g., Section 5.4) may be administered to a naïve subject, i.e., a subject that does not have a disease caused by an infectious agent described in Section 5.7 or 6, or has not been and is not currently infected with an infectious agent described in Section 5.7. In one embodiment, an anti-infective peptide or composition described herein is administered to a naïve subject that is at risk of acquiring an infection with an infectious agent described in Section 5.7 or 6. An anti-infective peptide or composition described herein may also be administered to a subject that is and/or has been infected with an infectious agent described in Section 5.7 or 6.

In certain embodiments, an anti-infective peptide or composition described herein is administered to a patient who has been diagnosed with an infection with an infectious agent described in Section 5.7 or 6. In some embodiments, an anti-infective peptide or composition described herein is administered to a patient infected with an infectious agent described in Section 5.7 or 6 before symptoms manifest or symptoms become severe (e.g., before the patient requires hospitalization)

5.7 Microorganisms

In a specific embodiment, a microorganism described herein is a bacterium. In a specific embodiment, the bacteria is Gram-positive. In a specific embodiment, the Gram-positive bacteria is *Staphylococcus aureus* (e.g., ATCC 29213), *enterococci, streptococci, Bacillus anthracia* (e.g., ATCC 14575), *Clostridum difficile* (e.g., ATCC 700057), or *Propionibacterium acnes* (e.g., ATCC 11827). In a specific embodiment, the *enterococci* is *Enterococcus faecalis* (e.g., ATCC 29212). In a specific embodiment, the *streptococci* is *Streptococcus pneumoniae* (e.g., ATCC 49619). In a specific embodiment, the bacteria is Gram-negative. In a specific embodiment, the Gram-negative bacteria is *Pseudomonas aeruginosa* (e.g., ATCC 27853), *Moraxella catarrhalis* (e.g., ATCC 25238), or *Haemophilus influenzae* (e.g., ATCC 10211). In a specific embodiment, the bacteria is methicillin-sensitive *Staphylococcus aureus*, is methicillin-resistant *Staphylococcus aureus*, Vancomycin-sensitive *enterococci*, Vancomycin-resistant *enterococci*, penicillin-sensitive *Streptococcus pneumonia*, penicillin-resistant *Streptococcus pneumonia*, ciprofloxacin-resistant bacteria, or clindamycin-resistant bacteria.

In a specific embodiment, the bacterium has an average particle diameter of between 50 nm and 1,200 nm. In a specific embodiment, the bacterium has an average particle diameter of between 50 nm and 200 nm, 50 nm and 300 nm, 50 nm and 400 nm, 50 nm and 500 nm, 50 nm and 600 nm, 50 nm and 700 nm, 50 nm and 800 nm, 50 nm and 900 nm, 50 nm and 1,000 nm, 50 nm and 1,100 nm, or 50 nm and 1,200 nm. In a specific embodiment, the bacterium has an average particle diameter of between 50 nm and 1,200 nm, 100 nm and 1,200 nm, 200 nm and 1,200 nm, 300 nm and 1,200 nm, 400 nm and 1,200 nm, 500 nm and 1,200 nm, 600 nm and 1,200 nm, 700 nm and 1,200 nm, 800 nm and 1,200 nm, 900 nm and 1,200 nm, or 1,000 nm and 1,200 nm. In a specific embodiment, the bacterium has an average particle diameter of between 50 nm and 300 nm, 100 nm and 500 nm, 300 nm and 700 nm, 500 nm and 900 nm, or 700 nm and 1,200 nm. In a specific embodiment, the bacterium has an average particle diameter of between 50 nm and 2,000 nm, 100 nm and 2,000 nm, 200 nm and 2,000 nm, 300 nm and 2,000 nm, 400 nm and 2,000 nm, 500 nm and 2,000 nm, 600 nm and 2,000 nm, 700 nm and 2,000 nm, 800 nm and 2,000 nm, 900 nm and 2,000 nm, 1,000 nm and 2,000 nm, 1,200 nm and 2,000 nm, 1,500 nm to 2,000 nm, or 1,750 nm and 2,000 nm. In a specific embodiment, the bacterium has an average particle diameter of between 50 nm and 300 nm, 100 nm and 500 nm, 300 nm and 700 nm, 500 nm and 900 nm, or 700 nm and 1,200 nm. In a specific embodiment, the average particle diameter is the average diameter of the major axis.

In a specific embodiment, a microorganism described herein is a virus. In a specific embodiment, the virus is a virus belonging to the Flaviviridae, Togaviridae, Filoviridae, Retroviridae, Bunyaviridae, Poxviridae, or Arenaviridae family. In a specific embodiment, the virus is dengue virus (DENV), Chikungunya virus (CHIKV), Ebola virus (EBOV), human immunodeficiency virus 1 (HIV-1), or influenza virus. In a specific embodiment, the virus belonging to the Flaviviridae family is DENV. In a specific embodiment, the DENV is serotype 1 (DENV-1). In a specific embodiment, the DENV-1 is DENV-1 PRS41393 (see, e.g., Warfield, Kelly L., et al. "Inhibition of endoplasmic reticulum glucosidases is required for in vitro and in vivo dengue antiviral activity by the iminosugar uv-4." Antiviral research 129 (2016): 93-98, for a description of the virus.) In a specific embodiment, the DENV is serotype 2 (DENV-2). In a specific embodiment, the DENV-2 is DENV-2 New Guinea C (see, e.g., ATCC No. VR-1584). In a specific embodiment, the DENV is serotype 3 (DENV-3). In a specific embodiment, the DENV-3 is DENV-3 H37 (see, e.g., GenBank Accession No. M93130). In a specific embodiment, the DENV is serotype 4 (DENV-4). In a specific embodiment, the DENV-4 is DENV-4 H24 (see, e.g., GenBank Accession No. AY947539). In a specific embodiment, the virus belonging to the Flaviviridae family is yellow fever virus (YFV). In a specific embodiment, the YFV is YFV 17D (see, e.g., GenBank Accession No. X03700 and Rice, Charles M., et al. "Nucleotide sequence of yellow fever virus: implications for flavivirus gene expression and evolution." Science 229.4715 (1985): 726-733). In a specific embodiment, the virus belonging to the Flaviviridae family is Japanese encephalitis virus (JEV). In a specific embodiment, the JEV is JEV 14-14-2 (see, e.g., GenBank Accession No. JN604986). In a specific embodiment, the virus belonging to the Flaviviridae family is zika virus (ZIKV). In a specific embodiment, the ZIKV is ZIKV FSS 13025 (see, e.g., GenBank accession No. JN860885 and Haddow, Andrew D., et al. "Genetic characterization of Zika virus strains: geographic expansion of the Asian lineage." PLoS Negl Trop Dis 6.2 (2012): e1477). In a specific embodiment, the virus belonging to the Togaviridae family is CHIKV. In a specific embodiment, CHIKV is CHIKV 181/25 (see, e.g., GenBank Accession No. L37661). In a specific embodiment, the virus belonging to the Togaviridae family is Venezuelan equine encephalitis virus (VEEV). In a specific embodiment, the VEEV is VEEV TC-83 (see, e.g., GenBank Accession No. L01443).

In a specific embodiment, the virus belonging to the Filoviridae family is EBOV or Marburg virus (MARV). In a specific embodiment, the virus belonging to the Retroviridae family is HIV-1. In a specific embodiment, the HIV-1 is HIV-1$_{BaL}$ (see, e.g., GenBank Accession Number: DQ318211). In a specific embodiment, the HIV-1 is HIV-1 RF (see, e.g., Otto M J, Garber S, Winslow D, Reid C D, Aldrich P, Jadhav P K, Patterson C E, Hoge C N, Cheng Y S. In vitro isolation and identification of HIV variants with reduced sensitivity to C-2 symmetrical inhibitors of HIV-1 protease. Proc Natl Acad Sci USA 90:7543-7547, 1993). In a specific embodiment, the virus belonging to the Arenaviridae family is Junin virus. In a specific embodiment, the JUNV is JUNV Candid #1. See, e.g., Emonet, Sebastien F., et al. "Rescue from cloned cDNAs and in vivo characterization of recombinant pathogenic Romero and live-attenuated Candid #1 strains of Junin virus, the causative agent of Argentine hemorrhagic fever disease." Journal of virology 85.4 (2011): 1473-1483, for a description of Junin virus. In a specific embodiment, the virus belonging to the Bunyaviridae family is Rift Valley fever virus (RVFV). In a specific embodiment, the RVFV is RVFV MP12 (see, e.g., GenBank Accession No. DQ380208.1). In a specific embodiment, the virus belonging to the Poxviridae family is vaccinia virus (VACV). In a specific embodiment, the VACV is VACV NYCBH (see, e.g., Monath, Thomas P., et al. "ACAM2000 clonal Vero cell culture vaccinia virus (New York City Board of Health strain)—a second-generation smallpox vaccine for biological defense." International journal of infectious diseases 8 (2004): 31-44).

In a specific embodiment, the virus is an enveloped virus having an average particle diameter of between 25 nm and 200 nm. In a specific embodiment, the virus is an enveloped virus having an average particle diameter of between 25 nm and 75 nm, 50 nm and 100 nm, 75 nm and 125 nm, 100 nm and 150 nm, 125 nm and 175 nm, or 150 nm and 200 nm. In a specific embodiment, the virus is an enveloped virus having an average particle diameter of between 25 nm and 75 nm, 25 nm and 100 nm, 25 nm and 125 nm, 25 nm and 150 nm, 25 nm and 175 nm, or 25 nm and 200 nm. In a specific embodiment, the virus is an enveloped virus having an average particle diameter of between 25 nm and 200 nm, 50 nm and 200 nm, 75 nm and 200 nm, 100 nm and 200 nm, 125 nm and 200 nm, 150 nm and 200 nm, or 175 nm and 200 nm. In a specific embodiment, the virus is an enveloped virus having an average particle diameter of less than 25 nm, less than 50 nm, less than 75 nm, less than 100 nm, less than 125 nm, less than 150 nm, or less than 175 nm.

In specific embodiments, the bacteria is a bacteria described in Section 6.

In specific embodiments, the virus is a virus described in Section 6.

5.8 Assays

Also provided herein are assays for use in combination with the anti-infective peptides described herein (see, e.g., Section 5.1, Section 5.2, and/or Section 6) and/or the methods of use of said anti-infective peptides described herein (see, e.g., Section 5.5). See, also, Section 6 for assays that can be utilized in connection with the anti-infective peptides described herein. In specific embodiments, an anti-infective peptide described herein has a low EC50, IC50, and MIC and a high CC50 and MHC.

5.8.1 EC50

The EC50 of an anti-infective peptide described herein can be determined using any technique known to one skilled in the art or described herein (see, e.g., Section 6). 50% efficacy concentration (EC50) using untreated, infected cells as 0% efficacy and uninfected cells as 100% efficacy (XLfit 5.4; equation 205). It is a 4-PL curve fit.

5.8.2 MIC

The MIC of an anti-infective peptide described herein can be determined using any technique known to one skilled in the art or described herein (see, e.g., Section 6). MIC is recorded as the lowest concentration of drug that inhibited visible growth of the organism. It can be determined visually (e.g., colony growth on agar plate after incubation period) or by absorbance measurements.

5.8.3 Therapeutic Index

The therapeutic index of an anti-infective peptide described herein can be determined using any technique known to one skilled in the art or described herein (see, e.g., Section 6). The therapeutic index of an anti-infective peptide described herein can be calculated by the ratio CC50/EC50 ratio. See, e.g., Section 6 for methods for calculating the CC50/EC50 ratio. In a specific embodiment, an anti-infective peptide described herein has a TI over 10.

5.8.4 Circular Dichroism Spectroscopy

The helicity of an anti-infective peptide described herein may be evaluated by circular dichroism (CD) spectroscopy. Circular dichroism spectroscopy can be performed using any technique known to one skilled in the art or described herein (see, e.g., Section 6).

CD experiments may be conducted on a spectrometer (for example, an AVIV Model 420 spectrometer (AVIV Biomedical, Lakewood, NJ, USA)) using a cuvette (e.g., a quartz cuvette) with a 1 mm path length (e.g., by Hellma). Spectral data are collected with a step size of, e.g., 0.5 nm and averaging time of, e.g., 4 s. All spectra are recorded at, e.g., 25° C. from 190 to 260 nm using a bandwidth of 1-nm and averaged over three scans. The CD spectra may be recorded before and after the addition of 2.5 mM POPC lipid vesicles to 50 µM peptide. Baseline scans in buffer only or liposomes only may also be performed using the same instrument settings, and this contribution may be subtracted from respective data scans with peptides. The corrected spectra may be expressed in mean residue molar ellipticity ($\Theta$), and the fractional helicity of peptides is calculated as follows (J. D. Morrisett, J. S. David, H. J. Pownall, A. M. Gotto Jr, Interaction of an apolipoprotein (apoLP-alanine) with phosphatidylcholine. Biochemistry 12, 1290-1299 (1973)): fH= $([\Theta]222-3,000)/(-36,000-3000)$, where $[\Theta]222$ is the molar ellipticity at 222 nm.

CD may be performed as described in Section 6.

5.8.5 Cytopathic Effect (CPE) Assays

Antiviral activity was of an anti-infective peptide described herein may be determined according to any method known to the skilled artisan or described herein (see, e.g., Section 6).

For example, CPE can be determined by seeding cells (e.g., Vero cells) at a certain concentration (e.g., 10,000 cells per well) in plates (e.g., 96-well plates) and incubated for a certain period of time (e.g., overnight). The peptides are serially diluted (e.g., serially diluted 2-fold) in serum-free media (e.g., MEM) and the viruses are prepared for a final multiplicity of infection (MOI) of 0.1. The peptide dilutions are incubated with the virus for a certain period of time (e.g., one hour at 37° C.) before infecting the cells. Media (e.g., MEM) supplemented with 2% FBS (and Pen/Strep and L-gln) is added for a final FBS concentration of 1%. After a certain period of time (e.g., 5 days) the cells are fixed and stained with 0.1% crystal violet in 5% glutaraldehyde solution. Optical density is determined at 540 nm and used to calculate the 50% efficacy concentration (EC50) using untreated, infected cells as 0% efficacy and uninfected cells as 100% efficacy (XLfit 5.4; equation 205).

CPE assays may be performed as described in Section 6.

5.8.6 IC50

The IC50 of an anti-infective peptide described herein can be determined by any method known to the skilled artisan or described herein.

For example, cells (e.g., Vero cells) are seeded at a certain concentration $1 \times 10^5$ cells per) in plates (e.g., in 24-well plates) and incubated overnight. The next day, serial dilutions (e.g., 6 two-fold serial dilutions) of the peptide are prepared. Peptide dilutions are incubated with virus for a certain period of time (e.g., 1 hour at 37° C.). Cells are infected for a certain period of time (e.g., 1 hour) after and the inoculum is removed. Fresh medium is added and cells are incubated at, e.g., 37° C. for 3 days. Supernatants are harvested, cleared of cell debris and may be stored at −80° C. The cells are seeded at a certain concentration (e.g., $1 \times 10^5$ cells) per well in plates (e.g., 24-well plates) and incubated overnight. The next day, serial dilutions (e.g., 4 ten-fold serial dilutions) of the supernatants are prepared. Cells are infected with the dilutions for a certain period of time (e.g., 1 hour at 37° C.). The inoculum is removed and 0.8% methylcellulose is added. After 4-10 days, depending on the virus, plates are analyzed for plaques using crystal violet. The IC50 is calculated based on the number of plaques relative to the virus-only using a 4-PL curve fit.

IC50 may be determined as described in Section 6.

5.8.7 Cytotoxicity Assays

CC50 can be determined by any method known to the skilled artisan or described herein. For example, cytotoxicity assays may be performed in Vero cells may be performed using the CellTiter-Glo kit (Promega #G7570) as follows: (i) serial dilutions of an anti-infective peptide are prepared in media (e.g., MEM) (supplemented with 1% FBS, 1× Penicillin/Streptomycin, 1× L-gln); (ii) a certain amount of cells (e.g., $1 \times 10^4$ Vero cells (ATCC #CCL-81)) are seeded in plates (e.g., black-walled 96-well plates) and are incubated with the dilutions for a certain period of time (e.g., one hour at two-times the final concentration) in serum-free media (e.g., MEM); (iii) supplemented media (e.g., MEM) is then added to final concentration and the cells are incubated for a certain period of time (e.g., 3, 6, or 9 days); and (iv) cell survival is determined by luciferase activity as described in the manufacturer's protocol.

Cytotoxicity assays may be performed on cells relevant to the vaginal and rectal compartments and may be performed by any method known to the skilled artisan or described herein. For example, Ca Ski, HEC1A and Caco-2 cells are added to wells (e.g., 96-well flat bottomed plate) a certain period of time (e.g., 24 hours prior to the addition of compound) at a density of cell concentration (e.g., $5 \times 10^4$ cells/well) in a certain total volume (e.g., 200 µL); concentrations of the peptide are serially diluted (e.g., in serially diluted two-fold concentrations) and added in a certain volume (e.g., 200 µL) in triplicate to the seeded cells following removal of the media; the plates are incubated for a certain period of time (e.g., 24 hours at 37° C./5% $CO_2$); following incubation, the cells are washed three times with media (e.g., RPMI-1640) without additives; a certain volume (e.g., two-hundred microliters (200 µL)) of complete medium for each specified cell line is then added to the plates and allowed to incubate at 37° C./5% $CO_2$ for a certain period of time (e.g., an additional 24 hours); and cellular toxicity is evaluated using the tetrazolium dye XTT.

The CC50 value (50% reduction in cell viability) is determined using linear regression analysis.

In specific embodiments, the CC50 is determined in human cells or cell lines. Non-limiting examples of human cell lines that can be utilized to evaluate the CC50 of an anti-infective peptide described herein are CaSki (ATCC CRL-1550), HEC1A (ATCC HTB-112), ME180 (ATCC HTB-33), and Caco-2 (ATCCHTB-37) cells. In specific embodiments, the CC50 is determined in human peripheral blood mononuclear cells. In specific embodiments, the CC50 is determined in MT-2 cells, which may be prepared by co-culturing normal human cord leukocytes with leukemic T-cells. In specific embodiments, the CC50 is determined in non-human cells. Non-limiting examples of non-human cell lines that can be used to evaluate the CC50 of an anti-infective peptide described herein are Vero (e.g., Vero E6 cells, ATTC CRL-1586), Madin Darby canine kidney cells (MDCK, ATCC CCL-34), and C6/36 (ATCC CRL-1660) cells.

CC50 may be determined as described in Section 6.

5.8.8 Hemolytic Assays

Hemolytic activity of an anti-infective peptide described herein can be performed according to any method known to the skilled artisan or described herein. Hemolytic activity may be determined as described in Section 6.

For example, lytic activity against human erythrocytes can be measured using a method adapted from Oren et al. (Z.

Oren, Y. Shai, Selective lysis of bacteria but not mammalian cells by diastereomers of melittin: structure-function study. Biochemistry 36, 1826-1835 (1997)). In particular, fresh human red blood cells (hRBC) are rinsed and washed thrice with phosphate-buffered saline (PBS) solution, centrifuged for 10 minutes at 900 g, and re-suspended in PBS buffer at an erythrocyte concentration of 8.0% (v/v). Equal volumes of peptide, resuspended in 10 mM PBS buffer, are added to the hRBCs in order to achieve a final concentration of 4% (v/v) hRBC in a total volume of 100 µL and incubated at 37° C. for 1 hour, with gentle agitation. Upon incubation, the samples are centrifuged at 1500 g for 5 minutes. Hemoglobin release is measured by absorbance measurement of the supernatant at 540 nm. Controls for 0% hemolysis and 100% hemolysis are obtained by suspending hRBCs in PBS and 1 wt % Triton X, respectively. Percentage of hemolysis is calculated according to the following formula: Percentage hemolysis=[$Abs_{pept}$-$Abs_{negative\ control}$]/[$Abs_{positive\ control}$-$Abs_{negative\ control}$]×100%, where Abs is the absorbance value (a.u.). The CC50 value is defined as 50% hemolysis.

5.8.9 Bacterial Viability Tests

The viability of bacteria treated with an anti-infective peptide described herein can be determined by any method known to the skilled artisan or described herein. Bacterial viability may be determined as described in Section 6.

For example, bacteria can be grown in media (e.g., MRS media (Becton Dickinson catalog #288130)), which allows for their growth. Different bacteria have different growth requirements and this should be considered when assessing bacterial viability. Bacterial stocks can be prepared and stored in solution (e.g., 15% glycerol) at −80° C. Broth (e.g., MRS broth) may prepared by dissolving a certain weight of appropriate powder (e.g., 55 grams) in a certain volume (e.g., 1 L) of deionized water. The broth is boiled to dissolve the powder completely and sterilized at a certain temperature (e.g., 121° C./17.5 psi) for a certain period of time (e.g., 15 minutes). Following sterilization, the broth may be stored at a certain temperature (e.g., 4° C.) prior to use. Broth (e.g., MRS broth) is inoculated using a loop (e.g., a 10 µL loop) of each bacterial strain from stocks (e.g., glycerol stocks) and the cultures are incubated (e.g., aerobically or anaerobically (e.g., in anaerobic jars using GasPak EZ Anaerobic Container System pouches (BD, catalog #260678)) for a certain period of time (e.g., 24 hours at 37° C.). The resultant culture may be used to prepare freshly grown liquid stocks using the same procedure. After the final incubation, the bacterial density is adjusted to an OD625 of a certain level (e.g., 0.06) in broth (e.g., MRS broth). Serial dilutions (e.g., six serial half-logarithmic dilutions) of the test agent are prepared and added in triplicate in a certain volume (e.g., 100 µL) to a well (e.g., a 96-well round bottom plate). As an assay control, serial dilutions (e.g., six serial two-fold dilutions) of a control agent (e.g., Penicillin/Streptomycin solution) at the highest test concentration (e.g., 1.25 U/mL/1.25 µg/mL) is prepared and added in triplicate to a well (e.g., a 96-well round bottom plate). Each culture of bacteria with an adjusted density (e.g., as described above) is added to the appropriate wells of the plate. The cultures are incubated (e.g., aerobically or anaerobically) for a certain period of time (e.g., 24 hours) as described above and bacterial growth is evaluated spectrophotometrically at a certain wavelength (e.g., 490 nm) using a spectrophotometer (e.g., a Spectramax 340 PC384 (Molecular Devices)).

5.8.10 Viable Count Assay and Colony Forming Unit Determination

The ability of an anti-infective peptide to inhibit bacteria growth can be determined using viable count assays to determine the colony forming units (CFU). The number CFU can be determined by any assay known to one skilled in the art or described herein. For example, to perform a viable count assay and determine the colony forming unit, bacteria, inoculated from an overnight culture are grown to mid-logarithmic phase in medium (e.g., LB medium). A certain concentration of bacteria (e.g., a certain volume (e.g., 100 µL of bacteria ($1.9 \times 10^7$ CFU/mL)) resuspended in 10 mM phosphate buffer (PB) is incubated with an equal volume of peptides (e.g., 10 µM) at a certain temperature (e.g., 37° C.) for a certain period of time (e.g., 3 hours). Serial dilution of the incubation mixtures are plated on agar plates (e.g., MH agar plates), followed by incubation at a certain temperature (e.g., 37° C.) for a certain period of time (e.g., overnight) and CFU determination. The effect of physiological salt (150 mM NaCl) may be analyzed by resuspending the bacteria and peptide in 10 mM phosphate buffer saline (PBS).

5.9 Kits

Provided herein is a pharmaceutical pack or kit comprising one or more containers filled with one or more of the ingredients of the compositions (e.g., pharmaceutical compositions) described herein, such as one or more anti-infective peptides described herein (see, e.g., Section 5.1, Section 5.2, and/or Section 6) provided herein. In one embodiment, a kit comprises one or more anti-infective peptides described herein (see, e.g., Section 5.1, Section 5.2, and/or Section 6) or a composition thereof (see, e.g., Section 5.4), in one or more containers. In specific embodiments, the kit comprises instructions for using an anti-infective peptide or composition thereof. In another specific embodiment, a notice in the form prescribed by a governmental agency regulating the manufacture, use or sale of pharmaceuticals or biological products, which notice reflects approval by the agency of manufacture, use or sale for human administration, is included in the kit.

In a specific embodiment, the kit comprises a first vial containing a lyophilized composition comprising 200 mg to 300 mg of an anti-infective peptide described herein.

In a specific embodiment, the kit comprises a first vial containing a lyophilized composition comprising 200 mg to 300 mg of an anti-infective peptide described herein and second vial containing 1 mL of an aqueous solution. In a specific embodiment, the aqueous solution is sterile water.

In a specific embodiment, the kit comprises a first vial containing a pharmaceutical composition comprising 200 mg to 300 mg of an anti-infective peptide described herein and second vial containing 1 mL of an aqueous solution. In a specific embodiment, the aqueous solution is sterile water.

The kits encompassed herein can be used in the above methods (see, e.g., Section 5.5, Section 5.7, and Section 6).

6. EXAMPLES

6.1 Example 1

Broad-Spectrum Anti-Infective Peptides

TABLE 6

Amino Acid Sequence of Anti-Infective Peptides.

| Peptide | Amino Acid Sequence (SEQ ID NO) |
|---|---|
| P1 or TSG001 | SGSWLRDVWTWLQSKL (SEQ ID NO: 1) |
| P2 or TSG002 | GSSWLRDVWTQSKL (SEQ ID NO: 2) |
| P3 or TSG003 | GSSWLRDVWTWLQSAL (SEQ ID NO: 3) |
| P4 or TSG004 | GSSWLRDVWTKLQSWL (SEQ ID NO: 4) |
| P5 or TSG005 | GSSWLRDIWTKLQSWL (SEQ ID NO: 5) |
| P6 or TSG006 | GSSWLRDIWTALQSWL (SEQ ID NO: 6) |
| P7 or TSG007 | GSSWLRDILTALQSLL (SEQ ID NO: 7) |
| P8 or TSG008 | AGSWLRDIWTWLQSAL (SEQ ID NO: 8) |
| P9 or TSG009 | AGSWLRDILTLLQSAL (SEQ ID NO: 9) |

TABLE 7

Antibacterial Spectrum of Anti-infective Peptide P1 (otherwise referred to as TSG001) (SEQ ID NO: 1).

| Organism Name | MIC (μM) | Therapeutic Index |
|---|---|---|
| Staphylococcus aureus (MSSA) | 2 | 20 |
| Staphylococcus aureus (MRSA) | 4 | 10 |
| Staphylococcus aureus (MRSA) | 2 | 20 |
| Enterococcus faecalis (VSE) | 2 | 20 |
| Enterococcus faecalis (VRE) | 4 | 10 |
| Enterococcus faecium (VRE) | 2 | 20 |
| Streptococcus pneumoniae (PSSP) | 8 | 5 |
| Streptococcus pneumoniae (PRSP) | 8 | 5 |
| Streptococcus pyogenes | 4 | 10 |

TABLE 7-continued

Antibacterial Spectrum of Anti-infective Peptide P1 (otherwise referred to as TSG001) (SEQ ID NO: 1).

| Organism Name | MIC (μM) | Therapeutic Index |
|---|---|---|
| Streptococcus agalactiae | 8 | 5 |
| Streptococcus salivarius | 4 | 10 |
| Bacillus anthracis Sterne | 1 | 39 |
| Mycobacterium smegmatis | 16 | 2 |
| Haemophilus influenzae | 4 | 10 |
| Moraxella catarrhalis | 1 | 78 |
| Clostridium difficile | 16 | 2 |
| Propionbacterium acnes | 8 | 5 |

MIC means minimum inhibitory concentration.

TABLE 8

Antiviral Against BSL-4 Level Viruses. Ebola and Marburg viruses were tested. TSG1 and TSG2 refer to TSG001 (SEQ ID NO: 1) and TSG002 (SEQ ID NO: 2) peptides, respectively. The values are the EC50 values (μM). The X . . . X designation refers to pegylated versions. The pegylated version of TSG001 peptide retained acceptable levels of high antiviral activity.

| | EBOV | MARV |
|---|---|---|
| TSG1 (SEQ ID NO: 1) | 0.934 | 0.637 |
| TSG1 (SEQ ID NO: 2) | 1.015 | 0.922 |
| TSG X1X | 13.45 | 14.35 |
| TSG X2X | 29.91 | 44.34 |

TABLE 9

Cytotoxicity Against Standard Human Cell Lines. The values are the CC50 values (μM).

| | CC50 [μM] | | |
|---|---|---|---|
| | Day 3 | Day 6 | Day 8 |
| AH (control) | 192.44 | 127.46 | 190.45 |
| C5A (control) | 41.73 | 28.99 | 144.95 |
| P1 (SEQ ID NO: 1) | 40.83 | 43.12 | 153.39 |
| P2 (SEQ ID NO: 2) | 367.4 | 35.77 | 16.13 |
| P3 (SEQ ID NO: 3) | 24.52 | 21.29 | 38.63 |
| P4 (SEQ ID NO: 4) | 111.03 | 81.11 | 114.48 |
| P6 (SEQ ID NO: 6) | 14.92 | 15.89 | 17.45 |
| Cidofovir | >375 | N/D | N/D |
| 6-azauridine | >10 | N/D | N/D |
| VEEV inhibitor | >50 | N/D | N/D |
| Ribavirin | >750 | >750 | >750 |

N/D = not determined.

TABLE 10

Antiviral Activity Against BSL-2 Level Viruses. The values are the EC50 values (μM). 1 h refers to samples in which the virus was preincubated with the indicated peptides for one hour. 0 h refers to samples in which the peptides/controls were added to the cells directly following infection.

| | 6-azaurdine | | Cidofovir | | AH Peptide | | C5A Peptide | | P1 | | P2 | |
|---|---|---|---|---|---|---|---|---|---|---|---|---|
| | 1 hr | 0 hr | 1 hr | 0 hr | 1 hr | 0 hr | 1 hr | 0 hr | 1 hr | 0 hr | 1 hr | 0 hr |
| CHIKV 181/25 | 0.29 | 0.17 | | | 6.01 | 17.98 | 3.09 | >12.5 | 2.52 | 2.24 | 3.41 | 3.21 |
| DENV-1 PRS41393 | | | | | 2.55 | 13.93 | 0.65 | 5.28 | 2.04 | 3.42 | 1.55 | 3.87 |
| DENV-2 New Guinea C | | | | | 0.18 | >18.75 | 0.34 | 4.76 | 1.95 | 3.91 | 1.68 | 2.74 |
| DENV-3 H37 | | | | | 7.22 | 17.86 | 1.93 | 3.86 | 1.90 | 6.43 | 2.65 | 5.09 |
| DENV-4 H241 | | | | | 3.46 | 10.38 | 1.31 | 1.65 | 1.64 | 3.50 | 1.88 | 3.97 |
| JEV-14-14-2 | | | | | 0.54 | >18.75 | 0.47 | 2.95 | 2.01 | 4.26 | 2.40 | 4.06 |
| JUNV Candid #1 | | | | | >75 | >75 | >75 | >75 | >75 | >75 | >75 | >75 |
| LACV H44-71017 | | | | | 7.09 | >50 | 1.22 | 8.65 | 1.70 | >12.5 | 2.03 | 5.51 |
| RVFV MP12 | | | | | 5.11 | 33.67 | 0.77 | 4.95 | 1.84 | 6.39 | 1.43 | 7.12 |
| VACV NYCBH | | | >375 | >375 | >50 | >50 | >12.5 | >12.5 | >12.5 | >12.5 | >12.5 | >12.5 |
| VEEV TC-83 | | | | | >50 | >50 | >12.5 | >12.5 | >12.5 | >12.5 | 10.67 | >12.5 |
| YFV 17D | | | | | 21.72 | >50 | 0.29 | 8.35 | 1.53 | 11.42 | 2.18 | 7.50 |

1 h: preincubation of virus with peptides for 1 h
0 h: addition of peptides/control directly following infection

TABLE 11

Antiviral Activity Against BSL-2 Level Viruses. The values are the EC50 values (μM).

| | P3 | | P4 | | P6 | | Ribavirin | | VEEV inhibitor | |
|---|---|---|---|---|---|---|---|---|---|---|
| | 1 hr | 0 hr | 1 hr | 0 hr | 1 hr | 0 hr | 1 hr | 0 hr | 1 hr | 0 hr |
| CHIKV 181/25 | 2.18 | 6.21 | 7.69 | 9.52 | 3.44 | 6.98 | | | | |
| DENV-1 PRS41393 | 3.37 | 6.12 | 8.51. | 6.24 | 1.45 | 1.56 | 144.29 | 205.65 | | |
| DENV-2 New Guinea C | 1.73 | 7.10 | 6.26 | 8.63 | 0.67 | 2.65 | 266.81 | 359.95 | | |
| DENV-3 H37 | 1.73 | 6.36 | 6.14 | 17.54 | 1.49 | 1.63 | 207.81 | 175.95 | | |
| DENV-4 H241 | 1.91 | 6.66 | 7.21 | 6.50 | 1.50 | 2.11 | 252.85 | 394.92 | | |
| JEV-14-14-2 | <18.75 | 16.26 | 4.68 | >75 | 1.63 | >200 | >750 | 12.32 | | |
| JUNV Candid #1 | >75 | >75 | >75 | >75 | 7.98 | 1.09 | 73.20 | 63.73 | | |
| LACV H44-71017 | 2.07 | 12.06 | 4.42 | 31.96 | 2.47 | 10.29 | 161.03 | 142.94 | | |
| RVFV MP12. | 3.27 | 7.20 | 9.02 | 19.28 | 1.20 | 4.36 | 124.17 | 140.41 | | |
| VACV NYCBH | >12.5 | >12.5 | >50 | >50 | 7.91 | >50 | | | | |
| VEEV TC-83 | 11.24 | >12.5 | 37.27 | >50 | 4.07 | >12.5 | | | >50 | >50 |
| YFV 17D | 2.14 | 11.20 | 7.99 | 34.99 | 0.79 | 3.50 | 202.51 | 257.63 | | |

1 h: preincubation of virus with peptides for 1 h
0 h: addition of peptides/control directly following infection

6.1.1 Toxicity of Anti-Infective Peptides

To determine the toxicity of the peptides in Vero cells on days 3, 6, and 8 (Table 9), cells were seeded in black-walled 96-well plates and incubated overnight. The next day, serial dilutions of the test articles were prepared. The growth medium was aspirated from the cells and the compound dilutions were added. Cells that were incubated with medium only served as controls. After 3, 6, and 8 days, the medium was aspirated (one set of plates per day) and cells were lysed for evaluation of the ATP content using Promega's CelltiterGlo kit. The resulting luciferase luminescence was quantified and used to calculate the CC50 using a 4-PL curve fit. The AH peptide used as control has the following amino acid sequence SGSWLRDVWD-WICTVLTDFKTWLQSKL (SEQ ID NO:10). The C5A peptide used as control has the following amino acid sequence SWLRDIWDWICEVLSDFK (SEQ ID NO:11).

6.1.2 Antiviral Activity of Anti-Infective Peptides

To determine the antiviral activity of the peptides (Table 10 and Table 11), Vero cells were seeded in 96-well plates and incubated overnight. The next day, serial dilutions of the test articles were prepared in medium. Two conditions were evaluated for all peptides: (1) preincubation of the virus with peptide dilutions; and (2) addition of the peptide dilutions immediately after infection. The preincubation condition was performed as follows: (i) peptide dilutions were prepared in medium and incubated with virus for one hour at 37° C.; (ii) control inhibitors and medium only were incubated in parallel; and (iii) Vero cells were infected with the preincubation mixes and incubated for a virus-specific time. The no preincubation condition was performed as follows: (i) Vero cells were infected with the viruses for one hour; (ii) peptide dilutions were prepared in medium and added to the infected cells; (iii) control inhibitors and medium only were incubated in parallel; and (iv) cells were incubated for the virus-specific time at 37° C. After incubation, cells were then fixed and stained with a crystal violet/glutaric dialdehyde solution. The optical density was determined and the EC50 was calculated using the uninfected (cells only) control as 0% CPE and the controls without compound (virus only) as 100% CPE using a 4-PL curve fit of the OD. Incubation times were as follows: CHIKV 181/25: 3 days; DENV-1 PRS41393: 5 days; DENV-2 New Guinea C: 5 days; DENV-3 H87: 5 days; DENV-4 H241: 5 days; JEV 14-14-2: 10 days; JUNV Candid #1: 8 days; LACV H44-71017: 4 days; RVFV MP12: 4 days; VACV NYCBH: 4 days; VEEV TC-83: 3 days; and YFV 17D: 6 days. The days on which cytotoxicity was measured times are as follows: CHIKV 181/25: 3 days; DENV-1 PRS41393: 6 days; DENV-2 New Guinea C: 6 days; DENV-3 H87: 6 days; DENV-4 H241: 6 days; JEV 14-14-2: 8 days; JUNV Candid #1: 8 days; LACV H44-71017: 3 days; RVFV MP12: 3 days; VACV NYCBH: 3 days; VEEV TC-83: 3 days; and YFV 17D: 6 days.

6.1.3 Antibacterial Activity of Anti-Infective Peptides

Table 7 provides a summary of the antibacterial spectrum of anti-infective peptide P1 (SEQ ID NO:1). In summary, the anti-infective peptide P1 (also referred to herein as "TSG001") was active against Gram-positive aerobes (*S. aureus, enterococci, streptococci,* and *B. anthracis*) including resistant isolates, fastidious Gram-negative respiratory pathogens (*H. influenzae* and *M. catarrhalis*), *M. smegmatis,* and the evaluated Gram-negative anaerobes (*C. difficile* and *P. acnes*). The anti-infective peptide P1 (SEQ ID NO:1) was inactive against Gram-negative aerobes (*E. coli, K. pneumoniae,* and *P. aeruginosa*).

The anti-infective peptide P1 was provided as a dry powder and was stored −20° C. A stock solution was made at 2,560 μg/mL in water on the day of the assay. Once appropriate solvents were added to the comparator drugs, the stock solutions were allowed to stand for approximately 1 hr at room temperature to auto sterilize before aliquoting and freezing at −80° C. On the day of the assay, a fresh aliquot of frozen stock solutions of the comparator drugs at 40-fold the highest concentration in the test plates was removed from the −80° C., thawed, and was used for testing. The test organisms were previously acquired from the American Type Culture Collection (ATCC) and from clinical laboratories. Upon receipt, the isolates were streaked under suitable conditions onto agar medium appropriate for each organism. The plates containing anaerobic organisms were incubated anaerobically at 35° C. for 48 hours in a Bactron II Anaerobic Chamber (Sheldon Manufacturing Inc., Cornelius, OR). Aerobic organisms were incubated for 18-24 hours at 35° C. Colonies harvested from these growth plates were resuspended in the appropriate medium containing a cryoprotectant. Aliquots of each suspension were then frozen at −80° C. Prior to the assay, the organisms were thawed and sub-cultured on appropriate agar plates and incubated as described above.

The following Quality Control isolates were included as part of the tested isolates: *Clostridium difficile* ATCC 700057, *Escherichia coli* ATCC 25922, *Staphylococcus aureus* ATCC 29213, *Enterococcus faecalis* ATCC 29212, *Pseudomonas aeruginosa* ATCC 27853, and *Streptococcus pneumoniae* ATCC 49619. For anaerobic organisms, susceptibility testing was conducted in BBL Brucella broth (BRU; Becton Dickinson; Sparks, MD; Lot No. 2311123). BRU broth was supplemented with vitamin K1 (Sigma-Aldrich; St. Louis, MO; Lot No. MKBNS958V), hemin (Sigma-Aldrich; Lot No. SLBD8813V), and 5% laked horse blood (Cleveland Scientific; Bath, OH; Lot No. 222808). Agar plates for anaerobic organisms were Supplemented Brucella Agar plates (Remel, Lenexa, KS; Lot No. 484569).

For aerobic organisms, the medium employed for the MIC assay was Mueller-Hinton Broth (MHB II-Becton Dickinson; Lot No. 4293655) with the exception of *Haemophilus influenza,* which was tested in *Haemophilus* Test Medium (HTM; Teknova; Hollister, CA; Lot No. H580025K1401). MHB II was supplemented with 3% laked horse blood (Cleveland Scientific; Lot No. 222808) for *streptococci*. Agar plates used for aerobic organisms were trypticase soy agar plus 5% sheep blood (Remel; Lot No. 629110) with the exception of *H. influenzae* which was streaked onto Chocolate Agar (Becton Dickinson, Lot No. 4260888).

MIC assay plates were prepared using the CLSI broth microdilution procedure (see, e.g., Jorgensen, James H., and John D. Turnidge. "Susceptibility test methods: dilution and disk diffusion methods." Manual of Clinical Microbiology, Eleventh Edition. American Society of Microbiology, 2015. 1253-1273). Automated liquid handlers (Biomek 2000 and Biomek FX, Beckman Coulter, Fullerton CA) were used to conduct serial dilutions and liquid transfers. All wells in columns 2-12 of a standard 96-well microdilution plate (Costar 3795) were filled with 150 μL of the appropriate solvent. Three hundred μL of each test drug (at 40×) was added to each well in Column 1 of the plates. This plate was used to prepare the drug "mother plate" which provided the serial drug dilutions for the replicate "daughter plates". The Biomek 2000 was used to complete the serial transfers through Column 11 in the mother plates. The wells of Column 12 contained no drug, representing the organism growth control wells. The daughter plates were loaded with 185 μL per well of the test media described above using the Multidrop 384. The daughter plates were completed on the Biomek FX instrument which transferred 5 μL of drug solution from each well of a mother plate to each corresponding well of each daughter plate in a single step.

The anaerobe daughter plates containing media and drug were transferred to the Bactron II anaerobe chamber and allowed to reduce for 1 hour prior to inoculation. A standardized inoculum of each organism was prepared per CLSI methods (see, e.g., Jorgensen, James H., and John D. Turnidge. "Susceptibility test methods: dilution and disk diffusion methods." Manual of Clinical Microbiology, Eleventh Edition. American Society of Microbiology, 2015. 1253-1273). Suspensions were prepared to equal a 0.5 McFarland standard. The suspensions were additionally diluted in broth appropriate to the organism. The anaerobic plates were inoculated with 10 μL of standardized inoculum by hand from low to high drug concentration under anaerobic conditions, resulting in approximately $1 \times 10^5$ colony-forming-units/mL. The wells of the daughter plates ultimately contained 185 μL of broth, 5 μL of drug solution, and 10 µL of bacterial inoculum. For each assay, one extra plate of medium including the drug solutions (no inoculum) was prepared for the purpose of assessing solubility of the drug in the test medium. Anaerobe plates were stacked 3 high, covered with a lid on the top plate, placed in a BD GasPak EZ Anaerobe Container System and incubated at 35° C. for 46-48 hours.

The inocula for the aerobic organisms were dispensed into sterile reservoirs divided by width (Beckman Coulter) and the Biomek 2000 was used to inoculate the plates. Daughter plates were placed on the Biomek 2000 work surface reversed so that inoculation took place from low to high drug concentration. The Biomek 2000 delivered 10 µL of aerobic culture standardized inoculums into each well. These inoculations yielded a final cell concentration in the daughter plates of approximately $5 \times 10^5$ colony-forming-units/mL The wells of the daughter plates ultimately contained 185 µL of broth, 5 µL of drug solution, and 10 µL of bacterial inoculum. For each test medium, one extra plate including the drug solutions was prepared for the purpose of assessing solubility of the drug in the test medium (un-inoculated solubility control plate). Aerobe plates were stacked 3-4 high, covered with a lid on the top plate, placed in plastic bags, and incubated at 35° C. for approximately 20 hours, with the exception of *Mycobacterium smegmatis* which was incubated for 48 hours. The microplates were viewed from the bottom using a plate viewer, and the MIC was read and recorded as the lowest concentration of drug that inhibited visible growth of the organism. The un-inoculated solubility control plate was observed for evidence of drug precipitation.

6.2 Example 2

Anti-Infective Peptides

6.2.1 Analysis of Hemolysis Profile of Anti-Infective Peptides

The hemolytic activity of peptides against human erythrocyte cells was measured using a method adapted from Shai et al (Oren, Z.; Shai, Y. Biochemistry 1997, 36, 1826-1835). Fresh human red blood cells (hRBCs) were rinsed and washed thrice with phosphate-buffered saline (PBS), centrifuged for 10 min at 900 g, and the resultant packed blood cells were re-suspended in PBS to an erythrocyte concentration of 8.0% (v/v). An equal volume of peptide, resuspended in 10 mM phosphate buffer, was added to the hRBCs in order to achieve a final concentration of 4% (v/v) hRBC in a total volume of 100 µL and incubated for 1 hour at 37° C., with gentle agitation. After incubation, the samples were centrifuged at 1500 g for 5 minutes. Hemoglobin release was measured by absorbance measurements of the supernatant at 540 nm. Controls for 0% hemolysis and 100% hemolysis were obtained by suspending hRBC in PBS and 1% Triton X, respectively. The percentage of hemolysis was calculated according to the following equation: % Hemolysis= $[Abs_{pept} - Abs_{negative\ control}]/[Abs_{positive\ control} - Abs_{negative\ control}] \times 100$.

The minimum hemolytic concentration (MHC) was defined as the lowest concentration of peptide which is required to produce 10% hemolysis.

TABLE 12

Hemolysis data for anti-infective peptides TSG001-TSG009 (SEQ ID NOS: 1-9) and for the comparator peptides AH (SEQ ID NO: 10) and C5A (SEQ ID NO: 11). The anti-infective peptides are ranked according to the most preferred hemolysis profile (i.e., rank 1 is the most preferred peptide, with respect to the hemolysis profile, as it has the highest MHC value).

| Anti-infective peptide | MHC (µM) | Rank |
|---|---|---|
| TSG001 (SEQ ID. NO: 1) | 50 | 1 |
| TSG002 (SEQ ID. NO: 2) | 50 | 2 |
| TSG003 (SEQ ID. NO: 3) | 50 | 3 |
| TSG004 (SEQ ID. NO: 4) | 50 | 4 |
| TSG005 (SEQ ID. NO: 5) | 13 | 5 |
| TSG006 (SEQ ID. NO: 6) | 3 | 6 |
| TSG007 (SEQ ID. NO: 7) | 1.5 | 7 |
| TSG008 (SEQ ID. NO: 8) | 1.5 | 8 |
| TSG009 (SEQ ID. NO: 9) | 1.5 | 9 |
| Comparator Peptide | MHC (µM) | Rank |
| AH (SEQ ID NO: 10) | 50 | N/A |
| C5A (SEQ ID NO: 11) | 13 | N/A |

The data presented in Table 12 indicate that the anti-infective peptides TSG001-TSG005 (SEQ ID NO:1-5) have good hemolytic activity profiles.

6.2.2 Analysis of Antiviral Activity of Anti-Infective Peptides (a) Materials and Methods Antiviral activity of the peptide against the tested virus was tested in a cell-based inhibition assay of cytopathic effect (CPE) in Vero cells caused by the viruses. Cells were seeded at 10,000 cells per well in 96-well plates and incubated overnight. The peptides were serially diluted 2-fold in serum-free MEM and the viruses were prepared for a final multiplicity of infection (MOI) of 0.1. The peptide dilutions were incubated with the virus for one hour at 37° C. before infecting the cells. MEM supplemented with 2% FBS (and Pen/Strep and L-gln) was added for a final FBS concentration of 1%. After 5 days the cells were fixed and stained with 0.1% crystal violet in 5% glutaraldehyde solution. Optical density was determined at 540 nm and used to calculate the 50% efficacy concentration (EC50) using untreated, infected cells as 0% efficacy and uninfected cells as 100% efficacy (XLfit 5.4; equation 205).

For DENV, DENV (DENV-1 (PRS41393), DENV-2 (New Guinea C), DENV-3 (H87), or DENV-4 (H241)) was sequentially passed between insect (C6/36; ATCC #CRL-1660) and Vero cells; DENY used for the experiments was derived from C6/36 cells grown at 33° C.

JEV (14-14-2), CHIKV (181/25), and YFV (17D) used for the experiments were grown at 37° C. in Vero cells.

(b) Results

The anti-infective peptides TSG001, TSG002, TSG003, TSG004, and TSG006 displayed anti-infective activity against DENV-1, DENV-2, DENV-3, DENV-4, CHIKV, and YFV infection (see Tables 13-19, below). TSG001, TSG002, TSG004, and TSG006 displayed anti-infective activity against JEV (see, Table 19, below).

TABLE 13

Antiviral activity of anti-infective peptides TSG001, TSG002, TSG003, TSG004, and TSG006 and comparator peptides AH (SEQ ID NO: 10) and C5A (SEQ ID NO: 11) against DENV-1. The anti-infective peptides are ranked according to the most preferred anti-DENV-1 activity (i.e., rank 1 is the most preferred peptide, with respect to the anti-DENV-1 activity, as it has the lowest EC50 value).

| Anti-infective peptide | EC50 (µM) | Rank |
|---|---|---|
| TSG006 (SEQ ID NO: 6) | 1.45 | 1 |
| TSG002 (SEQ ID NO: 2) | 1.55 | 2 |
| TSG001 (SEQ ID NO: 1) | 2.04 | 3 |
| TSG003 (SEQ ID NO: 3) | 3.37 | 4 |
| TSG004 (SEQ ID NO: 4) | 8.51 | 5 |
| Comparative Peptide | EC50 (µM) | Rank |
| C5A (SEQ ID NO: 11) | 0.65 | N/A |
| AH (SEQ ID NO: 10) | 2.55 | N/A |

TABLE 14

Antiviral activity of anti-infective peptides TSG001, TSG002, TSG003, TSG004, and TSG006 and comparator peptides AH (SEQ ID NO: 10) and C5A (SEQ ID NO: 11) against DENV-2. The anti-infective peptides are ranked according to the most preferred anti-DENV-2 activity (i.e., rank 1 is the most preferred peptide, with respect to the anti-DENV-1 activity, as it has the lowest EC50 value).

| Anti-infective peptide | EC50 (µM) | Rank |
|---|---|---|
| TSG006 (SEQ ID NO: 6) | 0.67 | 1 |
| TSG002 (SEQ ID NO: 2) | 1.68 | 2 |
| TSG003 (SEQ ID NO: 3) | 1.73 | 3 |
| TSG001 (SEQ ID NO: 1) | 1.95 | 4 |
| TSG004 (SEQ ID NO: 4) | 6.26 | 5 |
| Comparative Peptide | EC50 (µM) | Rank |
| AH (SEQ ID NO: 10) | 0.18 | N/A |
| C5A (SEQ ID NO: 11) | 0.34 | N/A |

TABLE 15

Antiviral activity of anti-infective peptides TSG001, TSG002, TSG003, TSG004, and TSG006 and comparator peptides AH (SEQ ID NO: 10) and C5A (SEQ ID NO: 11) against DENV-3. The anti-infective peptides are ranked according to the most preferred anti-DENV-3 activity (i.e., rank 1 is the most preferred peptide, with respect to the anti-DENV-3 activity, as it has the lowest EC50 value).

| Anti-infective peptide | EC50 (µM) | Rank |
|---|---|---|
| TSG006 (SEQ ID NO: 6) | 1.49 | 1 |
| TSG003 (SEQ ID NO: 3) | 1.73 | 2 |
| TSG001 (SEQ ID NO: 1) | 1.90 | 3 |
| TSG002 (SEQ ID NO: 2) | 2.65 | 4 |
| TSG004 (SEQ ID NO: 4) | 6.14 | 5 |
| Comparator Peptide | EC50 (µM) | Rank |
| C5A (SEQ ID NO: 11) | 1.93 | N/A |
| AH (SEQ ID NO: 10) | 7.22 | N/A |

TABLE 16

Antiviral activity of anti-infective peptides TSG001, TSG002, TSG003, TSG004, and TSG006 and comparator peptides AH (SEQ ID NO: 10) and C5A (SEQ ID NO: 11) against DENV-4. The anti-infective peptides are ranked according to the most preferred anti-DENV-4 activity (i.e., rank 1 is the most preferred peptide, with respect to the anti-DENV-4 activity, as it has the lowest EC50 value).

| Anti-infective peptide | EC50 (µM) | Rank |
|---|---|---|
| TSG006 (SEQ ID NO: 6) | 1.50 | 1 |
| TSG001 (SEQ ID NO: 1) | 1.64 | 2 |
| TSG002 (SEQ ID NO: 2) | 1.88 | 3 |
| TSG003 (SEQ ID NO: 3) | 1.91 | 4 |
| TSG004 (SEQ ID NO: 4) | 7.21 | 5 |
| Comparator Peptide | EC50 (µM) | Rank |
| C5A (SEQ ID NO: 11) | 1.31 | N/A |
| AH (SEQ ID NO: 10) | 3.46 | N/A |

TABLE 17

Antiviral activity of anti-infective peptides TSG001, TSG002, TSG003, TSG004, and TSG006 and comparator peptides AH (SEQ ID NO: 10) and C5A (SEQ ID NO: 11) against CHIKV. The anti-infective peptides are ranked according to the most preferred anti-CHIKV activity (i.e., rank 1 is the most preferred peptide, with respect to the anti-CHIKV activity, as it has the lowest EC50 value).

| Anti-infective peptide | EC50 (µM) | Rank |
|---|---|---|
| TSG003 (SEQ ID NO: 3) | 2.18 | 1 |
| TSG001 (SEQ ID NO: 1) | 2.52 | 2 |
| TSG002 (SEQ ID NO: 2) | 3.41 | 3 |
| TSG006 (SEQ ID NO: 6) | 3.44 | 4 |
| TSG004 (SEQ ID NO: 4) | 7.69 | 5 |
| Comparator Peptide | EC50 (µM) | Rank |
| C5A (SEQ ID NO: 11) | 3.09 | N/A |
| AH (SEQ ID NO: 10) | 6.01 | N/A |

TABLE 18

Antiviral activity of anti-infective peptides TSG001, TSG002, TSG003, TSG004, and TSG006 and comparator peptides AH (SEQ ID NO: 10) and C5A (SEQ ID NO: 11) against YFV. The anti-infective peptides are ranked according to the most preferred anti-YFV activity (i.e., rank 1 is the most preferred peptide, with respect to the anti-YFV activity, as it has the lowest EC50 value).

| Anti-infective peptide | EC50 (µM) | Rank |
|---|---|---|
| TSG006 (SEQ ID NO: 6) | 0.79 | 1 |
| TSG001 (SEQ ID NO: 1) | 1.53 | 2 |
| TSG003 (SEQ ID NO: 3) | 2.14 | 3 |
| TSG002 (SEQ ID NO: 2) | 2.18 | 4 |
| TSG004 (SEQ ID NO: 4) | 7.99 | 5 |
| Comparator Peptide | EC50 (µM) | Rank |
| C5A (SEQ ID NO: 11) | 0.29 | N/A |
| AH (SEQ ID NO: 10) | 21.72 | N/A |

TABLE 19

Antiviral activity of anti-infective peptides TSG001, TSG002, TSG003,T SG004, and TSG006 and comparator peptides AH (SEQ ID NO: 10) and C5A (SEQ ID NO: 11) against JEV. The anti-infective peptides are ranked according to the most preferred anti-JEV activity (i.e., rank 1 is the most preferred peptide, with respect tothe anti-JEV activity, as it has the lowest EC50 value).

| Anti-infective peptide | EC50 (µM) | Rank |
|---|---|---|
| TSG006 (SEQ ID NO: 6) | 1.63 | 1 |
| TSG001 (SEQ ID NO: 1) | 2.01 | 2 |
| TSG002 (SEQ ID NO: 2) | 2.40 | 3 |
| TSG004 (SEQ ID NO: 4) | 4.68 | 4 |
| TSG003 (SEQ ID NO: 3) | >18.75 | 5 |

| Comparator Peptide | EC50 (µM) | Rank |
|---|---|---|
| C5A (SEQ ID NO: 11) | 0.47 | N/A |
| AH (SEQ ID NO: 10) | 0.54 | N/A |

6.2.3 Analysis of Cytotoxicity Profile of Anti-Infective Peptides

Cytotoxic effects of the peptides were determined in Vero cells using the CellTiter-Glo kit (Promega #G7570). Serial dilutions of the peptide were prepared in MEM (supplemented with 1% FBS, 1× Penicillin/Streptomycin, 1× L-gln). 1×10$^4$ Vero cells (ATCC #CCL-81) seeded in black-walled 96-well plates were incubated with the dilutions for one hour at two-times the final concentration in serum-free MEM. Supplemented MEM was then added to final concentration and the cells were incubated for 3, 6, and 9 days, respectively. Cell survival was determined by luciferase activity as described in the manufacturer's protocol.

TABLE 20

Cytotoxicity data for anti-infective peptides TSG001, TSG002, TSG003, TSG004, and TSG006 and comparator peptides AH (SEQ ID NO: 10) and C5A (SEQ ID NO: 11) in Vero cells. The anti-infective peptides are ranked according to the most preferred cytotoxicity profile (i.e., rank 1 is the most preferred peptide, with respect to cytotoxicity, as it has the highest CC50 value).

| Anti-infective peptide | CC50 (µM) | Rank |
|---|---|---|
| TSG001 (SEQ ID NO: 1) | 153.39 | 1 |
| TSG004 (SEQ ID NO: 4) | 114.48 | 2 |
| TSG003 (SEQ ID NO: 3) | 38.63 | 3 |
| TSG006 (SEQ ID NO: 6) | 17.45 | 4 |
| TSG002 (SEQ ID NO: 2) | 16.13 | 5 |

| Comparator Peptide | EC50 (µM) | Rank |
|---|---|---|
| AH (SEQ ID NO: 10) | 127.46 | N/A |
| C5A (SEQ ID NO: 11) | 28.99 | N/A |

The data presented in Table 20 indicate that the anti-infective peptides TSG001, TSG003, and TSG004 have good cytotoxicity profiles.

6.2.4 Analysis of the Therapeutic Index of Anti-Infective Peptides

The therapeutic index of each peptide was determined for each virus strain based on the CC50/EC50 ratio. The average therapeutic index was computed across the panel of seven virus strains in order to rank the peptides. In all cases, TSG001 (SEQ ID NO:1) had the best therapeutic index.

TABLE 21

Therapeutic indices for anti-infective peptides TSG001, TSG002, TSG003, TSG004, and TSG006 and comparator peptides AH (SEQ ID NO: 10) and C5A (SEQ ID NO: 11) for the indicated viruses.

| Anti-infective peptide | Therapeutic Index | | | | | | |
|---|---|---|---|---|---|---|---|
| | DENV-1 | DENV-2 | DENV-3 | DENV-4 | CHIKV | YFV | JEV |
| TSG001 (SEQ ID NO: 1) | 75.19 | 78.66 | 80.73 | 93.53 | 60.87 | 100.25 | 76.31 |
| TSG002 (SEQ ID NO: 2) | 10.41 | 9.60 | 6.09 | 8.58 | 4.73 | 7.40 | 6.72 |
| TSG003 (SEQ ID NO: 3) | 11.46 | 22.33 | 22.33 | 20.23 | 17.72 | 18.05 | NA |
| TSG004 (SEQ ID NO: 4) | 13.45 | 18.29 | 18.64 | 15.88 | 14.89 | 14.33 | 24.46 |
| TSG006 (SEQ ID NO: 6) | 12.03 | 26.04 | 11.71 | 11.63 | 5.07 | 22.09 | 10.71 |
| AH (SEQ ID NO: 10) | 49.98 | 708.11 | 17.65 | 36.84 | 21.21 | 5.87 | 236.04 |
| C5A (SEQ ID NO: 11) | 44.60 | 85.26 | 15.02 | 22.13 | 9.38 | 99.97 | 61.68 |

TABLE 22

Average therapeutic indices for anti-infective peptides TSG001, TSG002, TSG003, TSG004, and TSG006 and comparator peptides AH (SEQ ID NO: 10) and C5A (SEQ ID NO: 11). The anti-infective peptides are ranked according to the most preferred therapeutic index (i.e., rank 1 is the most preferred peptide, with respect to therapeutic index, as it has the highest therapeutic index).

| Anti-infective peptide | Average Therapeutic Index | Rank |
|---|---|---|
| TSG001 (SEQ ID NO: 1) | 80.79 | 1 |
| TSG004 (SEQ ID NO: 4) | 17.13 | 2 |
| TSG003 (SEQ ID NO: 3) | 16.31 | 3 |

TABLE 22-continued

Average therapeutic indices for anti-infective peptides TSG001, TSG002, TSG003, TSG004, and TSG006 and comparator peptides AH (SEQ ID NO: 10) and C5A (SEQ ID NO: 11). The anti-infective peptides are ranked according to the most preferred therapeutic index (i.e., rank 1 is the most preferred peptide, with respect to therapeutic index, as it has the highest therapeutic index).

|  | Average Therapeutic Index | Rank |
| --- | --- | --- |
| TSG006 (SEQ ID NO: 6) | 14.18 | 4 |
| TSG002 (SEQ ID NO: 2) | 7.65 | 5 |
| Comparator Peptide |  |  |
| AH (SEQ ID NO: 10) | 153.67* | N/A |
| C5A (SEQ ID NO: 11) | 48.29 | N/A |

*There is great variability in AH peptide's therapeutic index across different flaviviruses. By contrast, TSG001 (SEQ ID NO: 1) is much more reliable, with stable activity across all the tested flaviviruses.

The data presented in Table 21 and 22 indicate that the anti-infective peptides TSG001, TSG002, TSG003, TSG004, and TSG006 have good therapeutic profiles.

6.2.5 Peptide Modifications

Using identical methods to those described above (see Section 6.2.3(a)), the antiviral activity of pegylated versions of TSG001 and TSG002 (labeled TSGX1X and TSGX2X, respectively) against the same virus panel were evaluated.

```
TSGX1X is
                     (pegylated TSG001 (SEQ ID NO: 1))
NH2-PEG12-Amide-PEG12-SGSWLRDVWTWLQSKL-NH2.

TSGX2X is
                                        (SEQ ID NO: 2)
NH2-PEG12-Amide-PEG12-GSSWLRDVWTWLQSKL (pegylated TSG002 (SEQ ID NO: 2))
NH2.
```

Two PEG12 building blocks [Fmoc-PEG12-OH] were sequentially attached at the N-termini using conventional solid-phase peptide synthesis. The molecular mass of the peptides are 3160.7 Da each, of which the PEG chain is 1217.44 Da.

The EC50 values are reported below in Table 23 and demonstrate that TSG00X1X and TSG00X2X preserve strong antiviral activity against DENV and JEV strains, while antiviral activities against CHKV and YFV are reduced.

TABLE 23

EC50 values for anti-infective peptides.

| Compound | EC50 (μM) for the Indicated Virus | | | | | | |
| --- | --- | --- | --- | --- | --- | --- | --- |
|  | DENV-1 | DENV-2 | DENV-3 | DENV-4 | CHKV | YFV | JEV |
| TSG001 (SEQ ID NO: 1) | 2.04 | 1.95 | 1.90 | 1.64 | 2.52 | 1.53 | 2.01 |
| TSGX1X | 4.98 | 3.86 | 2.28 | 3.54 | 31.50 | 22.44 | 0.64 |
| TSG002 (SEQ ID NO: 2) | 1.55 | 1.68 | 2.65 | 1.88 | 3.41 | 2.18 | 2.40 |
| TSGX2X | 7.08 | 6.44 | 2.82 | 4.99 | 31.96 | 11.67 | 1.10 |

6.2.6 Antiviral Activity Against Filoviruses

Ebola virus (EBOV) and Marburg virus (MARV) are Category A bio-warfare agents under the Center for Disease Control's classification system. The fear remains that these viruses could be isolated and cultivated for bioterrorism purposes. The antiviral activity of pegylated and non-pegylated versions of TSG001 and TSG002 were tested against these two viruses. In particular, Vero E6 cells were plated in 96-well plates at a density of 40,000 cells/well. The test agents were incubated with virus for one hour (final MOI=0.1-0.5) at 37° C. The virus and compound mixture was transferred to the cells, and placed in an incubator for 48 hours. Then, the infected cells were fixed in 10% buffered formalin and cell-based ELISA assay was performed in order to determine the percent of viral inhibition using the Pierce Super Signal ELISA pico chemiluminescent substrate kit (Thermo Scientific, Rockford, Il). The cells were washed thrice with PBS, and blocked for 1 hour. Then, a diluted primary antibody in block was added for 2 hours, and cells were again washed thrice with PBS. Next, a diluted secondary antibody (HRP-conjugated goat anti-mouse) in block was added for 1 hour. The amount of virus was measured by reading the luminescence on a conventional plate reader.

The EC50 values are reported below in Table 24 and demonstrate that the non-pegylated peptides have potent antiviral activity.

TABLE 24

Antiviral activity of Anti-Infective Peptides Against Filoviruses

| Compound | EC50 Values for the Indicated Virus | |
| --- | --- | --- |
|  | EBOV | MARV |
| TSG001 (SEQ ID NO: 1) | 0.934 | 0.637 |
| TSGX1X | 13.45 | 14.35 |
| TSG002 (SEQ ID NO: 2) | 1.015 | 0.922 |
| TSGX2X | 29.91 | 44.34 |

6.3 Example 3

Inhibitory Effect of Pegylated Anti-Infective Peptides Against Multiple Viruses This example describes the antiviral activity of two anti-infective peptides using a cytopathic effect (CPE)-based EC50 assay for the following viruses: YFV 17D, VACV NYCBH, VEEV TC-83, LACV H44-71017, RVFV MP12, DENV serotypes 1 to 4, JEV 14-14-2, Influenza A/California/07/2009 virus (H1N1), and CHIKV 181/25.

To perform the CPE-based EC50 assay, cells were seeded in 96-well plates and incubated overnight. The next day, serial dilutions of the test articles were prepared in medium. Two conditions were evaluated: (1) preincubation of the virus with peptide dilutions (TSGX1X and TSGX2X); and (2) addition of the peptide dilutions immediately after infection (TSGX1X only). TSGX1X refers to NH2-PEG12-Amide-PEG12-SGSWLRDVWTWLQSKL-COOH (pegylated TSG001 (SEQ ID NO:1)). TSGX2X refers to NH2-

PEG12-Amide-PEG12-GSSWLRDVWTWLQSKL-COOH (pegylated TSG002 (SEQ ID NO:2)). For the preincubation condition: (i) anti-infective peptide dilutions were prepared in medium and incubated with virus for one hour at 37° C. (35° C. for influenza virus); (ii) control inhibitors and medium only were incubated in parallel; and (iii) cells were infected with the preincubation mixes and incubated for a virus-specific time. For the no preincubation condition: (i) cells were infected with the viruses for one hour; (ii) peptide dilutions were prepared in medium and added to the infected cells; (iii) control inhibitors and medium only were incubated in parallel: and (iv) cells were incubated for the virus-specific time at 37° C. (35° C. for MDCK cells). After incubation, cells were then fixed and stained with a crystal violet/glutaric dialdehyde solution. The optical density was determined and the EC50 was calculated using the uninfected (cells only) control as 0% CPE and the controls without compound (virus only) as 100% CPE using a 4-PL curve fit of the OD.

To perform the cytotoxicity assay (CC50), cells were seeded in black-walled 96-well plates and incubated overnight. The next day, serial dilutions of the anti-infective peptides were prepared. The growth medium was aspirated form the cells and the compound dilutions were added. Cells incubated with medium only served as controls. After 3, 6, and 8 (day 7 for MDCK) days, the medium was aspirated (one set of plates per day), and the cells were lysed for evaluation of the ATP content using Promega's CelltiterGlo kit. The resulting luciferase luminescence was quantified and used to calculate the CC50 using a 4-PL curve fit. Not all of the incubation times were evaluated for cytotoxicity. Tables 25 and 26 provide a summary of the days on which cytotoxicity was evaluated. The CC50 data is presented in Table 27. Table 28 provides a summary of the efficacy of each peptide against each virus in the pre-incubation condition. Table 29 provides a summary of the efficacy of each peptide against each virus in the pre-incubation condition.

TABLE 25

Timepoints for incubation and cytotoxicity.

| Incubation Time | Cytotoxicity Day |
|---|---|
| 3, 4 | 3 |
| 5, 6, 7 | 6 |
| 8+ | 8 |

TABLE 26

Incubation times (days) and the corresponding days on which cytotoxicity were determined.

| | Incubation time | Cytotoxicity day |
|---|---|---|
| CHIKV 181/25 | 3 | 3 |
| DENV-1 PRS41393 | 5 | 6 |
| DENV-2 New Guinea C | 5 | 6 |
| DENV-3 H87 | 5 | 6 |
| DENV-4 H241 | 5 | 6 |
| JEV 14-14-2 | 10 | 8 |
| IVF A/CA/07/09 | 5 | 7 |
| LACV H44-71017 | 4 | 3 |
| RVFV MP12 | 4 | 3 |
| VACV NYCBH | 4 | 3 |
| VEEV TC-83 | 3 | 3 |
| YFV 17D | 6 | 6 |

TABLE 27

Cytotoxicity of each peptide tested at various time points and in the indicated cell line. Values are of CC50 (µM).

| | Day 3 Vero | Day 6 Vero | Day 8 Vero | Day 7 MDCK |
|---|---|---|---|---|
| TSGX1X | 20.88 | 21.17 | 37.43 | >200 |
| TSGX2X | 29.28 | 37.87 | 60.74 | >75 |
| Cidofovir | >375 | N/D | N/D | N/D |
| 6-azauridine | 3.83 | N/D | N/D | N/D |
| VEEV inhibitor | >50 | N/D | N/D | N/D |
| Ribavirin | 576.6 | >750 | >750 | N/D |
| Zanamivir | N/D | N/D | N/D | >375 |

TABLE 28

Summary of the efficacy of each peptide against each virus in the pre-incubation condition. The values presented are EC50 (µM).

| | TSGX1X | TSGX2X | 6-azauridine | Cidofovir | Ribavirin | VEEV inhibitor | Zanamivir |
|---|---|---|---|---|---|---|---|
| CHIKV 181/25 | 31.50 | 31.96 | 0.4 | N/D | N/D | N/D | N/D |
| DENV-1 PRS41393 | 4.98 | 7.08 | N/D | N/D | 89.12 | N/D | N/D |
| DENV-2 New Guinea C | 3.86 | 6.44 | N/D | N/D | 203.42 | N/D | N/D |
| DENV-3 H87 | 2.28 | 2.82 | N/D | N/D | 93.93 | N/D | N/D |
| DENV-4 H241 | 3.54 | 4.99 | N/D | N/D | 209.11 | N/D | N/D |
| IVF A/CA/07/09 | >75 | >75 | N/D | N/D | N/D | N/D | 2.81 |
| JEV 14-14-2 | 0.64 | 1.10 | N/D | N/D | 33.89 | N/D | N/D |
| LACV H44-71017 | >75 | >75 | N/D | N/D | 120.30 | N/D | N/D |

TABLE 28-continued

Summary of the efficacy of each peptide against each virus in the
pre-incubation condition. The values presented are EC50 (μM).

|  | TSGX1X | TSGX2X | 6-azauridine | Cidofovir | Ribavirin | VEEV inhibitor | Zanamivir |
|---|---|---|---|---|---|---|---|
| RVFV MP12 | 24.65 | 25.35 | N/D | N/D | 57.79 | N/D | N/D |
| VACV NYCBH | 0.41 | 18.80 | N/D | 142.4 | N/D | N/D | N/D |
| VEEV TC-83 | >75 | >75 | N/D | N/D | N/D | 18.60 | N/D |
| YFV 17D | 22.44 | 11.67 | N/D | N/D | 212.06 | N/D | N/D |

N/D = not done.

Taken together, the TSGX1X and TSGX2X are effective against infection with CHIKV, DENV, JEV, RVFV, VACV, and YFV.

TABLE 29

Summary of the efficacy of each peptide against each virus in the
no pre-incubation condition. The values presented are EC50 (μM).

|  | TSGX1X | TSGX2X | 6-azauridine | Cidofovir | Ribavirin | VEEV inhibitor | Zanamivir |
|---|---|---|---|---|---|---|---|
| CHIKV 181/25 | 27.25 | N/D | 21.54 | N/D | N/D | N/D | N/D |
| DENV-1 PRS41393 | 10.45 | N/D | N/D | N/D | 150.13 | N/D | N/D |
| DENV-2 New Guinea C | 9.52 | N/D | N/D | N/D | 185.47 | N/D | N/D |
| DENV-3 H87 | 5.08 | N/D | N/D | N/D | 165.21 | N/D | N/D |
| DENV-4 H241 | 12.01 | N/D | N/D | N/D | 283.97 | N/D | N/D |
| IFV A/CA/07/09 | >75 | N/D | N/D | N/D | N/D | N/D | 121.64 |
| JEV 14-14-2 | 1.27 | N/D | N/D | N/D | 38.44 | N/D | N/D |
| LACV H44-71017 | >75 | N/D | N/D | N/D | 284.99 | N/D | N/D |
| RVFV MP12 | >75 | N/D | N/D | N/D | 166.81 | N/D | N/D |
| VACV NYCBH | 6.30 | N/D | N/D | 49.88 | N/D | N/D | N/D |
| VEEV TC-83 | >75 | N/D | N/D | N/D | N/D | 28.88 | N/D |
| YFV 17D | >75 | N/D | N/D | N/D | 170.02 | N/D | N/D |

N/D = not done.

Taken together, the TSGX1X is effective against infection with CHIKV, DENV, JEV, RVFV, VACV, and YFV.

6.4 Example 4

Determination of Antiviral Activity of Test Article TSG001 Against HSV-1 and Influenza A Virus (H1N1 & H3N2)

This example describes the antiviral activity of anti-infective peptide TSG001 (SEQ ID NO:1) in a CPE assay against the following viruses: HSV-1, influenza A/Hong Kong/1/1968 virus (H3N2), influenza A/California/07/2009 virus (H1N1), and describes the cytotoxicity of the peptide in Vero cells on day 3 and in MDCK cells on day 6 of incubation.

To perform the CPE-based EC50 assay, cells were seeded in 96-well plates and incubated overnight. The next day, serial dilutions of the test article were prepared in medium and incubated with virus for one hour at 37° C. (HSV-1) or 35° C. (H3N2 and H1N1). Control inhibitors and medium only were incubated in parallel. Vero cells were infected with the preincubation mixes and incubated for a virus-specific time (HSV-1: 3 days: H3N2 and H1N1: 6 days). After incubation, cells were then fixed and stained with a crystal violate/glutaric dialdehyde solution. The optical density was determined and the EC50 was calculated using the uninfected (cells only) control as 0% CPE and the controls without compound (virus only) as 100% CPE using a 4-PL curve to fit the OD.

To perform the cytotoxicity assay, cells were seeded in black-walled 96-well plates and incubated overnight. The next day, serial dilutions of the test article were prepared. The growth medium was aspirated from the cells and the compound dilutions were added. Cells that were incubated with medium only served as controls. After 3 days (Vero) and 7 days (MDCK) the medium was aspirated and cells were lysed for evaluation of the ATP content using Promega's CelltiterGlo kit. The resulting luciferase luminescence was quantified and used to calculate the CC50 using a 4-PL curve fit.

The results are presented in Table 30, below. The starting concentration utilized for each virus for the EC50 and CC50 was 200 µM. Anti-infective peptide TSG001 (SEQ ID NO:1) had a high EC50 for HSV-1 and influenza A virus infection.

TABLE 30

Efficacy and cytotoxicity data for anti-infective peptide TSG001 (SEQ ID NO: 1) against HSV-1 and influenza A viruses.

|  | TSG001 (SEQ ID NO: 1) | | Acyclovir | | Zanamivir | |
| --- | --- | --- | --- | --- | --- | --- |
|  | EC50 (µM) | CC50 (µM) | EC50 (µM) | CC50 (µM) | EC50 (µM) | CC50 (µM) |
| HSV-1 (Vero cells) | >200 | >200 | 2.819 | >100 | N/D | N/D |
| H3N2 (MDCK cells) | >200 | >200 | N/D | N/D | 4.516 | >100 |
| H1N1 (MDCK cells) | >200 | >200 | N/D | N/D | N/D | N/d |

ND = not determined

6.5 Example 5

Antiviral Activity of Anti-Infective Peptides Against ZIKV 6.5.1 Antiviral Activity of Anti-Infective Peptides Against ZIKV Determined by Plaque-Reduction Neutralization Assay at Day 4

This example describes the antiviral activity of two anti-infective peptides, in a plaque-reduction neutralization assay against ZIKV. This example also describes the cytotoxicity of the peptides in Vero cells on day 4.

Vero cells were seeded at 1×10$^5$ cells per well in 24-well plates and incubated overnight. The next day 11 two-fold serial dilutions of the peptide were prepared starting at 20 µM. ZIKV FSS 13025 was diluted to ~150 PFU. Peptide dilutions were incubated with virus for 1 h at 37° C.

Cells were infected with the peptide-virus mixtures for 1 hour at 37° C. The inoculum was removed and 2 mL 0.8% (w/v) methylcellulose (Fisher Scientific) in medium supplemented with 1% FBS was added. After 4 days, plates were fixed and analyzed for plaques by crystal violet staining. Briefly, cells were fixed with fixing solution (5% glutaric dialdehyde (Sigma Aldrich) in DPBS) followed by staining with 0.1% crystal violet (Sigma Aldrich) in fixing solution. The IC$_{50}$ was calculated based on the number of plaques relative to the virus-only sample using a 4-PL curve fit.

Each of the tested anti-infective peptides displayed anti-ZIKV activity and good cytotoxicity in the tested cells, especially the L-isomer (Table 31).

TABLE 31

IC50 and CC50 data for anti-infective peptides TSG001 (SEQ ID NO: 1) L- and D-isomer versions against ZIKV.

| Anti-Infective Peptide | IC50 (µM) | CC50 (µM) |
| --- | --- | --- |
| TSG001 L-isomer (SEQ ID NO: 1) | 1.01 | >20 |
| TSG001 D-isomer (SEQ ID NO: 1) | 0.49 | 11.65 |

6.5.2 Antiviral Activity of Anti-Infective Peptides Against ZIKV Determined by Yield Reduction Assay at Day 3

The yield reduction neutralization assay was performed by seeding Vero cells in 24-well plates and incubating them overnight. The next day, 6 two-fold serial dilutions of the anti-infective peptides were prepared starting at 20 µM. ZIKV FSS 13025 was diluted to ~150 plaque forming units (PFU). The test dilutions were incubated with virus for 1 hour at 37° C. Cells were infected for 1 hour after the inoculums was removed. Fresh medium was added and cells were incubated at 37° C. for 3 days. Supernatants were harvested, cleared of cell debris, and stored at −80° C.

To determine viral titers, cells were infected with the mix for 1 hour at 37° C. The inoculums were removed and 0.8% methylcellulose was added. After 4 days, plates were analyzed for plaques. The IC50 was calculated based on the number of plaques relative to the virus-only using a 4-PL curve fit.

Each of the tested anti-infective peptides displayed anti-ZIKV activity and good cytotoxicity in the tested cells, especially the L-isomer (Table 32).

TABLE 32

IC50 and CC50 data for anti-infective peptides TSG001 (SEQ ID NO: 1) L- and D-isomer versions against ZIKV.

|  | IC50 (µM) | CC50 (µM) |
| --- | --- | --- |
| TSG001 L-isomer (SEQ ID NO: 1) | 1.148 | >20 |
| TSG001 D-isomer (SEQ ID NO: 1) | 0.646 | 11.65 |

6.5.3 Anti-ZIKV Activity of Anti-Infective Peptide TSG001 (SEQ ID NO:1)

The Zika virus (ZIKV) epidemic is a global public health emergency, and there are no currently approved therapies. A membrane curvature-sensing peptide was designed that potently abrogates ZIKV infectivity Inhibitory concentrations did not affect the viability of mammalian or bacterial cell lines of importance to human health. These results suggest that viral envelope targeting is an effective antiviral strategy against ZIKV, and could be utilized in prophylactic and therapeutic applications.

A newly designed, short amphipathic peptide that possesses potent antiviral activity against ZIKV based on viral envelope targeting is described in this example. Inspired by longer, viral-encoded amino acid sequences that confer membrane curvature sensing properties (Cho et al., ACS Chemical Biology 4, 1061 (2009); Jackman et al., Small 11, 2372 (2015); Jackman et al., Journal of the American Chemical Society, (2016)), the putative sequence designed here (P1: SGSWLRDVWTWLQSKL (SEQ ID NO:1)) has only 16 amino acids, and is appreciably shorter than the clinically approved, 37 amino acid long HIV entry inhibitor T-20/enfuvirtide (Lalezari et al., New England Journal of Medicine 348, 2175 (2003)) (FIG. 1A). Circular dichroism spectroscopy experiments demonstrated that the membrane-bound peptide undergoes significant helical induction (27% increase), folding into a more active, α-helical state (83% helicity) in zwitterionic lipid vesicles (FIG. 1B). Fluorescence spectroscopy experiments indicated strong partitioning of the tryptophan-containing peptide into zwitterionic lipid bilayers, with a lipid-water partition coefficient on the order of 10$^5$ for high-curvature vesicles below 200 nm diameter (Melo et al., Nature Reviews Microbiology 7, 245 (2009)), and hence the binding-folding equilibrium within this regime favors the active, bound state (Krauson et al., Journal of the American Chemical Society 137, 16144 (2015)) (FIG. 1C). On the other hand, the peptide exhibits negligible partitioning into larger vesicles, indicating that the peptide behaves as a membrane curvature sensor and is preferentially active against highly curved membranes such as small, enveloped viruses. Importantly, a functional screen of the peptide's antiviral potency against a panel of mosquito-borne, enveloped viruses in a cytopathic effect assay revealed strong inhibition. Peptide concentrations yielding 50% inhibition of cytopathic effect (EC50) were less than 3 µM against all four serotypes of Dengue virus as well as Japanese encephalitis, Yellow Fever and Chikungunya viruses (Table 33). Collectively, the peptide's wide spectrum of inhibitory activity against enveloped viruses and its membrane curvature-selectivity provided motivation to evaluate its antiviral activity against ZIKV as well as the corresponding mechanism of action.

TABLE 33

Antiviral activity of anti-infective peptide TSG001 (SEQ ID NO: 1)

| Virus | EC50 (µM) |
| --- | --- |
| Dengue-1 PRS41393 | 2.04 |
| Dengue-2 New Guinea C | 1.95 |
| Dengue-3 H87 | 1.90 |
| Dengue-4 H241 | 1.64 |
| Yellow Fever 17D | 1.53 |
| Japanese Encephalitis SA 14-14-2 | 2.01 |
| Chikungunya 181/25 | 2.52 |

Antiviral tests were conducted using the ZIKV strain FSS13025, which belongs to the Asian lineage and was isolated from a pediatric patient from the 2010 outbreak in Cambodia (Haddow et al., PLoS Negl Trop Dis 6, e1477 (2012)). A plaque reduction assay (PRNT) was conducted in order to determine the neutralizing activity of the peptide against ZIKV infection in Vero cells, which are derived from African green monkey kidney cells. The peptide (TSG001, SEQ ID NO:1) was strongly inhibitory against ZIKV with concentration-dependent behavior, and the 50% plaque reduction neutralization titer (PRNT50) value was 1.0 µM (FIG. 2A). Yield reduction experiments further verified the antiviral activity, and peptide concentration which reduced virus yield by 50% (IC50) was determined to be 1.1 µM (FIG. 2B). Cytotoxicity experiments were also conducted against the Vero cells as well as several mammalian cell lines, including erythrocyte, epithelial and endometrial cell lines (FIG. 2C). There was minimal cytotoxicity observed against all tested cell lines at the highest tested concentration of 50 µM, which is consistent with membrane curvature-selectivity and indicative of a high therapeutic index. Moreover, the effect of peptide treatment on the viability of several important *Lactobacillus* bacterial species that contribute to the natural defenses of the vaginal microenvironment were also investigated (Fernandez-Romero et al., Advanced Drug Delivery Reviews 92, 27 (2015)) (FIG. 2D). Again, there was minimal toxicity against the tested bacterial species, supporting that the peptide is well-suited for microbicidal applications. Collectively, the results demonstrate that the peptide selectively targets ZIKV particles over relevant mammalian and bacterial cell lines.

The findings in this work present the first evidence that membrane-active agents can diminish the infectivity of ZIKV particles, and this antiviral activity occurs in a highly targeted manner with low toxicity against relevant mammalian and bacterial cell lines of importance to human health. While the development of humanized antibodies and vaccines will remain a key goal in the long-term development of ZIKV treatment options, envelope-targeting agents represent a complementary approach that could work synergistically in drug cocktails and there is a likely a higher barrier to the emergence of resistant virus strains against drugs in this class because the viral envelope is derived from host cell membranes. A peptide analogue to which a 24-unit polyethylene glycol (PEG) chain was attached at the N-terminus, retained neutralizing activity, thereby supporting the potential of developing therapeutically effective formulations with longer half-lives and greater resistance to proteolytic degradation (Roberts et al., Advanced Drug Delivery Reviews 64, 116 (2012)). Furthermore, membrane-active peptides have received growing attention for topical microbicide applications with long durability and strong ex vivo performance for HIV protection (Denton et al., Journal of virology 85, 7582 (2011); Maskiewicz et al., Antimicrobial Agents and Chemotherapy 56, 3336 (2012); Veazey et al., Antimicrobial Agents and Chemotherapy 60, 693 (2016)), and the demonstrated capacity of the peptide in this study to disrupt ZIKV envelopes would be useful for such applications.

Collectively, this example demonstrates that disruption of ZIKV particles by targeting the viral envelope represents an effective inhibitory strategy against ZIKV infection. While ZIKV particles are understood to have greater thermal stability and more compact structures than those of other flaviviruses, it was identified that their viral envelopes remain vulnerable to treatment with membrane-active compounds. Membrane-active entry inhibitors with selective targeting (e.g., membrane curvature sensitivity) could become an important part of ZIKV countermeasures as well as provide a broad-spectrum, rapid response to other emerging and reemerging, enveloped viruses.

6.6 Example 6

Evaluation of Anti-HIV Activity and Cellular Toxicity by TSG001 in In Vitro Cell-Based Assays This example describes the inhibition of HIV-1$_{BaL}$ in human peripheral blood mononuclear cells (PBMCs), HIV-1 virucidal activity and toxicity to cells relevant to the vaginal and rectal environments and the normal vaginal flora *Lactobacillus* by compound TSG001 was evaluated.

6.6.1 Materials and Methods

Human PBMCs: Fresh PBMCs determined to be seronegative for HIV and HBV were isolated from blood obtained from Biological Specialty Corporation (Colmar, PA).

Cell Lines: The Ca Ski (ATCC CRL-1550), HEC1A (ATCC HTB-112), ME180 (ATCC HTB-33) and Caco-2 (ATCC HTB-37) cell lines used in the toxicity evaluations were obtained from the American Type Culture Collection (ATCC), Manassas, VA The MT-2 cells used in the HIV-1 virucidal assay were obtained from the AIDS Research and Reference Program (Rockville, MD). The cells were propagated as recommended by the suppliers and stored in liquid nitrogen.

Bacteria: *Lactobacillus jensenii* (ATCC 25258), *Lactobacillus crispatus* (ATCC 33820) and *Lactobacillus acidophilus* (ATCC 11975) were obtained from the ATCC. Each strain was grown in MRS media (Becton Dickinson catalog #288130), which allows for facultative anaerobic growth conditions, as indicated by the ATCC. Bacterial stocks were prepared and stored in 15% glycerol at −80° C.

Viruses: The HIV-1$_{BaL}$ and HIV-1$_{RF}$ used in the HIV-1 inhibition assay were obtained from the AIDS Research and Reference Program (Rockville, MD). The viruses were stored at −80° C. To prepare the concentrated HIV-1$_{RF}$ the virus pool was centrifuged at 1000 RPMs for 15 minutes at 4° C. The supernatant was transferred to an appropriate plastic tube and centrifuged at 32,500×g (15,000+/−200 RPMs) for 90 minutes at 4° C. The supernatant was decanted and the virus pellet was re-suspended in a fraction (e.g.

¹⁄₂₀₀th) of the volume of complete RPMI 1640 without phenol red. All re-suspended pellets were mixed, placed in aliquots in cryovials and stored at −80° C. until use.

Tissue Culture Medium: The contents of the tissue culture medium used are provided in Table 34.

TABLE 34

Media Components

| Media Component/Volume | ME180 Cells | Ca Ski Cells | HEC1A Cells | Caco-2 Cells | MT-2 Cells | Human PBMCs |
|---|---|---|---|---|---|---|
| Basal Medium (500 mL) | RPMI-1640 (LONZA 12-702F) | RPMI-1640 (LONZA 12-702F) | McCoy's 5A (Lonza 12-688F) | EMEM (ATCC 30-2003) | RPMI-1640 (LONZA 12-918) | RPMI-1640 (LONZA-12-918F) |
| FBS Concentration (% v/v) (Invitrogen 16140-071) | 10 | 10 | 10 | 20 | 10 | 15 |
| Penicillin/Streptomycin U/mL, mg/mL (Lonza 17-602E) | 100/100 | 100/100 | 100/100 | 100/100 | 100/100 | 100/100 |
| L-glutamine mmol/liter (Lonza - 17-605E) | 2 | 2 | 2 | 2 | 2 | 2 |

Human PBMC Isolation: Leukopheresed human donor blood was obtained from Biological Specialty Corporation (Colmar, PA). The leukophoresed blood cells were washed two times with Dulbecco's phosphate buffered saline (DPBS, Lonza, catalog #17-512F). After washing, the cells were diluted 1:1 with DPBS and layered over 15 mL of Ficoll-Hypaque density gradient in a 50 mL conical centrifuge tube. The tubes were centrifuged for 30 minutes at 600×g. The band within the gradient containing the PBMCs was gently aspirated from the resulting interface. The isolated cells were washed three times with DPBS by low speed centrifugation. After the final wash, cells were enumerated by Trypan Blue dye exclusion, re-suspended at 1×10⁶ cells/mL in tissue culture medium (RPMI 1640 supplemented with 15% FBS, 2 mmol/L L-glutamine, 2 µg/mL PHA-P (Sigma Aldrich, catalog #L1932), 100 Units/mL penicillin and 100 µg/mL streptomycin), and incubated for 48-72 hours at 37° C./5% $CO_2$. Following this incubation, the PBMCs were collected by centrifugation and resuspended in tissue culture medium (RPMI 1640 supplemented with 15% FBS, 2 mmol/L L-glutamine, 100 U/mL penicillin, 100 µg/mL streptomycin and 3.6 ng/mL recombinant human IL-2). The cultures were then maintained until use by half culture volume change with fresh IL-2 containing tissue culture medium every 3 days.

(a) Evaluation of HIV-1$_{US/92/727}$ Activity in Human PBMCs

Assays were performed with PBMCs that had been induced to proliferate with PHA-P for 72 hours. PHA-P stimulated PBMCs from three donors were pooled together to minimize the variability that occurs when cells from individual donors are used. PBMCs were collected by centrifugation, re-suspended in fresh tissue culture medium at 1×10⁶ cells/mL and plated in the interior wells of a 96-well round bottom microtiter plate at 50 µL/well. The test compounds were diluted in half-logarithmic increments and 100 µL of each concentration of compound-containing medium was transferred to designated wells of the round-bottom 96-well plate containing the cells in triplicate Immediately following addition of the compound to the wells, 50 µL of a predetermined dilution of virus was added. After 7 days in culture at 5% $CO_2$/37° C. HIV-1 replication was quantified by the measurement of cell-free HIV-1 RT activity in the tissue culture supernatant as described below. Cytotoxicity was evaluated using the tetrazolium dye XTT as described below.

Reverse Transcriptase (RT) Activity Assay: Reverse transcriptase activity was measured in cell supernatants using a standard radioactive incorporation polymerization assay. Tritiated thymidine triphosphate (TTP) was purchased at 1 Ci/mL and 1 µL was used per enzyme reaction. Poly rA and oligo dT were prepared at concentrations of 0.5 mg/mL and 1.7 Units/mL, respectively, from a stock solution which was kept at −20° C. The RT reaction buffer was prepared fresh on a daily basis and consists of 125 µL of 1 M EGTA, 125 µL of $dH_2O$, 125 µL of 20% Triton X-100, 50 µL of 1 M Tris (pH 7.4), 50 µL of 1 M DTT, and 40 µL of 1 M $MgCl_2$. For each reaction, 1 µL of TTP, 4 µL of $dH_2O$, 2.5 µL of rAdT and 2.5 µL of reaction buffer were mixed. Ten microliters (10 µL) of this reaction mixture was placed in a round bottom microtiter plate with 15 µL of virus containing supernatant. The plate was incubated at 37° C. in a humidified incubator for 60 to 90 minutes. Following the incubation, 10 µL of the reaction volume was spotted onto a DEAE filter mat (Perkin Elmer, catalog #1450-522) in the appropriate plate format, washed 5 times for 5 minutes each in a sodium (150 mM) citrate (15 mM) buffer (Invitrogen, catalog #15557-036), 2 times for 1 minute each in deionized water (ImQuest), 2 times for 1 minute each in 70% reagent alcohol (Fisher, catalog #L-7168), and then air dried. The dried filtermat was placed in a plastic sleeve and 4 mL of Opti-Fluor O (Perkin Elmer, catalog #1205-440) scintillation fluid was added to each sleeve. Incorporated radioactivity was quantified utilizing a Wallac 1450 Microbeta Trilux liquid scintillation counter.

XTT Staining for Cell Viability and Compound Cytotoxicity: Cellular toxicity reported as TC50 values for the test materials was derived by measuring the reduction of the tetrazolium dye XTT ((2,3-bis(2-methoxy-4-nitro-5-sulfophenyl)-5-[(phenylamino)carbonyl]-2H-tetrazolium hydroxide). XTT (Sigma-Aldrich, catalog #X4626-500 mg) is metabolized by the mitochondrial enzyme NADPH oxidase to a soluble formazan product in metabolically active cells. XTT solution was prepared daily as a stock of 1 mg/mL in RPMI-1640 without additives. Phenazine methosulfate (PMS, Sigma-Aldrich, catalog #P9625-1G) solution was prepared at 0.15 mg/mL in DPBS and physically stored in a light proof container at −20° C. XTT/PMS stock was prepared immediately before use by adding 40 µL of PMS per mL of XTT solution. Fifty µL (50 µL) of XTT/PMS was added to each well of the plate and the plate incubated for 4 hours at 37° C. in 5% $CO_2$. The 4 hour incubation has been empirically determined to be within the linear response range for XTT dye reduction with the indicated numbers of cells for each assay. The plates were sealed with an adhesive plate cover and inverted several times to mix the soluble formazan product and the absorbance was determined at 450 nm (650 nm reference wavelength) with a Molecular Devices SpectraMax Plus 384 96 well plate format spectrophotometer.

Data Analysis: Microsoft Excel 2010 was used to analyze and graph data. EC50 (50% inhibition of virus replication), TC50 (50% reduction in cell viability) and a therapeutic index (TI, TC50/EC50) are provided. The EC values and TC values were determined using linear regression analysis.

(b) Inhibition of the Normal Vaginal Flora *Lactobacillus*

MRS broth was prepared by dissolving 55 grams of powder in 1 liter of deionized water. The broth was boiled to dissolve the powder completely and sterilized at 121° C./17.5 psi for 15 minutes. Following sterilization the broth was stored at 4° C. prior to use. MRS broth was inoculated using a 10 µL loop of each bacterial strain (*Lactobacillus jensenii, Lactobacillus crispatus* or *Lactobacillus acidophilus*) from glycerol stocks and the cultures were incubated anaerobically in anaerobic jars using GasPak EZ Anaerobic Container System pouches (BD, catalog #260678) for 24 hours at 37° C. The resultant culture was used to prepare freshly grown liquid stocks using the same procedure. After the final incubation the bacterial density was adjusted to an OD625 of 0.06 in MRS broth. Six serial half-logarithmic dilutions of the compound were prepared and added in triplicate in a volume of 100 µL to a 96-well round bottom plate. As an assay control, six serial two-fold dilutions of Penicillin/Streptomycin solution at a high test of 1.25 U/mL and 1.25 µg/mL, respectively were prepared and added in triplicate to a 96-well round bottom plate. Each culture of *Lactobacillus* with the adjusted density described above was added to the appropriate wells of the plate. The cultures were incubated anaerobically for 24 hours as described above and bacterial growth was evaluated spectrophotometrically at 490 nM using a Spectramax 340 PC384 (Molecular Devices).

Data Analysis: Raw data generated by the Spectramax plate reader was transferred to a spreadsheet (Microsoft Excel) where linear regression analysis was used to determine the concentration of test compound resulting in 50% reduction in bacterial growth.

(c) Evaluation of Cellular Toxicity to Cells Relevant to the Vaginal and Rectal Compartments ME180, Ca Ski, HEC1A and Caco-2 cells were added to a 96-well flat bottomed plate 24 hours prior to the addition of compound at a density of $5.0 \times 10^4$ cells/well in a total volume of 200 µL. Six concentrations of each compound were serially diluted ½ log (nonoxynol-9 control (referred to herein as "N9")) or 1:2 (TSG001) and added in a volume of 200 µL in triplicate to the seeded cells following removal of the media. The plates were incubated for 24 hours at 37° C./5% $CO_2$. Following the incubation the cells were washed three times with RPMI-1640 without additives. Two-hundred microliters (200 µL) of complete medium for each specified cell line was then added to the plates and allowed to incubate at 37° C./5% $CO_2$ for an additional 24 hours. Cellular toxicity was evaluated using the tetrazolium dye XTT as described above.

Data Analysis: Microsoft Excel 2010 was used to analyze and graph data. The TC50 (50% reduction in cell viability) is provided. The TC50 value was determined using linear regression analysis. Raw data for the toxicity with a graphic representation of the data are provided in the appendices summarizing the individual compound toxicity.

MT-2 cells were added to a 96-well flat-bottomed plate at a density of $1 \times 10^4$ cells/well in a volume of 100 µL. Six concentrations of the compound TSG001 and the control compound nonoxynol-9 (N-9) were prepared in RPMI-1640 assay media and 95 µL of each concentration was mixed with concentrated HIV-1$_{RF}$ virus stock to yield 6 to 7 logs of virus activity (5 µL of a 100× virus stock), for one hour at 37° C./5% $CO_2$. For the evaluation of toxicity, 95 µL of compound was mixed with 5 µL of RPMI-1640 assay media. For the virus control, 95 µL of media was mixed with 5 µL of the 100× virus stock. At the end of the 1 hour exposure period, 6 serial 10-fold dilutions were performed. One-hundred microliters (100 µL) of the serial dilutions were transferred to the plate with pre-seeded MT2 cells. Each dilution was plated in quadruplicate. The samples being evaluated for compound toxicity was plated in duplicate. The plates were incubated for 7 days at 37° C./5% $CO_2$. They were microscopically observed and scored on day 3 and day 6 for virus-induced cytopathic effect and agent-induced cytotoxicity.

6.6.2 Results (a) Evaluation of TSG001 for Efficacy and Toxicity Against HIV-1 in Human PBMCs Anti-infective peptide TSG001 (SEQ ID NO:1) was evaluated for anti-HIV-1 activity in human PBMCs and it was determined to have an EC50 of 3.47 µM Against the CCR-5 tropic HIV-1$_{US/92/727}$. TSG001 was toxic to the PBMCs having a TC50 of 31.0 µM which yielded a therapeutic index (TI) of 8.93. AZT was evaluated in parallel and had an EC50 of 0.0029 µM. These data are presented in Table 35.

TABLE 35

Efficacy and Toxicity of TSG001 (SEQ ID NO: 1) in Human PBMCs Against HIV-1$_{US/92/727}$.

|  | $TC_{50}$ (µM) | $EC_{50}$ (µM) | TI |
|---|---|---|---|
| AZT | >1.0 | 0.00292 | >342.5 |
| TSG001 (SEQ ID NO: 1) | 31.0 | 3.47 | 8.93 |

(b) Evaluation of Cell Lines Representative of the Vaginal and Rectal Environments Anti-infective peptide TSG001 (SEQ ID NO:1) was evaluated for toxicity to cells that are representative of the vaginal and rectal environments. The compound was exposed to the cells for 24 hours and then the cells were evaluated for cytopathic effect (CPE) at 48 hours post addition. Anti-infective peptide TSG001 (SEQ ID NO:1) was found to be non-toxic to Ca Ski, HEC1A, and Caco-2 cells up to the highest concentration evaluated (50 µM). Anti-infective peptide TSG001 (SEQ ID NO:1) was toxic to ME180 cells having a TC50 value of 37.0 µM. Nonoxynol-9 (N-9) was evaluated in parallel and was toxic at the expected concentration in each of the cell lines. These data are presented in Table 36.

TABLE 36

Evaluation of Cellular Toxicity by TSG001 (SEQ ID NO: 1) in Cells Representative of the Vaginal and Rectal Environments

|  | ME180 $TC_{50}$ | Ca Ski $TC_{50}$ | HEC1A $TC_{50}$ | Caco-2 $TC_{50}$ |
|---|---|---|---|---|
| N-9 (μg/mL) | 74.0 | 61.3 | 62.9 | 55.1 |
| TSG001 (μM) | 37.04 | >50 | >50 | >50 |

(c) Evaluation of Toxicity to the Normal Vaginal Flora *Lactobacillus* by TSG001

Anti-infective peptide TSG001 (SEQ ID NO:1) was evaluated for toxicity to three strains of *Lactobacillus* including *L. acidophilus*, *L. jensenii* and *L. crispatus* and was found to be non-toxic to all three strains up to the highest concentration evaluated (50 μM). Penicillin/Streptomycin solution was evaluated in parallel as a positive control and was active at the expected concentrations. Deionized water was used as a negative control. These data are presented in Table 37.

TABLE 37

Evaluation of Toxicity to the Normal Flora *Lactobacillus* by TSG001 (SEQ ID NO: 1)

|  | *L. acidophilus* $TC_{50}$ | *L. jensenii* $TC_{50}$ | *L. crispatus* $TC_{50}$ |
|---|---|---|---|
| Penicillin/Streptomycin Solution (Dilution) | 1:31,746 | 1:40,486 | 1:40,000 |
| TSG001 (μM) | >50 | >50 | >50 |
| Deionized Water (Dilution) | >1:100 | >1:100 | >1:100 |

(d) Evaluation of the Virucidal Activity of TSG001 Against HIV-1RF in MT-2 Cells Six concentrations of anti-infective peptide TSG001 (SEQ ID NO:1) were incubated with HIV-$1_{RF}$ for 1 hour and then diluted in serial 10-fold increments and exposed to MT-2 cells. On days 3 and 6 post exposure to the virus the cells were scored for the presence of syncytia with a "+" or "−". The TCID50 was determined at each concentration evaluated. On day 3, the virus control had a TCID50 of 5.3. TSG001 (SEQ ID NO:1) had TCID50s ranging from 3.9 to 5.8 at concentrations of 50 μM to 0.15 μM. The highest log reduction in virus titer was 1.4 at 50 μM. On day 6 the virus control had a TCID50 of 6.5. TSG001 (SEQ ID NO:1) had TCID50s ranging from 5.0 to >6.6 at concentrations of 50 μM to 0.15 μM. The highest log reduction in virus titer was a 1.5 log reduction at 50 μM. N-9 was evaluated in parallel and had levels of reduction in virus titer as expected. These data are presented in Table 38.

TABLE 38

Evaluation of TSG001 (SEQ ID NO: 1) HIV-$1_{RF}$ Virucidal Activity in MT-2 Cells

| Sample | Stock Solution | Concentration of Agent During Exposure | TCID50 Sample - Virus | TCID50 Cytotoxicity | Log Reduction in Virus Titer |
|---|---|---|---|---|---|
| Virus Control |  |  |  |  | 5.3 |
| Nonoxynol 9 - Day 3 | 10,000 μg/mL | 1000 | ≤2.5 | ≤2.5 | ≥2.8 |
|  |  | 100 | ≤2.0 | ≤2.0 | ≥3.3 |
|  |  | 10 | 5.3 | 0 | 0 |
|  |  | 1 | 5 | 0 | 0.3 |
|  |  | 0.1 | 5 | 0 | 0.3 |
|  |  | 0.01 | 5 | 0 | 0.3 |
| TSG001 - Day 3 | 5,000 μM | 50 | 3.9 | ≤0.5 | 1.4 |
|  |  | 15 | 5 | 0 | 0.3 |
|  |  | 5 | 5.3 | 0 | 0 |
|  |  | 1.5 | 5.6 | 0 | 0 |
|  |  | 0.5 | 5.8 | 0 | 0 |
|  |  | 0.15 | 5.3 | 0 | 0 |
| Virus Control |  |  |  |  | 6.5 |
| Nonoxynol 9 - Day 6 | 10,000 μg/mL | 1000 | ≤3.8 | ≤2.5 | ≥2.7 |
|  |  | 100 | 3.6 | ≤1.5 | 2.9 |
|  |  | 10 | ≥6.6 | 0 | 0 |
|  |  | 1 | ≥6.6 | 0 | 0 |
|  |  | 0.1 | 5.8 | 0 | 0.7 |
|  |  | 0.01 | 6 | 0 | 0.5 |
| TSG001 - Day 6 | 5,000 μM | 50 | 5 | ≤0.5 | 1.5 |
|  |  | 15 | 5.6 | 0 | 0.9 |
|  |  | 5 | 5.8 | 0 | 0.7 |
|  |  | 1.5 | 5.8 | 0 | 0.7 |
|  |  | 0.5 | 6.3 | 0 | 0.2 |
|  |  | 0.15 | ≥6.6 | 0 | 0 |

6.6.3 Conclusion

Anti-infective peptide TSG001 (SEQ ID NO:1) was found to be active in human PBMCs with an EC50 value of 3.47 µM and yielded a 1.5 log reduction in virus titer at 50 µM when evaluated against HIV-$1_{RF}$ in a virucidal assay. Anti-infective peptide TSG001 (SEQ ID NO:1) was toxic to PBMCs and ME180 cells at a concentration approximately 10-fold higher than the defined EC50 value. TSG001 was not toxic to the epithelial cells Ca Ski, HEC1A and Caco-2 or to the normal vaginal flora *Lactobacillus* up to the highest concentration evaluated of 50 µM.

6.7 Example 7

In Vitro Activity of TSG001, Ciprofloxacin, and Clindamycin Against Evaluated Bacteria This example describes the antibacterial activity of the anti-infective peptide TSG001 (SEQ ID NO:1) against various species and strains of bacteria.

6.7.1 Materials and Methods

Specific information on the individual drug lots is shown below. Once appropriate solvents were added to the comparator drugs, the stock solutions were allowed to stand for approximately 1 hour at room temperature to auto sterilize before aliquoting and freezing at −80° C. On the day of the assay, a fresh aliquot of frozen stock solutions of the comparator drugs at 40-fold the highest concentration in the test plates was removed from the −80° C., thawed, and was used for testing.

TABLE 39

Compounds used in this example.

| Drug | Source | Catalog No. | Lot No. | Storage Temp. | Concentration Ranges tested (µg/ml) | Solvent |
|---|---|---|---|---|---|---|
| TSG001 (SEQ ID NO: 1) | N/A | | | −20° C. | 64-0.06 | water |
| Ciprofloxacin | USP | 1134335 | J1L040 | −20° C. | 64-0.002 | water |
| Clindamycin | Sigma | M3761 | 021M1533V | 4° C. | 64-0.06 | water |

(a) Organisms

The test organisms were acquired from the American Type Culture Collection (ATCC) and from clinical laboratories. Upon receipt, the isolates were streaked under suitable conditions onto agar medium appropriate for each organism. The plates containing anaerobic organisms were incubated anaerobically at 35° C. for 48 hours in a Bactron II Anaerobic Chamber (Sheldon Manufacturing Inc., Cornelius, OR). Aerobic organisms were incubated for 18-24 hours at 35° C. Colonies harvested from these growth plates were resuspended in the appropriate medium containing a cryoprotectant. Aliquots of each suspension were then frozen at −80° C. Prior to the assay, the organisms were thawed and sub-cultured on appropriate agar plates and incubated as described above.

The following Quality Control isolates were included as part of the tested isolates: *Clostridium difficile* ATCC 700057, *Escherichia coli* ATCC 25922, *Staphylococcus aureus* ATCC 29213, *Enterococcus faecalis* ATCC 29212, *Pseudomonas aeruginosa* ATCC 27853, and *Streptococcus pneumoniae* ATCC 49619.

(b) Test Media

For anaerobic organisms, susceptibility testing was conducted in BBL Brucella broth (BRU; Becton Dickinson; Sparks, MD; Lot No. 2311 123). BRU broth was supplemented with vitamin K1 (Sigma-Aldrich; St. Louis, MO; Lot No. MKBNS958V), hemin (Sigma-Aldrich; Lot No. SLBD8813V), and 5% laked horse blood (Cleveland Scientific; Bath, OH; Lot No. 222808). Agar plates for anaerobic organisms were Supplemented Brucella Agar plates (Remel, Lenexa, KS; Lot No. 484569).

For aerobic organisms, the medium employed for the MIC assay was Mueller-Hinton Broth (MHB II-Becton Dickinson; Lot No. 4293655) with the exception of *Haemophilus influenzae* which was tested in Haemophilus Test Medium (HTM; Teknova; Hollister, CA; Lot No. H580025K1401). MHB II was supplemented with 3% laked horse blood (Cleveland Scientific; Lot No. 222808) for *streptococci*. Agar plates used for aerobic organisms were trypticase soy agar plus 5% sheep blood (Remel; Lot No. 629110) with the exception of *H. influenzae* which was streaked onto Chocolate Agar (Becton Dickinson, Lot No. 4260888).

(c) MIC Assay Methodology

MIC assay plates were prepared using the CLSI broth microdilution procedure (see, e.g., Jorgensen, James H., and John D. Turnidge. "Susceptibility test methods: dilution and disk diffusion methods." Manual of Clinical Microbiology, Eleventh Edition. American Society of Microbiology, 2015. 1253-1273.). Automated liquid handlers (Biomek 2000 and Biomek FX, Beckman Coulter, Fullerton CA) were used to conduct serial dilutions and liquid transfers. All wells in columns 2-12 of a standard 96-well microdilution plate (Costar 3795) were filled with 150 µL of the appropriate solvent. Three hundred µL of each test drug (at 40×) was added to each well in Column 1 of the plates. This plate was used to prepare the drug "mother plate" which provided the serial drug dilutions for the replicate "daughter plates". The Biomek 2000 was used to complete the serial transfers through Column 11 in the mother plates. The wells of Column 12 contained no drug, representing the organism growth control wells.

The daughter plates were loaded with 185 µL per well of the test media described above using the Multidrop 384. The daughter plates were completed on the Biomek FX instrument which transferred 5 µL of drug solution from each well of a mother plate to each corresponding well of each daughter plate in a single step.

The anaerobe daughter plates containing media and drug were transferred to the Bactron II anaerobe chamber and allowed to reduce for 1 hour prior to inoculation.

A standardized inoculum of each organism was prepared per CLSI methods (see, e.g., Jorgensen, James H., and John D. Turnidge. "Susceptibility test methods: dilution and disk diffusion methods." Manual of Clinical Microbiology, Eleventh Edition. American Society of Microbiology, 2015. 1253-1273). Suspensions were prepared to equal a 0.5 McFarland standard. The suspensions were additionally diluted in broth appropriate to the organism. The anaerobic plates were inoculated with 10 µL of standardized inoculum by hand from low to high drug concentration under anaerobic conditions, resulting in approximately $1 \times 10^5$ colony-forming-units/mL. The wells of the daughter plates ultimately contained 185 µL of broth, 5 µL of drug solution, and 10 µL of bacterial inoculum. For each assay, one extra plate of medium including the drug solutions (no inoculum) was prepared for the purpose of assessing solubility of the drug in the test medium. Anaerobe plates were stacked 3 high, covered with a lid on the top plate, placed in a BD GasPak EZ Anaerobe Container System and incubated at 35° C. for 46-48 hours.

The inocula for the aerobic organisms were dispensed into sterile reservoirs divided by width (Beckman Coulter) and the Biomek 2000 was used to inoculate the plates. Daughter plates were placed on the Biomek 2000 work surface reversed so that inoculation took place from low to high drug concentration. The Biomek 2000 delivered 10 µL of aerobic culture standardized inoculums into each well. These inoculations yielded a final cell concentration in the daughter plates of approximately $5 \times 10^5$ colony-forming-units/mL The wells of the daughter plates ultimately contained 185 µL of broth, 5 µL of drug solution, and 10 µL of bacterial inoculum. For each test medium, one extra plate including the drug solutions was prepared for the purpose of assessing solubility of the drug in the test medium (un-inoculated solubility control plate). Aerobe plates were stacked 3-4 high, covered with a lid on the top plate, placed in plastic bags, and incubated at 35° C. for approximately 20 hours, with the exception of Mycobacterium smegmatis which was incubated for 48 hours. Of note, the same inocula of S. aureus ATCC 29213 was used to inoculate panels containing MHB II, and MHB II supplemented with 10% human serum.

The microplates were viewed from the bottom using a plate viewer, and the MIC was read and recorded as the lowest concentration of drug that inhibited visible growth of the organism. The un-inoculated solubility control plate was observed for evidence of drug precipitation.

6.7.2 Results

The in vitro susceptibility testing results are shown in Tables 40-42. Evaluation of the MIC values obtained for the quality control organisms and their respective quality control antibiotics revealed that all were within the range established by CLSI (see, e.g., Jorgensen, James H., and John D. Turnidge. "Susceptibility test methods: dilution and disk diffusion methods." Manual of Clinical Microbiology, Eleventh Edition. American Society of Microbiology, 2015. 1253-1273). For clindamycin and C. difficile ATCC 700057, the broth microdilution MIC was one dilution below the acceptable range for agar dilution testing. This precipitation did not interfere with interpretation of the MIC endpoint, but in instances where precipitation was observed the dissolved concentration of drug in these wells were likely impacted.

The anti-infective peptide TSG001 (SEQ ID NO:1) was active against the evaluated aerobic Gram-positive bacterial isolates (S. aureus, enterococci, streptococci, and B. anthracis) with MICs ranging from 2-16 µg/mL. This activity was maintained against MRSA, VRE, PRSP, as well as ciprofloxacin and clindamycin-resistant isolates.

Against the evaluated aerobic Gram-negative isolates (E. coli, K. pneumoniae, P. aeruginosa, M. catarrhalis, and H. influenzae), the anti-infective peptide TSG001 (SEQ ID NO:1) was only active against the fastidious isolates with an MIC of 1 µg/mL against M. catarrhalis and an MIC of 8 µg/mL for H. influenzae. The anti-infective peptide TSG001 (SEQ ID NO:1) was inactive (MICs >64 µg/mL) against E. coli, K. pneumoniae, and P. aeruginosa.

Against the lone mycobacterium isolate tested (M. smegmatis), some activity was observed for the anti-infective peptide TSG001 (SEQ ID NO:1) with an MIC of 32 µg/mL. The anti-infective peptide TSG001 (SEQ ID NO: 1) was also active against the evaluated Gram-positive anaerobic isolates C. difficile (MIC of 32 µg/mL) and P. acnes (MIC of 16 µg/mL).

TABLE 40

In vitro activity of the anti-infective peptide TSG001 (SEQ ID NO: 1), ciprofloxacin, and clindamycin against evaluated bacteria. MSSA refers to methicillin-sensitive Staphylococcus aureus. MRSA refers to methicillin-resistant Staphylococcus aureus. VSE refers to vancomycin-sensitive enterococci. VRE refers to vancomycin-resistant enterococci. PSSP refers to penicillin-sensitive Streptococcus pneumoniae.

| Type | Staphylococcus aureus MSSA | Staphylococcus aureus MRSA | Staphylococcus aureus MRSA | Enterococcus faecalis VSE | Enterococcus faecalis VRE | Enterococcus faecium VRE | Streptococcus pneumoniae PSSP |
|---|---|---|---|---|---|---|---|
| TSG001 (SEQ ID NO: 1) (MIC, µg/mL) | 4 | 8 | 4 | 4 | 8 | 4 | 16 |
| Ciprofloxacin (MIC, µg/mL) | 0.5 (0.12-0.5)[1] | >64 | 64 | 0.5 (0.25-2) | 32 | >64 | 1 |
| Clindamycin (MIC, µg/mL) | 0.12 (0.06-0.25) | ≤0.06 | ≤0.06 | 16 (4-16) | >64 | >64 | ≤0.06 (0.03-0.12) |

TABLE 41

In vitro activity of the anti-infective peptide TSG001 (SEQ ID NO: 1), ciprofloxacin, and clindamycin against evaluated bacteria. PRSP refers to penicillin-resistant Streptococcus pneumoniae.

| Type | Streptococcus pneumoniae PRSP | Streptococcus pyogenes | Streptococcus agalactiae | Streptococcus salivarius | Bacillus anthracis Sterne | Mycobacterium smegmatis[1] | Haemophilus influenzae | Moraxella catarrhalix |
|---|---|---|---|---|---|---|---|---|
| TSG001 (SEQ ID NO: 1) (MIC, µg/mL) | 16 | 8 | 16 | 8 | 2 | 32 | 8 | 1 |

TABLE 41-continued

In vitro activity of the anti-infective peptide TSG001 (SEQ ID NO: 1), ciprofloxacin, and clindamycin against evaluated bacteria. PRSP refers to penicillin-resistant *Streptococcus pneumoniae*.

| Type | *Streptococcus pneumoniae* PRSP | *Streptococcus pyogenes* | *Streptococcus agalactiae* | *Streptococcus salivarius* | *Bacillus anthracis* Sterne | *Mycobacterium smegmatis*[1] | *Haemophilus influenzae* | *Moraxella catarrhalix* |
|---|---|---|---|---|---|---|---|---|
| Ciprofloxacin (MIC, µg/mL) | 2 | 0.25 | 0.5 | 1 | 0.03 | 0.25 | 0.015 (0.004-0.03) | 0.03 |
| Clindamycin (MIC, µg/mL) | >64 | ≤0.06 | ≤0.06 | ≤0.06 | 0.25 | 16 | 4 | 1 |

[1]MIC determined after 48 hours of incubation

TABLE 42

In vitro activity of the anti-infective peptide P1 (SEQ ID NO: 1), ciprofloxacin, and clindamycin against evaluated bacteria.

| Type | *Escherichia coli* | *Escherichia coli* ΔacrAB | *Pseudomonas aeruginosa* | *Klebsiella pneumoniae* | *Clostridium difficile*[1] | *Propionibacterium acnes*[1] |
|---|---|---|---|---|---|---|
| TSG001 (SEQ ID NO: 1) (MIC, µg/mL) | >64 | >64 | >64 | >64 | 32 | 16 |
| Ciprofloxacin (MIC, µg/mL) | 0.008 (0.004-0.015) | 0.004 | 0.25 (0.25-1) | 0.25 | 8 | 0.5 |
| Clindamycin (MIC, µg/mL) | >64 | 4 | >64 | >64 | 1 (2-8)[2] | ≤0.06 |

[1]MIC determined after 48 hours of incubation
[2]Agar dilution CLSI QC range shown in parenthesis for clindamycin In summary, the anti-infective peptide TSG001 (SEQ ID NO:1) was active against Gram-positive aerobes (*S. aureus, enterococci, streptococci*, and *B. anthracis*) including resistant isolates, fastidious Gram-negative respiratory pathogens (*H. influenzae* and *M. catarrhalis*), *M. smegmatis*, and the evaluated Gram-negative anaerobes (*C. difficile* and *P. acnes*). The anti-infective peptide TSG001 (SEQ ID NO:1) was inactive against Gram-negative aerobes (*E. coli, K. pneumoniae*, and *P. aeruginosa*).

6.8 Example 8

Antibacterial Activity of Anti-Infective Peptides Against *Staphylococcus aureus*

The antibacterial activity of the anti-infective peptides TSG001-TSG009 (SEQ ID NOS:1-9), along with the comparator peptides AH (SEQ ID NO:10) and C5A (SEQ ID NO:11), were tested against various *Staphylococcus aureus* (Table 43). To this end, *S. aureus* (ATCC 25923) (American Type Culture Collection, Manassas, VA) was cultured in LB broth overnight at 37° C. The suspension of the overnight culture was inoculated in fresh LB broth and cultured under aerobic conditions until reaching an OD600 value of approximately 0.5 (exponential growth phase). The bacterial cells were harvested by centrifugation at 1,500×g for 10 minutes, washed thrice with PB or PBS, and re-suspended in the appropriate solution for experiment. The bacterial cell suspensions were diluted to an OD600 value of 0.1, which corresponds to $1\times10^7$ CFU/mL for *S. aureus*. Before experiment, the bacterial cells were then diluted 1:10 with PB or PBS. The minimum inhibitory concentration (MIC) values of the test compounds were determined in PB or PBS solutions. For the PB and PBS cases, the MIC determination was made by a MH agar plate method. Two-fold serial dilutions of test compound solutions in PB or PBS were first made in a 96-well microtiter plate. The test compound concentration ranged from 0.3 µM to 100 µM with 50 µL volume. Then, 50 µL of *S. aureus* ($1\times10^6$ CFU/mL) suspended in PB or PBS was added to each well for a final cell density of $5\times10^5$ CFU/mL. The samples were incubated for 3 hours at 37° C., and then streaked onto MH agar plates. The plates were incubated overnight at 37° C. and the MIC value was recorded based on the lowest test compound concentration that inhibited colony growth. PB is defined as 10 mM potassium phosphate buffer, pH 7.2 and PBS is conventional phosphate-buffered saline.

Based on the MIC values, the anti-infective peptides are effective antibacterial agents whereas AH and C5A peptides do not display antibacterial activity. While most membrane-active peptides are sensitive to salt conditions, the anti-infective peptides had identical MIC values in PB and PBS conditions.

TABLE 43

Antibacterial activity against *Staphylococcus aureus*. MIC refers to mean inhibitory concentration (µM).

| Peptide | MIC in PB (µM) | MIC in PBS (µM) |
|---|---|---|
| AH (SEQ ID NO: 10) | >100 | >100 |
| C5A (SEQ ID NO: 11) | >100 | >100 |
| TSG001 (SEQ ID NO: 1) | 1.5 | 1.5 |
| TSG002 (SEQ ID NO: 2) | 1.5 | 1.5 |
| TSG003 (SEQ ID NO: 3) | 1.5 | 1.5 |
| TSG004 (SEQ ID NO: 4) | 1.5 | 1.5 |
| TSG005 (SEQ ID NO: 5) | 1.5 | 1.5 |
| TSG006 (SEQ ID NO: 6) | 1.5 | 1.5 |
| TSG007 (SEQ ID NO: 7) | 1.5 | 1.5 |

TABLE 43-continued

Antibacterial activity against *Staphylococcus aureus*. MIC refers to mean inhibitory concentration (μM).

| Peptide | MIC in PB (μM) | MIC in PBS (μM) |
|---|---|---|
| TSG008 (SEQ ID NO: 8) | 1.5 | 1.5 |
| TSG009 (SEQ ID NO: 9) | 1.5 | 1.5 |

6.9 Example 9

Circular Dichroism Spectra for Anti-Infective Peptides

Circular dichroism spectroscopy experiments on the anti-infective peptide TSG001 (SEQ ID NO:1) demonstrate that the membrane-bound peptide undergoes significant helical induction (27% increase), folding into a more active, α-helical state (83% helicity) in zwitterionic lipid vesicles (FIG. 1B). By contrast, CD measurements on both AH (SEQ ID NO:10) and C5A (SEQ ID NO:11) peptides lack helical induction in the membrane-associated state. Both AH (SEQ ID NO:10) and C5A (SEQ ID NO:11) peptides have high fractional helicities in buffer and 50% TFE (≈87% in both environments). In contrast to anti-infective peptide TSG001 (SEQ ID NO:1), AH (SEQ ID NO:10) peptide maintains a similarly high helical character (≈84%) while C5A (SEQ ID NO:11) peptide shows a marked reduction in helicity 64%). The structural change in C5A (SEQ ID NO:11) peptide is consistent with previous fluorescence spectroscopy measurements, which indicate lipid membranes modulate the secondary structure of C5A peptide. Importantly, the CD measurements in the present study clearly demonstrate that membrane binding has appreciably different effects on the secondary structures of anti-infective peptide TSG001 (SEQ ID NO: 1), AH (SEQ ID NO:10), and C5A (SEQ ID NO:11) peptides. The most favorable helix induction behaviors are observed with anti-infective peptide TSG001 (SEQ ID NO:1) only among these three peptides.

Helical Induction Ranking (greater positive helical induction is preferable for membrane activity): (1) anti-infective peptide TSG001 (SEQ ID NO:1): +27% helical induction; (2) AH (SEQ ID NO:10): −3% helical induction; and (3) C5A (SEQ ID NO:11): −23% helical induction.

Method: CD experiments were conducted on a AVIV Model 420 spectrometer (AVIV Biomedical, Lakewood, NJ, USA) using quartz cuvette with a 1 mm path length (Hellma). Spectral data were collected with a step size of 0.5 nm and averaging time of 4 s. All spectra were recorded at 25° C. from 190 to 260 nm using a bandwidth of 1-nm and averaged over three scans. The CD spectra were recorded before and after the addition of 2.5 mM 1-palmitoyl-2-oleoyl-sn-glycero-3-phosphocholine (POPC) lipid vesicles to 50 μM peptide. Baseline scans in buffer only or liposomes only were also performed using the same instrument settings, and this contribution was subtracted from respective data scans with peptides. The corrected spectra were expressed in mean residue molar ellipticity (Θ), and the fractional helicity of peptides was calculated as follows: $fH=([\Theta]222-3,000)/(-36,000-3000)$, where $[\Theta]222$ is the molar ellipticity at 222 nm.

6.10 Example 10

Membrane Partitioning Data for Anti-Infective Peptides

To determine the influence of vesicle size on membrane partitioning, intrinsic tryptophan fluorescence spectroscopy experiments were performed in order to calculate the mole fraction partition coefficient for each peptide as a function of vesicle size. Mole fraction partition coefficients, $K_x$, are presented as a function of vesicle size for each peptide (mean±standard deviation for n=3 independent experiments). ND means not determined in cases where the partition coefficient could not be determined due to minimal partitioning. The vesicle sizes are reported as mean vesicle diameter (dia.), which were determined by conventional dynamic light scattering measurements on vesicle suspensions.

TABLE 44

| | Membrane partition coefficient ($K_x \times 10^5$) | | | | | |
|---|---|---|---|---|---|---|
| Compound | 64 nm Diameter Vesicles | 85 nm Diameter Vesicles | 117 nm Diameter Vesicles | 159 nm Diameter Vesicles | 360 nm Diameter Vesicles | 665 nm Diameter Vesicles |
| TSG001 (SEQ ID NO: 1) | 7.7 ± 0.8 | 7.2 ± 0.0 | 6.6 ± 0.8 | 6.7 ± 0.4 | ND | ND |
| TSG002 (SEQ ID NO: 2) | 6.1 ± 0.2 | 5.4 ± 0.4 | 4.8 ± 0.1 | 4.3 ± 0.4 | ND | ND |
| TSG003 (SEQ ID NO: 3) | 12.7 ± 0.9 | 8.3 ± 0.9 | 6.6 ± 0.8 | 6.1 ± 0.4 | 6.7 ± 0.6 | 5.6 ± 0.1 |
| TSG004 (SEQ ID NO: 4) | 14.5 ± 1.6 | 14.1 ± 0.6 | 14.4 ± 0.9 | 12.2 ± 1.2 | ND | ND |
| TSG005 (SEQ ID NO: 5) | 12.2 ± 0.8 | 11.2 ± 0.1 | 8.0 ± 0.4 | 10.9 ± 0.2 | ND | ND |
| TSG006 (SEQ ID NO: 6) | 27.5 ± 0.8 | 24.4 ± 0.8 | 23.2 ± 0.8 | 24.2 ± 0.1 | 22.2 ± 0.2 | 12.5 ± 0.2 |
| AH (SEQ ID NO: 10) | 6.4 ± 1.2 | 7.4 ± 0.3 | 6.8 ± 0.4 | 6.7 ± 0.9 | ND | ND |
| C5A (SEQ ID NO: 11) | 56.7 ± 1.0 | 52.9 ± 2.3 | 52.2 ± 1.7 | 55.4 ± 0.6 | 54.5 ± 1.8 | 45.2 ± 0.9 |

Method: Fluorescence spectroscopy experiments were conducted on a Cary Eclipse fluorescence spectrophotometer (Varian, Inc., Australia). All measurements were performed using a 0.1 cm path length cuvette and a slit width of 5 mm. Tryptophan fluorescence was measured using excitation at 280 nm and scanning emission between 300 and 400 nm. Emission spectra were measured using 5 µM peptide in 10 mM potassium phosphate buffer, pH 7.2, titrated with unilamellar POPC lipid vesicles up to 150 µM (stepwise increments of 10 µM). For each titration point, the fluorescence intensity (I) at the emission maximum of the peptide (λmax) was normalized by the fluorescence intensity ($I_0$) of the peptide in buffer. Mole fraction partition coefficients ($K_x$) were determined based on fitting the experimental data to the following equation: $I/I_0=1+(I_{max}-1)(K_x[L]/K_x[L]+[W])$, where $I_{max}$ is the intensity after saturation of peptide-lipid binding, [L] is the molar lipid concentration, and [W] is the molar concentration of water (55.3 M).

Anti-infective peptides TSG001 (SEQ ID NO:1), TSG002 (SEQ ID NO:2), TSG004 (SEQ ID NO:4), and TSG005 (SEQ ID NO:5) were sensitive to membrane curvature, similar to AH (SEQ ID NO:10) peptide.

Anti-infective peptides TSG003 (SEQ ID NO:3) and TSG006 (SEQ ID NO:6) were not sensitive to membrane curvature, similar to C5A (SEQ ID NO:11) peptide.

Based on the quantitative values, anti-infective peptide TSG001 (SEQ ID NO:1) preserves the most similar membrane curvature sensitive properties to AH (SEQ ID NO:10) peptide. In particular, fluorescence spectroscopy experiments indicated strong partitioning of the tryptophan-containing anti-infective peptide TSG001 (SEQ ID NO:1) peptide into zwitterionic lipid bilayers, with a lipid-water partition constant on the order of $10^5$ for high-curvature vesicles below 200 nm diameter, and hence the binding-folding equilibrium within this regime favors the active, bound state. On the other hand, the peptide exhibits negligible partitioning into larger vesicles, indicating that the peptide behaves as a membrane curvature sensor and is preferentially active against highly curved membranes such as small, enveloped viruses.

6.11 Example 11

Quarts Crystal Microbalance-Dissipation (QCM-D) Measurements for Anti-Infective Peptides In order to characterize the vesicle-rupturing ability of the peptides, a surface-sensitive measurement approach was employed that included a layer of adsorbed lipid vesicles on a gold surface. Vesicles with controlled membrane composition (50 mol % 1,2-dioleoyl-sn-glycero-3-phosphocholine and 50 mol % cholesterol) and (≈size 80 nm diameter, as determined by dynamic light scattering measurements) were prepared by the extrusion method, and then deposited on the substrate (FIG. 3A and FIG. 3B). The vesicles adsorb and form a close-packed layer. The QCM-D technique is an acoustic sensor technique that measures the resonance frequency and energy dissipation of an oscillating titanium oxide-coated quartz crystal. When an adsorbate attaches to the gold-coated sensor surface, there are shifts in the frequency (Δf) and energy dissipation (ΔD) of the quartz crystal, which can be tracked as a function of time and correspond to the acoustic mass and viscoelastic properties of the adsorbate, respectively.

The interaction between anti-infective peptide TSG001 (SEQ ID NO:1), AH (SEQ ID NO:10), and C5A (SEQ ID NO:11) and surface-adsorbed vesicles composed of DOPC lipid and cholesterol were first examined. Extruded vesicles (≈80 nm diameter) were deposited on a gold substrate almost up to saturation. The corresponding QCM-D adsorption kinetics were consistent with formation of a close-packed, adsorbed vesicle layer (Δf≈−180 Hz and ΔD≈10× $10^{-6}$). The peptides were then added at t=40 minutes (see arrow in FIG. 3A and FIG. 3B) and resulted in vesicle rupture. The extent of vesicle rupture was interpreted by the structural transformation of the adsorbed vesicle layer, as evidenced by a net positive Δf shift and negative ΔD shift.

The rupture time was defined as the period from initial peptide attachment until there was rupture of most adsorbed vesicles (Δf>−70 Hz, as compared to the baseline). The rupture times are reported as mean±standard deviation for n=3 independent experiments). Based on the rupture times, the peptide were ranked according to the speed of vesicle rupture, with anti-infective peptide TSG001 (SEQ ID NO:1) clearly demonstrating the quickest vesicle rupture which is consistent with its helical induction.

The peptides were ranked with respect to their speed of vesicle rupture ranking (1 is most preferred due to quicker rupture of small lipid vesicles mimicking virus envelope composition): (1) anti-infective peptide TSG001 (SEQ ID NO:1): 5.9±2.3 min; (2) AH (SEQ ID NO:10): 14.7±3.5 min; and (3) C5A (SEQ ID NO:11): 15.9±2.8 min.

Method: QCM-D experiments were performed on a Q-Sense E4 instrument (Biolin Scientific, Gothenburg, Sweden). Experimental data was collected at several overtones (n=3, 5, 7, 9), and the changes in frequency (Δf) and energy dissipation (ΔD) were monitored as functions of time. The reported measurement values are from the third overtone (n=3) and were normalized accordingly (Δfn=3/3). All measurements were performed on QCM-D sensor crystals (Biolin Scientific) with gold coats. The substrates were cleaned with 1% w/w sodium dodecyl sulfate (SDS) solution, and then rinsed with water and ethanol, sequentially. After gentle drying with a stream of nitrogen air, the crystals were subjected to oxygen plasma treatment (Harrick Plasma, Ithaca, NY, USA) for ~1 minute immediately before experiment.

6.12 Solubility of Peptides

The solubility of peptides in distilled water was assessed. Lyophilized peptides were reconstituted in distilled water at a concentration of 2 mg/mL. The theoretical molar mass was determined by the mass concentration and molar mass of the peptide. The experimental molar mass was determined by 280 nm absorbance measurements. The results for TSG001, AH and C5A are described in Table 45. Essentially, C5A is not readily soluble in water and needs DMSO for solubilization.

TABLE 45

| Peptide | Experimental Molar Mass (µM) | Theoretical Molar Mass (µM) | % Reconstitution in Distilled Water | Visual Appearance of Solution |
|---|---|---|---|---|
| TSG001 | 826 | 1020 | 81 | Clear |
| AH (control) | 475 | 609 | 78 | Clear |
| C5A (control) | 428 | 866 | 49 | Turbid |

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A peptide of 16 to 26 amino acid residues in length comprising an amino acid sequence selected from the group consisting of: SGSWLRDVWTWLQSKL (SEQ ID NO:1), GSSWLRDVWTWLQSKL (SEQ ID NO:2), GSSWLRDVWTWLQSAL (SEQ ID NO:3), GSSWLRDVWTKLQSWL (SEQ ID NO:4), and GSSWLRDIWTALQSWL (SEQ ID NO:6).

2. A pegylated peptide comprising the peptide as defined in claim 1 linked to one, two or more polyethylene glycol (PEG) polymers.

3. The pegylated peptide of claim 2, wherein the one, two or more PEG polymers is linked to the N-terminus of the peptide, or the C-terminus of the peptide.

4. The pegylated peptide of claim 3, which comprises the following structure: NH$_2$-PEG12-amide-PEG12-peptide wherein the peptide is 16 to 26 amino acids in length comprising an amino acid sequence selected from the group consisting of SEQ ID NOs: 1, 2, 3, 4, and 6.

5. The pegylated peptide of claim 2, wherein each PEG polymer is in the molecular weight range of 500 to 5000 daltons.

6. The pegylated peptide of claim 5, wherein the one, two or more PEG polymers is branched or non-branched.

7. A peptide of 16 amino acid residues in length, consisting of an amino acid sequence selected from the group consisting of: SGSWLRDVWTWLQSKL (SEQ ID NO:1), GSSWLRDVWTWLQSKL (SEQ ID NO:2), GSSWLRDVWTWLQSAL (SEQ ID NO:3), GSSWLRDVWTKLQSWL (SEQ ID NO:4), and GSSWLRDIWTALQSWL (SEQ ID NO:6).

8. The peptide of claim 7, wherein the amino acid residues are L amino acids, D amino acids, or a mixture of D and L amino acids.

9. A composition comprising:
(a) (i) a peptide of 16 to 26 amino acid residues in length comprising an amino acid sequence selected from the group consisting of: SGSWLRDVWTWLQSKL (SEQ ID NO:1), GSSWLRDVWTWLQSKL (SEQ ID NO:2), GSSWLRDVWTWLQSAL (SEQ ID NO:3), GSSWLRDVWTKLQSWL (SEQ ID NO:4), and GSSWLRDIWTALQSWL (SEQ ID NO:6), and
(ii) a carrier; or
(b) (i) a pegylated peptide of 16 to 26 amino acid residues in length comprising an amino acid sequence selected from the group consisting of: SGSWLRDVWTWLQSKL (SEQ ID NO:1), GSSWLRDVWTWLQSKL (SEQ ID NO:2), GSSWLRDVWTWLQSAL (SEQ ID NO:3), GSSWLRDVWTKLQSWL (SEQ ID NO:4), and GSSWLRDIWTALQSWL (SEQ ID NO:6), and
(ii) a carrier.

10. An in vitro or ex vivo method for inhibiting growth, replication, or infectivity of a microorganism, comprising contacting the microorganism with an effective amount of a composition comprising:
(a) (i) a peptide of 16 to 26 amino acid residues in length comprising an amino acid sequence selected from the group consisting of: SGSWLRDVWTWLQSKL (SEQ ID NO:1), GSSWLRDVWTWLQSKL (SEQ ID NO:2), GSSWLRDVWTWLQSAL (SEQ ID NO:3), GSSWLRDVWTKLQSWL (SEQ ID NO:4), and GSSWLRDIWTALQSWL (SEQ ID NO:6), and
(ii) a carrier; or
(b) (i) a pegylated peptide of 16 to 26 amino acid residues in length comprising an amino acid sequence selected from the group consisting of: SGSWLRDVWTWLQSKL (SEQ ID NO:1), GSSWLRDVWTWLQSKL (SEQ ID NO:2), GSSWLRDVWTWLQSAL (SEQ ID NO:3), GSSWLRDVWTKLQSWL (SEQ ID NO:4), and GSSWLRDIWTALQSWL (SEQ ID NO:6), and
(ii) a carrier.

11. The method of claim 10, wherein the microorganism is a bacteria or a virus.

12. The method of claim 11, wherein the bacteria is Gram-positive or Gram-negative.

13. The method of claim 12, wherein the Gram-positive bacteria is *Staphylococcus aureus*, Enterococci, Streptococci, *Clostridium difficile, Propionibacterium acnes,* or *Bacillus anthracis.*

14. The method of claim 12, wherein the Gram-negative bacteria is *Pseudomonas aeruginosa, Moraxella catarrhalis,* or *Haemophilus influenzae.*

15. The method of claim 11, wherein the bacteria is Methicillin-sensitive *Staphylococcus aureus*, Methicillin-resistant *Staphylococcus aureus*, Vancomycin-sensitive Enterococci, Vancomycin-resistant Enterococci, penicillin-sensitive *Streptococcus pneumoniae*, penicillin-resistant *Streptococcus pneumoniae*, ciprofloxacin-resistant or clindamycin-resistant.

16. The method of claim 11, wherein the virus belongs to the Flaviviridae, Togaviridae, Filoviridae, Arenaviridae, Poxviridae, Bunyaviridae, or Retroviridae family.

17. The method of claim 11, wherein the virus is a dengue virus, Zika virus, Yellow Fever virus, Japanese encephalitis virus, Marburg virus, Chikungunya virus, Ebola virus, HIV, or influenza virus.

18. A method for disinfecting an inanimate object or biological material, comprising contacting the inanimate object with a composition comprising:
   (a) (i) a peptide of 16 to 26 amino acid residues in length comprising an amino acid sequence selected from the group consisting of: SGSWLRDVWTWLQSKL (SEQ ID NO:1), GSSWLRDVWTWLQSKL (SEQ ID NO:2), GSSWLRDVWTWLQSAL (SEQ ID NO:3), GSSWLRDVWTKLQSWL (SEQ ID NO:4), and GSSWLRDIWTALQSWL (SEQ ID NO:6), and
   (ii) a carrier, or
   (b) (i) a pegylated peptide of 16 to 26 amino acid residues in length comprising an amino acid sequence selected from the group consisting of: SGSWLRDVWTWLQSKL (SEQ ID NO:1), GSSWLRDVWTWLQSKL (SEQ ID NO:2), GSSWLRDVWTWLQSAL (SEQ ID NO:3), GSSWLRDVWTKLQSWL (SEQ ID NO:4), and GSSWLRDIWTALQSWL (SEQ ID NO:6), and
   (ii) a carrier.

19. A method for disinfecting an inanimate object or biological material, comprising contacting the inanimate object with a wipe containing a peptide of 16 to 26 amino acid residues in length comprising an amino acid sequence selected from the group consisting of: SGSWLRDVWTWLQSKL (SEQ ID NO:1), GSSWLRDVWTWLQSKL (SEQ ID NO:2), GSSWLRDVWTWLQSAL (SEQ ID NO:3), GSSWLRDVWTKLQSWL (SEQ ID NO:4), and GSSWLRDIWTALQSWL (SEQ ID NO:6).

* * * * *

UNITED STATES PATENT AND TRADEMARK OFFICE
CERTIFICATE OF CORRECTION

| | | |
|---|---|---|
| PATENT NO. | : 11,866,460 B2 | Page 1 of 1 |
| APPLICATION NO. | : 17/348593 | |
| DATED | : January 9, 2024 | |
| INVENTOR(S) | : Nam-Joon Cho et al. | |

It is certified that error appears in the above-identified patent and that said Letters Patent is hereby corrected as shown below:

In the Claims

<u>Column 133, Claim 4, Line 44:</u>
"claim 3," should read: --claim 2,--.

<u>Column 136, Claim 18, Line 6:</u>
"a carrier, or" should read: --a carrier; or--.

Signed and Sealed this
Fourteenth Day of January, 2025

Derrick Brent
*Acting Director of the United States Patent and Trademark Office*